(12) United States Patent
Asolkar et al.

(10) Patent No.: US 11,013,236 B2
(45) Date of Patent: *May 25, 2021

(54) **PESTICIDAL *FLAVOBACTERIUM* STRAIN AND BIOACTIVE COMPOSITIONS METABOLITES AND USES**

(71) Applicant: Marrone Bio Innovations, Inc., Davis, CA (US)

(72) Inventors: Ratnakar Asolkar, Davis, CA (US); Ana-Lucia Cordova-Kreylos, Davis, CA (US); Marja Koivunen, Davis, CA (US); Margarita Rodriguez, Davis, CA (US); Lijuan Xing, Newark, DE (US); Pamela Marrone, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 951 days.

This patent is subject to a terminal disclaimer.

(21) Appl. No.: 14/382,624

(22) PCT Filed: Mar. 13, 2013

(86) PCT No.: PCT/US2013/030631
§ 371 (c)(1),
(2) Date: Sep. 3, 2014

(87) PCT Pub. No.: WO2013/138398
PCT Pub. Date: Sep. 19, 2013

(65) Prior Publication Data
US 2015/0031534 A1    Jan. 29, 2015

Related U.S. Application Data

(60) Provisional application No. 61/609,937, filed on Mar. 13, 2012, provisional application No. 61/733,730, filed on Dec. 5, 2012.

(51) Int. Cl.
| | | |
|---|---|---|
| *A01N 63/10* | (2020.01) | |
| *C12N 1/20* | (2006.01) | |
| *A01N 35/04* | (2006.01) | |
| *A01N 37/10* | (2006.01) | |
| *A01N 35/02* | (2006.01) | |
| *A01N 37/46* | (2006.01) | |
| *A01N 31/08* | (2006.01) | |
| *C12P 7/26* | (2006.01) | |
| *C12R 1/20* | (2006.01) | |

(52) U.S. Cl.
CPC .............. *A01N 63/10* (2020.01); *A01N 31/08* (2013.01); *A01N 35/02* (2013.01); *A01N 35/04* (2013.01); *A01N 37/10* (2013.01); *A01N 37/46* (2013.01); *C12N 1/20* (2013.01); *C12P 7/26* (2013.01); *C12R 1/20* (2013.01)

(58) Field of Classification Search
CPC ........ A01N 63/10; A01N 31/08; A01N 35/02; A01N 35/04; A01N 37/10; A01N 37/46; C12N 1/20; C12P 7/26; C12R 1/20

USPC .......................................................... 424/93.4
See application file for complete search history.

(56) References Cited

U.S. PATENT DOCUMENTS

| | | | | |
|---|---|---|---|---|
| 5,273,746 | A | 12/1993 | Payne | |
| 5,503,651 | A * | 4/1996 | Kloepper | A01N 63/00 435/253.3 |
| 6,311,426 | B1 * | 11/2001 | Mehta | C05D 9/00 47/1.01 F |
| 7,994,138 | B2 | 8/2011 | Awada | |
| 2003/0082147 | A1 | 5/2003 | Gouge | |
| 2005/0266036 | A1 * | 12/2005 | Awada | A01N 25/30 424/405 |
| 2006/0166825 | A1 * | 7/2006 | Goulet | A01N 63/02 504/117 |
| 2011/0207604 | A1 | 8/2011 | Asolkar | |

FOREIGN PATENT DOCUMENTS

EP        171381 A * 2/1986

OTHER PUBLICATIONS

CA 2866165 Office Action dated Aug. 27, 2015.
Abe, I. et al.(2002) "Enzymatic Formation of an Unnatural $C_6$—$C_5$ Aromatic Polyketide by Plant Type III Polyketide Synthases" *Organic Letters* 4(21):3623-36-26.
Barnsley, E.A.(1988) "Metabolism of 2, 6-dimethylnaphthalene by flavobacteria" *Appl. Environ. Microbiol.* 54(2):428.
Bernardet, Jean-Francois. (2009) "Flavobacterium: a member of the family" INRA, UR892 *Virologie et Immunology Moleculaires*. (September).
Bodour, A. et al.(2004) "Structure and Characterization of Flavolipids, a Novel Class of Biosurfactants Produced by *Flavobacterium* sp. Strain MTN11" *Appl. Environ. Microbiol.* 70(1):114.
Bernardet, J. et al. (2006)"The Genus *Flavobacterium*" *Prokaryotes* 7:481-531.
Bernardet, et al. (2006) "An Introduction to Family of Flavobacteriaceae" *Prokaryotes* 7:455-480.
Ferezou, J. et al. (1985) "Biomimetic Synthesis of Bacterial C50 Carteonoids Decaprenoxanthin and C.p.450" *Tetrahaedron* 41(7):1277-1287.
Fotopoulou, F. et al. (2004) "Non-Specific Biodegradation of Organophosphorus Nematicides by Soil Bacteria" 3rd European Conference on Pesticides and Related Organic Micropollutants in the Environment. (Abstract).

(Continued)

*Primary Examiner* — Jennifer M. H. Tichy
(74) *Attorney, Agent, or Firm* — Singleton Law, PLLC; Chainey P. Singleton; Ying-Horng Liu

(57) ABSTRACT

Provided is a pesticidal *Flavobacterium* strain and bioactive compositions and metabolites derived therefrom as well as their methods of use for controlling pests.

10 Claims, 17 Drawing Sheets

Specification includes a Sequence Listing.

(56) References Cited

OTHER PUBLICATIONS

Francis, G.W. et al. (1970) "New Cartenoid Glycosides From Oscillatoria Limosa" *Phytochemistry*, 9:629-635.
Kamiyama, T. et al. (1995) "Sulfobacins A and B, Novel von Willebrand Factor Receptor Antagonist" The Journal of Antibiotics (September).
Kaplan, C. et al. (2004) "Bacterial Succession in a Petroleum Land Treatment Unit" *Appl. Environ. Microbiol.* 70(3):1777.
Kato, H. et al. (1998) "Chemical Structure of Lipid A Isolated from Flavobacterium meningosepticum Lipopolysaccharide" *Journal of Bacteriology* 180(15):3891-3899.
Kobayashi, J. (1995) "Flavocristamides A and B, New DNA Polymerase α Inhibitors from a Marine Bacterium *Flavobacterium* sp." *Tetrahedron* 51(38):10478-10490.
Liaaen-Jensen, S. et al. (1968) "Bacterial Carotenoids XXVII: $C_{50}$ Carotenoids. 3. Structure Determination of Dehydrogenans.-P439" *ACTA Chemica Scandinavica* 22:1171-1186.
Ortiz-Hernandez, M.L. et al. (2003) "Study of the Mechanism of *Flavobacterium* sp. for hydrolyzing organophosphate pesticides" *Fundamental and Clinical Pharmacology* 17 ed. 717-723.
Shoji, J. et al. (1984) "Chitinovorins A, B and C, Novel β-Lactam Antibiotics of Bacterial Orgin" *The Journal of Antibiotics* (November).
Shoji, J. et al. (1985)"Isolation of Chitinovorin D" *The Journal of Antibiotics* (April).
Singh, P. et al. (1984) "Bacterial Production of 7-Formamidocephalosporins Isolation and Structure Determination" *The Journal of Antibiotics* XXXVII(7): 773.
Yokoyama, A. et al. (1996) "New Cartenoid Sulfates Isolated from a Marine Bacterium" *Biosci. Biotech. Biochem.* 60 (11):1877-1878.
Yokoyama, A. et al. (1995) "Isolation of Myxol from a Marine Bacterium *Flavobacterium* sp. Associated with a Marine Sponge" *Fisheries Science* 61(4):684-686.
Yagi,H. et al. (1999) "A Novel Monoacyldiglycosyl-Monoacylglycerol from Flavobacterium marinotypicum" *J. Nat. Prod.* 62:631-632.
Extended Search Report EP13761233.9 dated Jul. 22, 2015.
Liu, Jie et al. "*Sphingobacterium nematocida* sp. nov., a nematicidal endophytic bacterium isolated from tobacco" International Journal of Systematic and Evolutionary Microbiology (2012) 62:1809-1813.
Canadian Office Action in App. No. 2,866,165 dated Apr. 6, 2018, pp. 1-7.

* cited by examiner

PESTICIDAL *FLAVOBACTERIUM* STRAIN AND BIOACTIVE COMPOSITIONS METABOLITES AND USES

TECHNICAL FIELD

Disclosed herein is a pesticidal *Flavobacterium* strain and bioactive compositions and metabolites derived therefrom, as well as their methods of use for controlling pests and promoting plant growth, particularly, root health.

BACKGROUND ART

Natural products are substances produced by microbes, plants, and other organisms. Microbial natural products offer an abundant source of chemical diversity, and there is a long history of utilizing natural products for pharmaceutical purposes. Despite the emphasis on natural products for human therapeutics, where more than 50% are derived from natural products, only 11% of pesticides are derived from natural sources. Nevertheless, natural product pesticides have a potential to play an important role in controlling pests in both conventional and organic farms. Secondary metabolites produced by microbes (bacteria, actinomycetes and fungi) provide novel chemical compounds which can be used either alone or in combination with known compounds to effectively control insect pests and to reduce the risk for resistance development. There are several well-known examples of microbial natural products that are successful as agricultural insecticides (Thompson et al., 2000; Arena et al., 1995; Krieg et al. 1983).

The development of a microbial pesticide starts with the isolation of a microbe in a pure culture. It then proceeds with efficacy and spectrum screening using in vitro, in vivo or pilot scale trials in a greenhouse and in the field. At the same time, active compounds produced by the microbe are isolated and identified. For the commercialization of a microbial pesticide, the microbe has to be economically produced by fermentation at an industrial scale and formulated with biocompatible and approved additives to increase efficacy and to maximize the ease of application.

Nematodes are non-segmented, bilaterally symmetric, worm-like invertebrates that posses a body cavity and complete digestive system but lack respiratory and circulatory systems. Their body wall contains a multilayer cuticle, a hypodermis with four longitudinal cords, and internal musculature (Chitwood, 2003). Their body contents are mostly occupied by digestive and reproductive systems. Nematodes may be classified as either parasitic or free living. Parasitic nematodes may be classified by their hosts (e.g., plant parasites). Free living nematodes may be classified according to their feeding habits and include the following groups: (1) omnivores; (2) bacterial feeders; (3) fungal feeders and (4) predators.

Plant parasitic nematodes generally feed on underground parts of plants, such as roots, bulbs, and tubers as well as above ground parts of the plants, such as leaves and stems. Annual crop losses caused by plant-parasitic nematodes have been estimated to exceed US $100 billion (Koenning et al., 1999). Examples of plant parasitic nematodes include but are not limited to nematodes belonging to *Meloidogyne* spp. (e.g., root-knot nematodes); *Pratylenchus* spp. (e.g., lesion nematodes) *Heterodera* spp. (e.g., cyst nematodes); *Globodera* spp. (cyst nematodes); *Ditylenchus* spp. (e.g., stem and bulb nematodes); *Tylenchulus* spp. (e.g., citrus nematodes), *Xiphinema* spp. (e.g., dagger nematodes), *Radopholus* spp. (burrowing nematodes); *Rotylenchulus* spp. (e.g. reniform nematodes); *Helicotylenchus* spp. and *Scutellonema* spp (e.g. spiral nematodes); *Belonolaimus* spp. (e.g., sting nematodes); *Bursaphelenchus* spp. (e.g. pine wilt nematodes); *Hoplolaimus* spp. (lance nematodes), *Longidorus* spp. (needle nematodes); *Nacobbus* spp. (false root-knot nematodes); and *Aphelenchoides* spp (foliar nematodes). The most efficient means for controlling nematodes is via nematicides that inhibit egg hatching, juvenile motility and/or plant infectivity. The development of chemical control for plant-parasitic nematodes is challenging because of both environmental and physiological reasons: (1) most phytoparasitic nematodes live in a confined area in soil near the roots and hence, delivery of a chemical nematicide is difficult and (2) the outer surface of nematodes is a poor biochemical target, and is impermeable to many organic molecules (Chitwood, 2003). Moreover, delivery of toxic compounds by an oral route is nearly impossible because most plant parasitic nematode species ingest material only after they have penetrated and infected plant roots. Therefore, nematicides have tended to be broad-spectrum toxins with high volatility or with other chemical and physical properties promoting their motility in soil.

During the past decade, halogenated hydrocarbons (e.g. ethylene dibromide, methyl bromide) have been the most heavily used nematicides around the world. Due to their high human toxicity and detrimental effects on stratospheric ozone layer these compounds were banned in the Montreal Protocol but the use of methyl bromide for nematode and plant pathogen control was extended in the US due to lack of substitution products. Along with organophosphates, carbamates are the most effective non-fumigant nematicides. Unfortunately, most carbamates such as aldicarb and oxamyl are also highly toxic. As of August 2010, the manufacturer of aldicarb, Bayer, has agreed to cancel all product registrations on potatoes and citrus in the US, and aldicarb will be completely phased out by the end of August, 2018. Recently, abamectin—a mixture of two avermectins produced by a soil actinomycete, *Streptomyces avermitilis*—has been registered for nematicidal use (Faske and Starr, 2006). Syngenta markets this active ingredient as a seed treatment for cotton and vegetables under the trade name Avicta®.

Several microbial plant/nematode pathogens have been reported to be active against plant parasitic nematodes (Guerena, 2006). These biological control agents include the bacteria *Bacillus thuringiensis, Burkholderia cepacia, Pasteuria penetrans* and *P. usgae*. Pasteuria Biosciences has launched *P. usgae* against sting nematodes on turf in the southeastern US. Nematicidal fungi include, but are not limited to, *Trichoderma harzianum, Hirsutella rhossiliensis, H. minnesotensis, Pochonia chlamydosporia* (synonym. *Verticillium chlamydosporum*), *Arthrobotrys dactyloides*, and *Paecilomyces lilanicus* (marketed as BioAct® and Melo-Con® by Prophyta). Another fungus, a killed fungus, *Myrothecium verrucaria* is available in a commercial formulation, DiTera®, by Valent Biosciences.

Other commercial bionematicides include Deny® and Blue Circle® (*B. cepacia*), Activate® (*Bacillus chitinosporus*) (Quarles, 2005) and an Israeli product BioNem® (*Bacillus firmus*) (now marketed by Bayer as a seed treatment VOTiVO®) (Terefe et al. 2009). It has been hypothesized that the detrimental effect of microbial isolates on nematode egg hatching, juvenile motility and infectivity can be attributed to toxins produced by these organisms (Hallman and Sikora, 1996; Marrone et al, 1998; Siddiqui and Mahmood, 1999; Saxena et al., 2000; Meyer and Roberts, 2002), ability to parasitize or even trap nematodes (Siddiqui and Mahmood, 1996; Kerry, 2001; Jaffee and Muldoon, 1995), induction of systemic resistance (Hasky-Gunther et al., 1998), changing nematode behavior (Sikora and Hoffman-Hergarter, 1993) or interfering with plant recognition (Oostendorp and Sikora, 1990).

Botanical nematicides such as plant extracts and essential oils can be used to control nematodes (Kokalis-Burrelle and Rodriguez-Kabana, 2006). Chitwood has summarized the options of using plant-derived compounds for nematode control in his recent review article (Chitwood, 2002). Siddiqui and Alam (2001) demonstrated that potting soil amended with plant parts from the neem tree (*Azadirachta indica*) and Chinaberry tree (*Melia azadirah*) inhibited root-knot nematode development of tomatoes. However, no neem products are currently registered in the US for use against nematodes. A new botanical product from Chile (Nema-Q®) based on a *Quillaja saponaria* tree extract containing saponins (bidesmosidic derivatives of quillajic acid substituted with a trisaccharide at C-3 and an oligosaccharide in C-28) has been recently registered as a an organic nematicide through US EPA and listed for organic farming by the Organic Materials Review Institute (OMRI). It is marketed by Brandt.

Crop rotation to a non-host crop is often adequate by itself to prevent nematode populations from reaching economically damaging levels (Guerena 2006). Allelochemicals are plant-produced compounds that affect the behavior of organisms in the plant's environment. Examples of nematocidal allelochemicals include polythienyls, glucisonolates, alkaloids, lipids, terpenoids, steroids, triterpenoids and phenolics (Kokalis-Burrelle and Rodriguez-Kabana, 2006; Chitwood, 2002). When grown as cover crops, bioactive compounds from allelopathic plants are exuded during the growing period and/or released to the soil during biomass decomposition. *Brassica* crops can be used for biofumigation—a pest management strategy based on the release of biocidal volatiles during decomposition of soil-incorporated tissue (Kirkegaard and Sarwar, 1998). However, studies of Roubtsova et al. (2007) on the effect of decaying broccoli tissue on *M. incognita* numbers indicated that for proper control, thorough mixing of plant tissue with the complete nematode-infected soil volume was necessary.

The future of nematode control in agricultural soils relies on two factors: development of nematode resistant crops and the discovery and development of new, broad-spectrum, less toxic nematicides. The cost of research, development and registration of a new chemical nematicide is extremely high (>$200 million), which limits their development. Of the 497 new active ingredients registered for use as a pesticide from 1967 to 1997, only seven were registered as nematicides (Aspelin and Grube, 1999). Besides conventional chemical methods, RNA interference (RNAi) has been proposed as a method for controlling nematodes. Use of gene silencing via RNAi was first demonstrated on *Caenorhabditis elegans* and quite recently also for plant parasitic nematodes such as *Meloidogyne* spp. (Bakhetia et al. 2005). The search for new microbial strains to use as sources for biological nematicides is an important goal in order to reduce the significant economic damage caused by plant-parasitic nematodes as well as to reduce the use of toxic compounds currently registered for nematode control.

According to Sasser and Freckman (1987), crop losses by nematodes range from 8 to 20% on major crops around the world. Plant parasitic nematodes can cause considerable crop damage with annual losses estimated at $87 billion worldwide (Dong and Zhang, 2006). Fumigants such as methyl bromide are very effective in controlling both soil-borne plant diseases and nematodes but due to the high mammalian toxicity, ozone depleting effects and other residual effects, the use of methyl bromide has already been banned in various countries and its complete withdrawal from the market is planned by international agreement (Oka et al., 2000). Chemical alternatives such as methyl iodide, 1,3-Dichloropropene, and cholorpicrin also have issues with mammalian and environmental safety. Chemical non-fumigant nematicides are being phased out and banned. Most recently, the US-EPA announced that aldicarb was being phased out.

Uses of *Flavobacterium* and Products Produced Therefrom

*Flavobacterium* sp., a gram negative bacterium, is a member of the Flavobacteriaceae family (reviewed in Bernardet et al., 2006a and 2006b). Species of *Flavobacterium* have been found to be pathogenic to fish, algae and soil organism. *Flavobacterium* has been found to produce a variety of enzymes involved in the degradation of agar, alginate, chitin, pectin, xylan, keratin, laminarin. For example, it is thought that polysaccharide-degrading enzymes may be produced by *Flavobacterium*. Such enzymes may degrade the cell wall of, e.g., various pathogens. *Flavobacterium* may also produce proteases. Recently, *Flavobacterium* has also been found to produce anti-fungal compounds that may be used to control banana pathogens.

Species of *Flavobacterium* have been found to produce a variety of compounds. Some species in this genus were able to oxidize a broad range of aromatic hydrocarbons (see, for example, Barnsley E. 1988).

The fermentation of *Flavobacterium* sp. SC 12154 was found to produce deacetoxycephalosprin C and a mixture of novel 7-substituted cephalosporins (Singh et al., 1984) which were reported to exhibit weak antibacterial activity. Flavocristamides A & B, two sulfonolipids with inhibitory activity against DNA polymerase α were isolated from a marine bacterium *Flavobacterium* sp. (Kobayashi et al., 1995) which was separated from the marine bivalve *Cristaria plicata*. The isolation and identification of chitinovorins A, B & C, which belong to the class of β-lactam antibiotics were reported from the culture broth of *Flavobacterium chitinovorum* (Shoji et al., 1984). The more strongly basic antibiotic named chitinovorin D was later isolated from a *Flavobacterium* sp. PB-5246, along with the known chitinovorins A, B & C (Shoji et al., 1985). Sulfobacins A and B, novel von Willebrand factor (vWF) receptor antagonists, were isolated from the culture broth of *Chyseobacterium* sp. later reported as *Flavobacterium* sp. NR 2993 (Kamiyama et al., 1995). New polar carotenoid sulfates were isolated from the marine bacterium, strain PC-6 identified as a *Flavobacterium* sp., and were assigned as (2R,3S,2'R,3'R)-4-ketonostoxanthin-3'-sulfate and (2R,3S,2'R,3'R)-nostoxanthin-3-sulfate (Yokoyama et. al, 1996). The chemical structure of the lipid A of the lipopolysaccharide component isolated from *Flavobacterium meningosepticum* IFO 12535 (Kato et al., 1998) was elucidated on the basis of mass spectroscopy and chemical modification. A novel monoacyldiglycosyl-monoacylglycerol was isolated from the gram negative bacterium *Flavobacterium marinotypicum* ATCC 19260 along with other glycolipids and phospholipids (Yagi & Maruyama, 1999). The arctic bacterium of the *Cytophaga-Flavobacterium-bacteroides* was found to produce several volatile organic compounds (Dickschat et al., 2005), which were dominated by methyl ketones. The methyl ketones were aliphatic saturated, or unsaturated, and contains 12-18 carbon atoms, sometimes with terminal methyls branches.

In addition to the above metabolites, the other known compounds from the genus *Flavobacterium* sp. are myxol (Yokoyama et al., 1995), a compound that belongs to the class of carotenoids, which has been previously reported from blue-green algae *Oscillatoria limosa* (Francis et al., 1970); decaprenoxanthin, the bicyclic $C_{50}$ carotenoid dial from *Flavobacterium dehydrogenans* (Liaaen-Jensen, et al., 1968), which was later synthesized due to its interesting structure (Ferezou & Julia, 1985).

Furthermore, a biosurfactant-producing *Flavobacterium* sp., strain MTN11 (accession number AY162137) isolated from samples of arid soil has also been found to produce flavolipids which are very polar and are good emulsifiers (Bodour, 2004). Examples include arthrobactin and aerobactin. It has been suggested that these flavolipids could be used in contaminated soil to mitigate metal toxicity during organic biodegradation (Kaplan and Kitts, 2004). Specifically, Kaplan and Kitts (2004), found that organisms attributed to *Flavobacterium* spp. and *Pseudomonas* spp. from 16S rRNA gene sequence were present in soil contaminated with petroleum hydrocarbons particularly during the degradation phase of these petroleum hydrocarbons.

BRIEF SUMMARY

Provided herein are novel uses and combinations and, in particular, compositions comprising a strain of *Flavobacterium* sp.

In a particular embodiment, the strain of *Flavobacterium* spp. may have the following characteristics:

(A) a 16S rRNA gene sequence comprising the forward sequence having at least 99% identity to the sequence set forth in SEQ ID NO:3 and a reverse sequence having at least 99% identity to the sequence set forth in SEQ ID NO:4 and a consensus sequence having at least 99% identity to the sequence set forth in SEQ ID NO:5;

(B) pesticidal activity;

(C) growth modulating and particularly growth promoting activity;

(D) produces a pesticidal compound having the following properties: (1) has a molecular weight of about 150-195 as determined by Liquid Chromatography/Mass Spectroscopy (LC/MS); (2) has $^1$H NMR values of δ 7.60, 7.52, 6.83, 6.68, 2.74, 1.14 and has $^{13}$C NMR values of 203.96, 161.90, 145.11, 131.78, 131.78, 127.28, 123.83, 117.24, 117.24, 34.52, 8.89; (3) has an High Pressure Liquid Chromatography (HPLC) retention time of about 8-14 minutes, on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm;

(E) is non-pathogenic to vertebrate animals;

(F) is susceptible to tetracycline, erythromycin, streptomycin, penicillin, ampicillin, Oxytetracycline, Chloramphenicol, Ciprofloxacin, Gentamicin, Piperacillin, Imipenem and Sulphamethoxazole-Trimethoprim.

In particular, the *Flavobacterium* species is a *Flavobacterium* strain having the identifying characteristics of *Flavobacterium* sp. H492 (NRRL Accession No. B-50584). Therefore, in a related aspect, said *Flavobacterium* strain is provided.

Also provided is a substantially pure culture or whole cell broth comprising said strain or cell fraction, filtrate, supernatant, extract and/or compound derived from said *Flavobacterium* strain or compound (e.g., metabolites) derived from said strain, substantially pure culture, whole cell broth, cell fraction, filtrate, supernatant and/or extract. Further provided is a composition comprising said substantially pure culture or whole cell broth comprising said strain or, cell fraction, filtrate, supernatant, compound and/or extract derived from this *Flavobacterium* strain and a carrier, diluent, surfactant a carrier, surfactant or adjuvant.

Thus provided herein is a method for modulating pest infestation in a plant comprising applying to a plant, and/or seeds thereof and/or substrate used for growing said plant an amount of a substantially pure culture, whole cell broth comprising a strain of *Flavobacterium* species, or cell fraction, filtrate, supernatant, extract and/or compound, including but not limited to one or more metabolites derived from said strain of *Flavobacterium* species or compounds (e.g., metabolites) derived from said substantially pure culture, whole cell broth, cell fraction, filtrate, supernatant and/or extract and optionally another nematocidal substance in an amount effective to modulate said pest infestation. In a particular embodiment, the pest is a nematode. In a more particular embodiment, the pest is a plant parasitic nematode.

Also provided herein is a pesticidal combination synergistic to at least one pest comprising as active components: (a) substantially pure culture, whole cell broth comprising a strain of *Flavobacterium* species or cell fraction, filtrate, supernatant, extract, or compound (e.g., metabolite) derived from said strain or derived from said substantially pure culture or whole cell broth comprising said strain of *Flavobacterium* species and (b) another pesticidal substance, wherein (a) and (b) are present in synergistic amounts. The pest, in a particular embodiment, may be a nematode, but may also include, but is not limited to, an insect pest, plant fungus, plant virus and plant bacteria and weeds. Further, the combination may be a composition. The other pesticidal substance may be (a) derived from a microorganism; (b) a natural product and/or (b) a chemical pesticide and in particular a chemical insecticide or nematicide.

In a related aspect, provided herein is a method for synergistically modulating infestation of at least one pest or pest species in or on a plant comprising applying to a plant and/or seeds thereof and/or substrate for growing said plant the combinations set forth above with an amount of the combination effective to modulate infestation of said pest or pest species. Also provided herein are isolated compounds obtainable or derived from *Flavobacterium* species, or alternatively, organisms capable of producing these compounds that can be used to control various pests, and/or also particularly, nematicidal pests.

Further provided is a method for modulating growth in a plant (e.g. crops such as fruits (e.g., strawberry, banana, watermelon, berries), vegetables (e.g., tomato, cucumber, squash, pepper, eggplant), or row crops (e.g., soy, wheat, rice, corn, cotton, peanut, potato), trees (e.g. pine trees), flowers, ornamental plants, shrubs (e.g., roses), bulb plants (e.g., onion, garlic), turf (e.g. bermudagrass, Kentucky bluegrass, fescues), or vines (e.g., grape vine) comprising applying to a plant, and/or seeds thereof and/or substrate used for growing said plant an amount of substantially pure culture or whole cell broth comprising said strain, or cell fraction, filtrate, supernatant, compound (e.g., metabolite) and/or extract derived from said strain of *Flavobacterium* species and optionally another growth promoting substance which modulate and in particular promote growth by, for example, modulating or in particular, promoting root establishment in said plant.

In a related aspect, provided herein is a method for synergistically modulating growth of a plant comprising applying to a plant and/or seeds thereof and/or substrate for growing said plant the combinations set forth above with an amount of the combination effective to modulate growth of said plant. Also provided herein are isolated compounds obtainable or derived from *Flavobacterium* species, or alternatively, organisms capable of producing these compounds that can be used to control growth of said plants.

The substantially pure culture or whole cell broth comprising said strain of a *Flavobacterium* species, or cell fraction, filtrate, supernatant, extract and/or compound (e.g., metabolite) derived from said strain of or substantially pure culture or whole cell broth comprising said *Flavobacterium* species compounds derived from said substantially pure culture, whole cell broth, cell fraction, filtrate, supernatant and/or extract may be applied to the roots of a plant before transplanting it to soil as well as the above-ground parts of the plant. Thus provided is a method for modulating root and shoot extension in a plant comprising: (a) treating one or more roots and shoots of a plant with said culture, whole cell broth, supernatant, filtrate and/or extract and/or one or more compounds (e.g., metabolites) derived from said culture, whole cell broth, supernatant, filtrate and/or extract of a strain of *Flavobacterium* sp. and optionally another growth promoting substance in an amount effective to modulate root and shoot extension when transplanted into soil; (b) transplanting the treated plant of (a) into soil.

In a related aspect, also provided is the use of a substantially pure culture or whole cell broth comprising or cell fraction, filtrate, supernatant and/or extract derived from a strain of *Flavobacterium* species or metabolites thereof, metabolites derived from said substantially pure culture, whole cell broth, cell fraction, filtrate, supernatant and/or extract of a strain of *Flavobacterium* sp. and optionally another growth promoting substance or agent for modulating growth in a plant and particularly for modulating root extension.

Also, in a related aspect, is a combination for use of a substantially pure culture or whole cell broth comprising said strain or cell fraction, filtrate, supernatant and/or extract derived from a strain of *Flavobacterium* species or said culture or whole cell broth or compounds (e.g., metabolites) thereof, compounds (e.g., metabolites) derived from said cell fraction, filtrate, supernatant and/or extract in modulating growth in a plant by, for example modulating and in particular, increasing the biomass of a plant, height of a plant, number of roots, weight of roots, comprising of a supernatant, filtrate and/or extract and/or one or more metabolites from said supernatant, filtrate and/or extract of a strain of *Flavobacterium* sp. and optionally another growth promoting substance or agent for modulating growth in a plant. The combination may be a synergistic combination.

Also provided is a use of a substantially pure culture or whole cell broth comprising a strain of *Flavobacterium* species, or cell fraction, filtrate, supernatant and/or extract derived from a strain of *Flavobacterium* species or compounds (e.g., metabolites) thereof, or compounds (e.g., metabolites) derived from said substantially pure culture, whole cell broth, cell fraction, filtrate, supernatant and/or extract and optionally another growth promoting substance that modulates germination of a seed in a plant, wherein said plant includes but is not limited to crops such as fruits (e.g., strawberry), vegetables (e.g., tomato, cucumber, squash, pepper, eggplant), or row crops (e.g., soy, wheat, rice, corn, cotton, peanut, potato), trees (e.g. pine trees), flowers, ornamental plants, shrubs (e.g., roses), turf (e.g. bermudagrass, Kentucky bluegrass, fescues), bulb plants (e.g., onion, garlic) or vines (e.g., grape vine) for modulating such germination. In a related aspect, provided is a method for modulating germination of a seed in a plant by treating said plant with an amount of a substantially pure culture or whole cell broth comprising a strain of *Flavobacterium* species, or cell fraction, filtrate, supernatant and/or extract derived from a strain of *Flavobacterium* species or compounds (e.g., metabolites) thereof, metabolites derived from said substantially pure culture, whole cell broth, cell fraction, filtrate, supernatant and/or extract and optionally another growth promoting substance in a plant effective to modulate said germination of a seed in a plant. The seed in a particular embodiment may be a genetically modified seed.

In a related aspect, also provided, is a combination for use in modulating germination of a seed in a plant comprising a substantially pure culture or whole cell broth comprising a strain of *Flavobacterium* species, or cell fraction, filtrate, supernatant and/or extract derived from a strain of *Flavobacterium* species or compounds (e.g., metabolites) thereof, or compounds (e.g., metabolites) derived from said substantially pure culture or whole cell broth, cell fraction, filtrate, supernatant and/or extract which modulate germination of a seed in a plant and optionally at least one of a second substance, wherein said second substance is a seed coating agent. The combination may be a synergistic combination.

These compounds may be obtained by (a) culturing a *Flavobacterium* strain in a culture medium under conditions sufficient to produce said compound to obtain a *Flavobacterium* culture and (b) isolating said compound produced in (a) from the whole cell broth of (a). In particular, the compound in step (b) may be isolated by (i) applying the whole cell broth to at least one of an ion exchange column, a size exclusion column or a reversed phase HPLC column to obtain column fractions; (ii) assaying the column fractions for pesticidal activity and (iii) concentrating column fractions of (ii) to obtain isolated compound. Alternatively, these compounds may be obtained by chemical synthesis and can be used as a pure compound or/as well as a crude product.

DETAILED DESCRIPTION OF THE INVENTION

Figure 1:
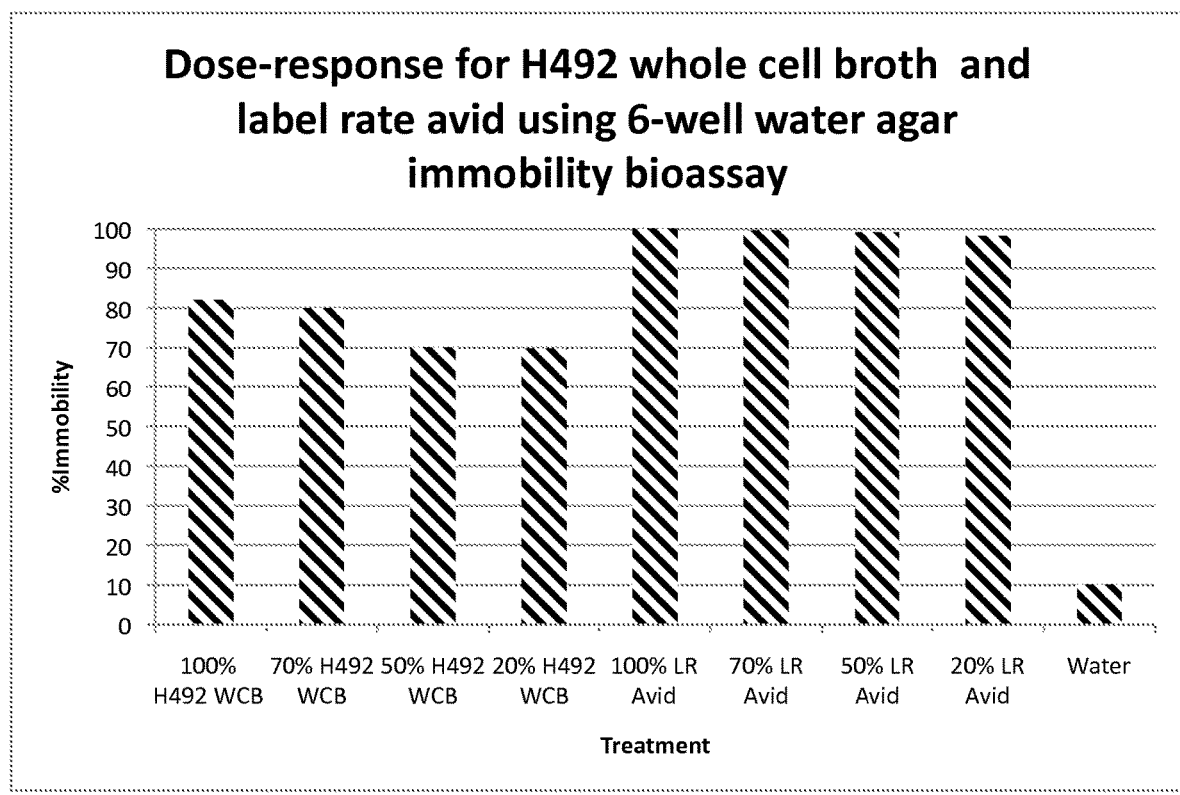
FIG. 1 shows the dose-response for H492 whole cell broth and label rate avid using 6-well water agar immotility bioassay.

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or medium used to culture or grow said organism.

As defined herein, "whole broth culture" or "whole cell broth" refers to a liquid culture containing both cells and media. If bacteria are grown on a plate, the cells can be harvested in water or other liquid, whole culture. The terms "whole broth culture" and "whole cell broth" are used interchangeably.

As defined herein, "supernatant" refers to the liquid remaining when cells grown in broth or are harvested in another liquid from an agar plate and are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer, organic solvent) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal and particularly, nematicidal activity.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods. A compound "derived from" a *Flavobacterium* species also encompasses a metabolite.

As defined herein, "carrier" is an inert, organic or inorganic material, with which the active ingredient is mixed or formulated to facilitate its application to plant or other object to be treated, or its storage, transport and/or handling.

As defined herein, "modulate", is used to mean to alter the amount of pest infestation, plant growth, root extension, seed germination or rate of spread of pest infestation, rate of plant growth, rate of root extension, rate of seed germination.

As defined herein, "pest infestation", is the presence of a pest in an amount that causes a harmful effect including a disease or infection in a host population or emergence of an undesired weed in a growth system.

As defined herein "pesticide", is a substance derived from a biological product or chemical substance that increase mortality or inhibit the growth rate of plant pests and includes but is not limited to nematicides, algaecides, herbicides, insecticides, plant fungicides, plant bactericides, and plant viricides.

As defined herein, a "plant parasitic nematode" is a nematode that feeds on and causes injury on any part of a plant.

As defined herein, "a non-parasitic nematode" is a nematode that exists independently in the soil and does not cause damage or injury to any part of a plant.

As defined herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As defined herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As defined herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As defined herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As defined herein, "aryl" refers to aromatic groups having in the range of 6 up to 14 carbon atoms and "substituted aryl" refers to aryl groups further bearing one or more substituents as set forth above.

As defined herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As defined herein, "alkoxy" refers to the moiety —O-alkyl-, wherein alkyl is as defined above, and "substituted alkoxy" refers to alkoxyl groups further bearing one or more substituents as set forth above.

As defined herein, "thioalkyl" refers to the moiety —S-alkyl-, wherein alkyl is as defined above, and "substituted thioalkyl" refers to thioalkyl groups further bearing one or more substituents as set forth above.

As defined herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As defined herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituent's as set forth above.

Substances

The substances used in the compositions and methods set forth above may be derived from *Flavobacterium* species or strain. As defined herein, "derived from" or "obtainable from" means that a compound may be isolated from or produced by a cell culture, whole cell broth, filtrate, supernatant, fraction or extract. Thus, a compound derived from a *Flavobacterium* species or strain also includes a compound isolated or produced by said species or strain. A compound "produced by" a cell culture, whole cell broth, filtrate, supernatant, cell fraction or extract may also be referred to as "a metabolite". The extract "derived from" a *Flavobacterium* strain may be derived from not only a cell culture or whole cell broth but also a filtrate, supernatant, extract or cell fraction derived from said whole cell broth or cell culture.

In a particular embodiment, the strain of *Flavobacterium* spp. may have the following characteristics:

(A) a 16S rRNA gene sequence comprising the forward sequence having at least 99% identity to the sequence set forth in SEQ ID N0:3 and a reverse sequence having at least 99% identity to the sequence set forth in SEQ ID N0:4 and a consensus sequence having at least 99% identity to the sequence set forth in SEQ ID N0:5;

(B) pesticidal activity;

(C) growth modulating and particularly growth promoting activity;

(D) produces a pesticidal compound having the following properties: (1) has a molecular weight of about 150-195 as determined by Liquid Chromatography/Mass Spectroscopy (LC/MS); (2) has $^1$H NMR values of δ 7.60, 7.52, 6.83, 6.68, 2.74, 1.14 and has $^{13}$C NMR values of 203.96, 161.90, 145.11, 131.78, 131.78, 127.28, 123.83, 117.24, 117.24, 34.52, 8.89; (3) has an High Pressure Liquid Chromatography (HPLC) retention time of about 8-14 minutes, on a reversed phase C-18 HPLC (Phenomenex, Luna 5µ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm;

(E) is non-pathogenic to vertebrate animals;

(F) is susceptible to tetracycline, erythromycin, streptomycin, penicillin, ampicillin, Oxytetracycline, Chloramphenicol, Ciprofloxacin, Gentamicin, Piperacillin, Imipenem and Sulphamethoxazole-Trimethoprim.

In particular, the *Flavobacterium* species is a *Flavobacterium* strain having the identifying characteristics of *Flavobacterium* sp. H492 (NRRL Accession No. B-50584), or a mutant strain generated from said strain, which in a particular embodiment has identifying characteristics of said strain. Therefore, in a related aspect, said *Flavobacterium* strain is provided.

Also provided is a substantially pure culture or whole cell broth comprising or cell fraction, filtrate, supernatant, compound (e.g., metabolite) and/or extract derived from this *Flavobacterium* strain. Further provided is a composition comprising said substantially pure culture or whole cell broth comprising or cell fraction, filtrate, supernatant, compound (e.g., metabolite) and/or extract derived from this *Flavobacterium* strain and a carrier, diluent, surfactant a carrier, surfactant or adjuvant.

The compound used in the methods and compositions and combinations may be a compound that (a) has pesticidal activity; (b) has a molecular weight of about 150-195 as determined by Liquid Chromatography/Mass Spectroscopy (LC/MS) and (c) has an High Pressure Liquid Chromatography (HPLC) retention time of about 8-14 minutes on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm; and (d) is optionally obtainable from a *Flavobacterium* species. The compound in one embodiment may be a polyketide.

In a particular embodiment, the compound may be derived from *Flavobacterium* and has a hydroxylated aromatic polyketide structure comprising at least one ketone moiety, at least one 6 membered aromatic ring, at least one α,β unsaturated moiety, at least one hydroxyl group, at least one methylene group and at least one methyl group; a molecular weight from 150 to about 195 in the core structure; at least 9 carbons and at least 2 oxygens.

In one specific embodiment, the compound (a) is obtainable from a *Flavobacterium* species; (b) is toxic to a pest; (c) has a molecular weight of about 150-195 and more particularly, 176 as determined by Liquid Chromatography/Mass Spectroscopy (LC/MS); (d) has $^1H$ NMR values of δ 7.60, 7.52, 6.83, 6.68, 2.74, 1.14 and has $^{13}C$ NMR values of 203.96, 161.90, 145.11, 131.78, 131.78, 127.28, 123.83, 117.24, 117.24, 34.52, 8.89; (e) has an High Pressure Liquid Chromatography (HPLC) retention time of about 8-14 minutes, more specifically about 11 minutes and even more specifically about 11.31 min on a reversed phase C-18 HPLC (Phenomenex, Luna 5μ, C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm.

In a more particular embodiment, provided are compounds including but not limited to:

(A) a compound having the structure ##STR001##

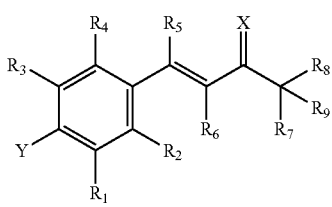

STR001## or a pesticidally acceptable salt or steriosomers thereof, wherein Y is OH, SH, NR, OR, SR, R wherein —R is lower chain alkyl containing 1, 2, 3, 4, 5, 6, 7, 8 or 9 alkyl moieties, aryl or arylalkyl moiety, substituted lower alkyl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; X is O, NH, NR or S; $R_1$, $R_2$, $R_3$, $R_4$, $R_5$, $R_6$, $R_7$, $R_8$, $R_9$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(B) a compound having the structure ##STR001a##

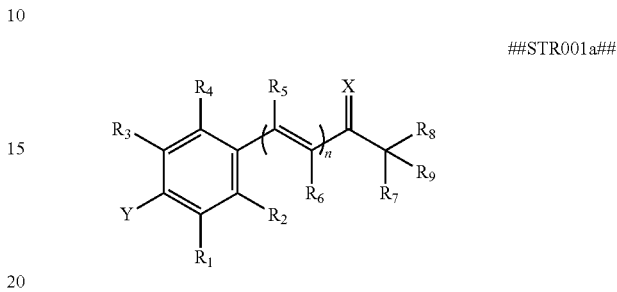

STR001a## or a pesticidally acceptable salt or steriosomers thereof, wherein Y is OH, SH, NR, OR, SR, R wherein —R is lower chain alkyl containing 1, 2, 3, 4, 5, 6, 7, 8 or 9 alkyl moieties, aryl or arylalkyl moiety, substituted lower alkyl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; X is O, NH, NR or S; n is 0, 1, 2, 3, 4, 5, 6, 7, 8 or 9; $R_1$, $R_2$, $R_3$, $R_4$, $R_5$, $R_6$, $R_7$, $R_8$, $R_9$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(C) a compound having the structure ##STR001b##

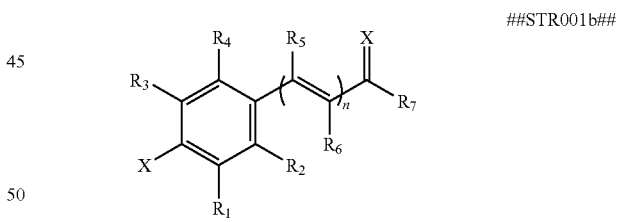

STR001b## or a pesticidally acceptable salt or steriosomers thereof, wherein Y is OH, SH, NR, OR, SR, R wherein —R is lower chain alkyl containing 1, 2, 3, 4, 5, 6, 7, 8 or 9 alkyl moieties, aryl or arylalkyl moiety, substituted lower alkyl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; X is O, NH, NR or S; n is 0, 1, 2, 3, 4, 5, 6, 7, 8 or 9; $R_1$, $R_2$, $R_3$, $R_4$, $R_5$, $R_6$, $R_7$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(D) a compound having the structure ##STR001c##

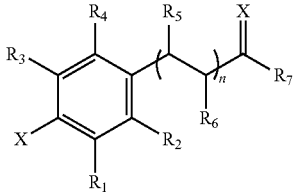

STR001c## or a pesticidally acceptable salt or steriosomers thereof, wherein Y is OH, SH, NR, OR, SR, R wherein —R is lower chain alkyl containing 1, 2, 3, 4, 5, 6, 7, 8 or 9 alkyl moieties, aryl or arylalkyl moiety, substituted lower alkyl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; X is O, NH, NR or S; n is 0, 1, 2, 3, 4, 5, 6, 7, 8 or 9; $R_1$, $R_2$, $R_3$, $R_4$, $R_5$, $R_6$, $R_7$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(E) a compound having the structure ##STR001c##

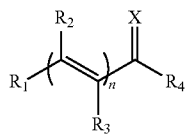

STR001d## or a pesticidally acceptable salt or steriosomers thereof, wherein X is O, NH, NR or S; n is 0, 1, 2, 3, 4, 5, 6, 7, 8 or 9; $R_1$, $R_2$, $R_3$, $R_4$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

wherein when R4 is an unsubstituted aryl, R1 is not ethyl or aryl and wherein when R4 is a substituted alkenyl substituted with aryl or substituted aryl, R1 is not a substituted alkenyl substituted with an aryl or substituted aryl.

In a more particular embodiment, the compound is the $C_6$-$C_5$ aromatic polyketide, 1-(4-hydroxyphenyl) pent-1-en-3-one (1).

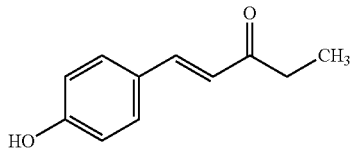

In a particular embodiment, the compound may be (E)-4-phenylbut-3-en-2-one, Benzalacetophenone, (E)-4-(2-hydroxyphenyl)but-3-en-2-one, (3E,5E)-6-phenylhexa-3,5-dien-2-one, (2E,4E)-1,5-diphenylpenta-2,4-dien-1-one, (E)-1-(2-hydroxyphenyl)pent-1-en-3-one, (E)-3-(2-hydroxyphenyl)-1-phenylprop-2-en-1-one, (E)-1-(2-hydroxyphenyl)-5-methylhex-1-en-3-one, (E)-3-(4-hydroxyphenyl)-1-phenylprop-2-en-1-one, (E)-1-(4-hydroxyphenyl)-5-methylhex-1-en-3-one, (E)-4-(3-hydroxyphenyl)but-3-en-2-one, (E)-4-(2-hydroxyphenyl) but-3-en-2-one, 2-(2'-phenyl-2-oxoethoxy)benzaldehyde, (E)-4-(2-hydroxyphenyl)-3-methylbut-3-en-2-one, (E)-1-phenylpent-2-en-1-one, (3E,7Z)-deca-3,7-dien-2-one, (E)-4-(3-hydroxyphenyl)but-3-en-2-one, (1E,4E)-1,5-bis(3-hydroxyphenyl)penta-1,4-dien-3-one, (E)-1,4-diphenylbut-2-en-1-one, (E)-1-(4-hydroxyphenyl)-4-phenylbut-2-en-1-one, (1E,4E)-1,5-bis(3-hydroxyphenyl)-2-methylpenta-1,4-dien-3-one, (E)-3-(3-hydroxyphenyl)-1-phenylprop-2-en-1-one, (E)-1-phenylpent-1-en-3-one, (E)-4-(4-hydroxyphenyl)-3-methylbut-3-en-2-one, (E)-5-methyl-1-phenylhex-1-en-3-one, 2-bromo-1-phenylethanone, (E)-1-(3-hydroxyphenyl)-5-methylhex-1-en-3-one, (E)-4-(4-hydroxyphenyl)but-3-en-2-on, 3-hydroxybenzaldehyde, 4-hydroxybenzaldehyde, 2-hydroxybenzaldehyde, benzaldehyde, gamma-dodecalactone, gamma-octalactone, 2-octanone, 2-heptanone, 2-undecanone, cis-4-heptenal, 4-methyl-2-pentanone, isobutyraldehyde, (E)-4-phenylbut-2-enal, (E)-4-(4-hydroxyphenyl) but-2-enal, (E)-4-(3-hydroxyphenyl) but-2-enal, (E)-4-(2-hydroxyphenyl) but-2-enal, 3-phenylpropanal, 3-(4-hydroxyphenyl)propanal, 3-(3-hydroxyphenyl)propanal, 3-(2-hydroxyphenyl)propanal, 2-phenylacetaldehyde, 2-(4-hydroxyphenyl)acetaldehyde, 2-(3-hydroxyphenyl)acetaldehyde, 2-(2-hydroxyphenyl)acetaldehyde, cinnamaldehyde, (E)-3-(4-hydroxyphenyl)acrylaldehyde, (E)-3-(3-hydroxyphenyl)acrylaldehyde, (E)-3-(2-hydroxyphenyl)acrylaldehyde, (2E,4E)-5-phenylpenta-2,4-dienal, (2E,4E)-5-(4-hydroxyphenyl)penta-2,4-dienal, (2E,4E)-5-(3-hydroxyphenyl)penta-2,4-dienal, (2E,4E)-5-(2-hydroxyphenyl)penta-2,4-dienal, pentan-2-one, hexan-2-one, 3-methylheptan-2-one 3-methyloctan-2-one, 3-methylnonan-2-one and stereoisomers thereof (e.g., diastereoisomers, cis-trans isomers, enantiomers).

Methods of Production

As noted above, compounds or metabolites may be obtained, are obtainable or derived from an organism having the identifying characteristics of a *Flavobacterium* species, or alternatively from any other microorganism. The methods comprise cultivating these organisms and obtaining the compounds and/or compositions of the present invention by isolating these compounds from the culture of these organisms.

In particular, the organisms are cultivated in nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media may be available from commercial sources or prepared according to published compositions.

After cultivation, a substantially pure culture or whole cell broth comprising said strain, or cell fraction, supernatant, filtrate, compound (e.g., metabolite and/or extract of or derived from said *Flavobacterium* sp. may be used in formulating a pesticidal composition. Alternatively, after cultivation, the compounds and/or metabolites may be extracted from the culture broth.

The extract may be fractionated by chromatography. Chromatographic fractions may be assayed for toxic activity against, for example, free-living nematodes and plant parasitic nematodes, *M. incognita* and/or *M. hapla* using methods known in the art. This process may be repeated one or more times using the same or different chromatographic methods.

Compositions

Compositions may comprise whole broth cultures, liquid cultures, or suspensions comprising a strain from a *Flavobacterium* sp., as well as cell fractions, supernatants, filtrates or extracts derived from said strain of a *Flavobacterium* sp., or combinations of the foregoing which in particular have nematocidal activity.

The compositions set forth above can be formulated in any manner. Non-limiting formulation examples include, but are not limited to, emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), etc. In any formulation described herein, percent of the active ingredient is within a range of about 0.01% to 99.99%.

The compositions may be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower. A composition may comprise gel-encapsulated active ingredient(s). Such gel-encapsulated materials can be prepared by mixing a gel-forming agent (e.g., gelatin, cellulose, or lignin) with a culture or suspension of live or inactivated *Flavobacterium* sp., or a cell-free filtrate or cell fraction of a *Flavobacterium* sp. culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) sorbitan monolaurate. The concentration of surfactants may range between about 0.1-35% of the total formulation; a preferred range is about 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition set forth above may be combined with another microorganism and/or pesticide (e.g., nematicide, fungicide, insecticide). The microorganism may include, but is not limited to, an agent derived from *Bacillus* sp. (e.g., *B. firmus, B. thuringiensis, B. pumilus, B. licheniformis, B. amyloliquefaciens, B. subtilis*), *Paecilomyces* sp. (*P. lilacinus*), *Pasteuria* sp. (*P. penetrans*), *Pseudomonas* sp., *Brevabacillus* sp., *Lecanicillium* sp., *Ampelomyces* sp., *Pseudozyma* sp., *Streptomyces* sp. (*S. bikiniensis, S. costaricanus, S. avermitilis*), *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorosplrnium* sp, *Neobulgaria* sp, *Daldinia* sp, *Aspergillus* sp, *Chaetomium* sp, *Lysobacter* sp, *Lachnum papyraceum, Verticillium suchlasporium, Arthrobotrys oligospora, Pochonia chlamydosporia* (synonym: *Verticillium chlamydosporium*), *Hirsutella minnesotensis, Hirsutella rhossiliensis, Pleurotus ostreatus, Omphalotus olearius, Lampteromyces japonicas, Brevudimonas* sp., *Muscodor* sp.

The pesticide may be a natural oil, oil product or chemical pesticide. In particular, the agent may be a natural oil or oil-product having nematicidal, fungicidal and/or insecticidal activity (e.g., paraffinic oil, tea tree oil, lemongrass oil, clove oil, cinnamon oil, citrus oil including but not limited to bitter orange, orange, lemon; rosemary oil, pyrethrum, allspice, bergamot, blue gum, camomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, saponins).

The chemical pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a *Reynoutria* extract. The chemical pesticide can also be a multi-site non-inorganic, chemical fungicide selected from the group consisting of chloronitrile, quinoxaline, sulphamide, phosphonate, phosphite, dithiocarbamate, chloralkythios, phenylpyridin-amine, cyano-acetamide oxime.

Nematicides may include but are not limited to avermectin nematicides (e.g., abamectin); botanical nematicides (e.g., carvacrol); carbamate nematicides (e.g., benomyl carbofuran, carbosulfan, cloethocarb); oxime carbamate nematicides (e.g., alanycarb, aldicarb aldoxycarb, oxamyl tirpate); fumigant nematicides (e.g., carbon disulfide, cyanogen, 1,2-dichloropropane, 1,3-dichloropropene, dithioether, methyl bromide, methyl iodide, sodium tetrathiocarbonate); organophosphorus nematicides, which includes but are not limited to organophosphate nematicides (e.g., diamidafos, fenamiphos, fosthietan, phosphamidon);

organothiophosphate nematicides (e.g., cadusafos, chlorpyrifos, dichlofenthion dimethoate ethoprophos, fensulfothion, fosthiazate, heterophos, isamidofos, isazofos, phorate, phosphocarb, terbufos, thionazin, triazophos); phosphonothioate nematicides (e.g., imicyafos, mecarphon); unclassified nematicides (e.g., acetoprole, benclothiaz, chloropicrin, dazomet, DBCP, DCIP, fluensulfone, furfural, metam, methyl isothiocyanate, xylenols, spirotetramat)

The composition can also be used in combination with other growth promoting agents such as synthetic or organic fertilizers (e.g., di-ammonium phosphate in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and, growth promoting microbes, such as *Bacillus* spp., *Pseudomonads, Rhizobia, Trichoderma* spp.

Furthermore, the composition can be used in combination with seed-coating agents. Such seed coating agents include, but are not limited to, ethylene glycol, carboxymethyl cellulose, methyl cellulose, polyethylene glycol, chitosan, carboxymethyl chitosan, peat moss, resins and waxes or chemical fungicides or bactericides with either single site, multisite or unknown mode of action. The compositions may be applied using methods known in the art. Specifically, these compositions may be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include, but are not limited to, harvested material, and vegetative and generative propagation material, for example cuttings, tubers, rhizomes, offshoots and seeds. Plants that may be treated include but are not limited to: (A) Major edible food crops, which include but are not limited to (1) Cereals, (e.g., African rice, barley, durum wheat, einkorn wheat, emmer wheat, finger millet, foxtail millet, hairy crabgrass, Indian barnyard millet, Japanese barnyard millet, maize, nance, oat, pearl millet, proso millet, rice, rye, sorghum, *Sorghum* spp., rye, spelt wheat); (2) Fruits (e.g., abiu, acerola, achacha, African mangosteen, alpine currant, ambarella, American gooseberry, American persimmon, apple, apricot, arazá, Asian palmyra palm, Asian pear, atemoya, Australian desert raisin, avocado, azarole, babaco, bael, banana, Barbados gooseberry, bergamot, betel nut, bignay, bilberry, bilimbi, binjai, biriba, bitter orange, black chokeberry, black mulberry, black sapote, blackberry, blueberried honeysuckle, borojo, breadfruit, murmese grape, button mangosteen, cacao, calamondin, canistel, cantaloupe, cape gooseberry, cashew nut, cassabanana, cempedak, charichuelo, cherimoya, cherry, cherry of the Rio Grande, cherry plum, Chinese hawthorn, Chinese white pear, chokeberry, citron, cocona, coconut, cocoplum, coffee, coffee Arabica, coffee robusta, Costa Rica pitahaya, currants, custard apple, date, date-plum, dog rose, dragonfruit, durian, elderberry, elephant apple, Ethiopian eggplant, European nettle tree, European wild apple, feijoa, fig, gac, genipapo, giant granadilla, gooseberry, goumi, grape, grapefruit, great morinda, greengage, guava, hardy kiwi, hog plum, horned melon, horse mango, Indian fig, Indian jujube, jabuticaba, jackberry, jackfruit, Japanese persimmon, Japanese wineberry, jocote, jujube, kaffir lime, karanda, kei apple, kepel apple, key lime, kitembilla, kiwi fruit, korlan, kubal vine, kuwini mango, kwai muk, langsat, large cranberry, lemon, Liberian coffee, longan, loquat, lychee, malay apple, mamey sapote, mammee apple, mango, mangosteen, maprang, marang, medlar, melon, Mirabelle plum, miracle fruit, monkey jack, moriche palm, mountain papaya, mountain soursop, mulberry, naranjilla, natal plum, northern highbush blueberry, olive, otaheite gooseberry, oval kumquat, papaya, para guava, passionfruit, pawpaw, peach, peach-palm, pear, pepino, pineapple, pitomba *Eugenia luschnathiana*, pitomba *talisia esculenta*, plantain, plum, pomegranate, pomelo, pulasan, purple chokeberry, quince, rambutan, ramontchi, raspberry, red chokeberry, red currant, red mulberry, red-fruited strawberry guava, rhubarb, rose apple, roselle, safou, salak, salmonberry, santol, sapodilla, satsuma, seagrape, soncoya, sour cherry, soursop, Spanish lime, Spanish tamarind, star apple, starfruit, strawberry, strawberry guava, strawberry tree, sugar apple, Surinam cherry, sweet briar, sweet granadilla, sweet lime, tamarillo, tamarind, tangerine, tomatillo, tucuma palm, *Vaccinium* spp., velvet apple, wampee, watermelon, watery rose apple, wax apple, white currant, white mulberry, white sapote, white star apple, wolfberry (*Lyceum barbarum, L. chinense*), yellow mombin, yellow pitaya, yellow-fruited strawberry, guava, (3) Vegetables (e.g., ackee, agate, air potato, *Amaranthus* spp., American groundnut, antroewa, armenian cucumber, arracacha, arrowleaf elephant ear, arrowroot, artichoke, ash gourd, asparagus, avocado, azuki bean, bambara groundnut, bamboo, banana, barbados gooseberry, beet, beet root, bitter gourd, bitter vetch, bitterleaf, black mustard, black radish, black salsify, blanched celery, breadfruit, broad bean, broccoli, brussels sprout, Buck's horn plantain, buttercup squash, butternut squash, cabbage, caigua, calabash, caraway seeds, carob, carrot, cassabanana, cassava, catjang, cauliflower, celeriac, celery, celtuce, chard, chayote, chickpea, chicory, chilacayote, chili pepper (*Capsicum annuum, C. baccatum, C. chinense, C. frutescens, C. pubescens*), Chinese cabbage, Chinese water chestnut, Chinese yam, chives, chufa sedge, cole crops, common bean, common purslane, corn salad, cowpea, cress, cucumber, cushaw pumpkin, drumstick tree, eddoe, eggplant, elephant foot yam, elephant garlic, endive, enset, Ethiopian eggplant, Florence fennel, fluted gourd, gac, garden rocket, garlic, geocarpa groundnut, good king henry, grass pea, groundut, guar bean, horse gram, horseradish, hyacinth bean, iceplant, Indian fig, Indian spinach, ivy gourd, Jerusalem artichoke, jicama, jute, kale, kohlrabi, konjac, kurrat, leek, lentil, lettuce, Lima bean, lotus, luffa, maca, maize, mangel-wurzel, mashua, moso bamboo, moth bean, mung bean, napa cabbage, neem, oca, okra, oldham's bamboo, olive, onion, parsnip, pea, pigeon pea, plantain, pointed gourd, potato, pumpkins, squashes, quinoa, radish, rapeseed, red amaranth, rhubarb, ribbed gourd, rice bean, root parsley, runner bean, rutabaga, sago palm, salsify, scallion, sea kale, shallot, snake gourd, snow pea, sorrel, soybean, spilanthes, spinach, spinach beet, sweet potato, taro, tarwi, teasle gourd, tepary bean, tinda, tomato, tuberous pea, turnip, turnip-rooted chervil, urad bean, water caltrop *trapa bicornis*, water caltrop trapa natans, water morning slory, watercress, welsh onion, west African okra, west Indian gherkin, white goosefoot, white yam, winged bean, winter purslane, yacón, yam, yard-long bean, zucchinietables); (4) Food crops (e.g., abiu, acerola, achacha, ackee, African mangosteen, African rice, agate, air potato, alpine currant, *Amaranthus* app., Ambarrella, American gooseberry, American groundnut, American persimmon, antroewa, apple, apricot, arazá, Armenian cucumber, arracacha, arrowleaf elephant ear, arrowroot, artichoke, ash gourd, Asian palmyra palm, Asian pear, asparagus, atemoya, Australian desert raisin, avocado, azarole, azuki bean, babaco, bael, bambara groundnut, bamboo, banana, barbados gooseberry, barley, beet, beetroot, bergamot, betel nut, bignay, bilberry, bilimbi, binjai, biriba, bitter gourd, bitter orange, bitter vetch, bitterleaf, black chokeberry, black currant, black mulberry, black mustard, black radish, black salsify, black sapote, blackberry, blanched celery, blue-berried honeysuckle, borojo, breadfruit, broad bean, broccoli, Brussels sprout, Buck's horn plantain, buckwheat, Burmese grape, buttercup squash, butternut squash, button mangosteen, cabbage, cacao, caigua, calabash, calamondin, canistel, cantaloupe, cape gooseberry, caraway seeds, carob, carrot, cashew nut, cassava, catjang, cauliflower, celeriac, celery, celtuce, cempedak, chard, charichuelo, chayote, cherimoya, cherry, cherry of the Rio Grande, cherry plum, chickpea, chicory, chilacayote, chili pepper (*Capsicum annuum, C. baccatum, C. chinense, C. frutescens, C. pubescens*), Chinese cabbage, Chinese hawthorn, Chinese water chestnut, Chinese white pear, Chinese yam, chives, chokeberry, chufa sedge, citron, cocona, coconut, cocoplum, coffee, coffee (*Arabica* and *Robusta* types), cole crops, common bean, common purslane, corn salad, Costa Rica pitahaya, cowpea, cress, cucumber, currants, cushaw pumpkin, custard apple, date, date-plum, dog rose, dragonfruit, drumstick tree, durian, durum wheat, eddoe, eggplant, einkorn wheat, elderberry, elephant apple, elephant foot yam, elephant garlic, emmer wheat, endive, enset, Ethiopian eggplant, European nettle tree, European wild apple, feijoa, fig, finger millet, florence fennel, fluted gourd, foxtail millet, gac, garden rocket, garlic, genipapo, geocarpa groundut, giant granadilla, good king henry, gooseberry, goumi, grape, grapefruit, grass pea, great morinda, greengage, groundnut, grumichama, guar bean, guava, hairy crabgrass, hardy kiwi, hog plum, horned melon, horse gram, horse mango, horseradish, hyacinth bean, iceplant, Indian barnyard millet, Indian fig, Indian jujube, Indian spinach, ivy gourd, jabuticaba, jackalberry, jackfruit, jambul, Japanese barnyard millet, Japanese persimmon, Japanese wineberry, Jerusalem artichoke, jocote, jujube, jute, kaffir lime, kale, karanda, kei apple, kepel apple, key lime, kitembilla, kiwifruit, kohlrabi, konjac, korlan, kubal vine, kurrat, kuwini mango, kwai muk, langsat, large cranberry, leek, lemon, lentil, lettuce, Liberian coffee, lima bean, longan, loquat, lotus, luffa, lychee, maca, maize, malay apple, mamey saptoe, mammee apple, mangelwurzel, mango, mangosteen, maprang, marang, mashua, medlar, melon, Mirabelle plum, miracle fruit, monk fruit, monkey jack, moriche palm, moso bamboo, moth bean, mountain papaya, mountain soursop, mulberry, mung bean, mushrooms, nance, napa cabbage, naranjilla, natal plum, neem, northern highbush blueberry, oat, oca, oil palm, okra, oldman's bamboo, olive, onion, orange, otaheite gooseberry, oval kumquat, papaya, para guava, parsnip, passionfruit, pawpaw, pea, peach, peach-palm, pear, pearl millet, pepino, pigeon pea, pineapple, Pitomba (*Eugenia luschnathiana, Talisia esculenta*), plantain, plum, pointed gourd, pomegranate, pomelo, potato, proso millet, pulasan, pumpkins and squashes, purple chokeberry, quince, quinoa, radish, rambutan, ramontchi, rapeseed, raspberry, red amaranth, red chokeberry, red currant, red mulberry, red-fruited strawberry guava, rhubarb, ribbed gourd, rice, rice bean, root parsley, rose apple, roselle, runner bean, rutabaga, rye, safou, sago palm, salak, salmonberry, salsify, santol, sapodilla, Satsuma, scallion, sea kale, seagrape, shallot, snake gourd, snow pea, soncoya, sorghum, *Sorghum* spp., sorrel, sour cherry, soursop, soybean, Spanish lime, Spanish tamarind, spelt wheat, spilanthes, spinach, spinach beet, star apple, starfruit, strawberry, strawberry guava, strawberry tree, sugar apple, sugar beet, sugarcane, surinam cherry, sweet briar, sweet granadilla, sweet lime, sweet potato, tamarillo, tamarind, tangerine, taro, tarwi, teasle gourd, tef, tepary bean, tinda, tomatillo, tomato, tuberous pea, tucuma palm, turnip, turnip-rooted chervil, urad bean, *Vaccinium* spp., velvet apple, wampee, water caltrop (*Trapa bicornis, T. natans*), water morning glory, watercress, watermelon, watery rose apple, wax apple, welsh onion, west African okra, west Indian gherkin, wheat, white currant, white goosefoot, white mulberry, white sapote, white star apple, white yam, winged bean, winter purslane, wolfberry (*Lycium barbarum, L. chinense*), yacón, yam, yangmei, yard-long bean, yellow mombin, yellow pitaya, yellow-fruited strawberry guava, zucchini; (B) Other edible crops, which includes but is not limited to (1) Herbs (e.g., *Absinthium*, alexanders, basil, bay laurel, betel nut, camomile, chervil, chili pepper (*Capsicum annuum, C. baccatum, C. chinense, C. frutescens, C. pubescens*), chili peppers, chives, cicely, common rue, common thyme, coriander, cress, culantro, curly leaf parsley, dill, epazote, fennel, flat leaf parsley, ginseng, gray santolina, herb hyssop, holy basil, hop, jasmine, kaffir lime, lavender, lemon balm, lemon basil, lemon grass, lovage, marjoram, mint, oregano, parsley, peppermint, perilla, pot marigold, rooibos, rosemary, sage, shiny-leaft buckthorn, sorrel, spearmint, summer savory, tarragon, Thai basil, valerian, watercress, wild betel, winter savory, yerba mate); (2) Spices (e.g., ajowan, allspice, anise, bay laurel, black cardamom, black mustard, black pepper, caper, caraway seeds, cardamom, chili pepper (*Capsicum annuum, C. baccatum, C. chinense, C. frutescens, C. pubescens*), chili peppers, cinnamon, clove, common juniper, coriander, cumin, fennel, fenugreek, garlic, ginger, kaffir lime, liquorice, nutmeg, oregano, pandan, parsley, saffron, star anise, turmeric, vanilla, white mustard); (2) Medicinal plants (e.g., *absinthium*, alfalfa, aloe vera, anise, artichoke, basil, bay laurel, betel leaf, betel nut, bilberry, black cardamom, black mustard, black pepper, blue gum, borojó, camomlie, caper, cardamom, castor bean, chili peppers, Chinese yam, chives, cola nut, common jasmine, common lavender, common myrrh, common rue, cilantro, cumin, dill, dog rose, epazote, fennel, fenugreek, gac, garlic, ginger, gray santolina, gum Arabic, herb hyssop, holy basil, horseradish, incense tree, lavender, lemon grass, liquorice, lovage, marijuana, marjoram, monk fruit, neem, opium, oregano, peppermint, pot marigold, quinine, red acacia, red currant, rooibos, safflower, sage, shiny-leaf buckthorn, sorrel, spilanthes, star anise, tarragon, tea, turmeric, valerian, velvet bean, watercress, white mustard, white sapote, wild betel, wolfberry (*Lycium barbarum, L. chinense*), yerba mate); (3) Stimulants (e.g., betel leaf, betel nut, cacao, chili pepper (*Capsicum annuum, C. baccatum, C. chinense, C. frutescens, C. pubescens*), chili peppers, coffee, coffee (*Arabica, Robusta*), cola nut, khat, Liberian coffee, tea, tobacco, wild betel, yerba mate); (4) Nuts (e.g., almond, betel nut, Brazil nut, cashew nut, chestnut, Chinese water chestnut, coconut, cola nut, common walnut, groundnut, hazelnut, Japanese stone oak, macadamia, nutmeg, paradise nut, pecan nut, pistachio nut, walnut); (5) Edible seeds (e.g., black pepper, Brazil nut, chilacayote, cola nut, fluted gourd, lotus, opium, quinoa, sesame, sunflower, water caltrop (*Trapa bicornis, T. natans*); (6) Vegetable oils (e.g., black mustard, camelina, castor bean, coconut, cotton, linseed, maize, neem, niger seed, oil palm, olive, opium, rapeseed, safflower, sesame, soybean, sunflower, tung tree, turnip); (7) Sugar crops (e.g., Asian palmyra palm, silver date palm, sorghum, sugar beet, sugarcane); (8) Pseudocereals (e.g., *Amaranthus* spp., buckwheat, quinoa, red amaranth); (9) Aphrodisiacs (e.g., borojó, celery, durian, garden rocket, ginseng, maca, red acacia, velvet bean); (C) Non food categories, including but not limited to (1) forage and dodder crops (e.g., agate, alfalfa, beet, broad bean, camelina, catjang, grass pea, guar bean, horse gram, Indian barnyard millet, Japanese barnyard millet, lespedeza, lupine, maize, mangel-wurzel, mulberry, niger seed, rapeseed, rice bean, rye); (2) Fiber crops (e.g., coconut, cotton, fique, hemp, henequen, jute, kapok, kenaf, linseed, manila hemp, New Zealand flax, ramie, roselle, sisal, white mulberry); (3) Energy crops (e.g., blue gum, camelina, cassava, maize, rapeseed, sorghum, soybean, Sudan grass, sugar beet, sugarcane, wheat); (4) Alcohol production, (e.g., barley, plum, potato, sugarcane, wheat, sorghum); (5) Dye crops (e.g., chay root, henna, indigo, old fustic, safflower, saffron, turmeric); (6) Essential oils (e.g., allspice, bergamot, bitter orange, blue gum, camomile, citronella, clove, common jasmine, common juniper, common lavender, common myrrh, field mint, freesia, gray santolina, herb hyssop, holy basil, incense tree, jasmine, lavender, lemon, marigold, mint, orange, peppermint, pot marigold, spearmint, ylang-ylang tree); (6) Green manures (e.g., alfalfa, clover, lacy Phacelia, ii hemp, trefoil, velvet bean, vetch); (7) Erosion prevention (e.g., bamboo, cocoplum; (8) Soil improvement (e.g., lupine, vetch); (9) Cover crops (e.g., Alfalfa, lacy Phacelia, radish); (10) Botanical pesticides (e.g., jicama, marigold, neem, pyrethrum); (11) Cut flowers (e.g., carnation, chrysanthemum, daffodil, dahlia, freesia, gerbera, marigold, rose, sunflower, tulip); (12) Ornamental plants (e.g., African mangosteen, aloe vera, alpine currant, aster, black chokeberry, breadfruit, calamondin, carnation, cassabanana, castor bean, cherry plum, chokeberry, chrysanthemum, cocoplum, common lavender, crocus, daffodil, dahlia, freesia, gerbera, hyacinth, Japanese stone oak, Jasmine, lacy Phacelia, lotus, lupine, marigold, New Zealand flax, opium, purple chokeberry, ramie, red chokeberry, rose, sunflower, tulip, white mulberry); (D) Trees which include but are not limited to abelia, almond, apple, apricot, arborvitae nigra american, arborvitae, ash, aspen, azalea, baldcypress, beautybush, beech, birch, black tupelo, blackberry, blueberry, boxwood, buckeye, butterfly bush, butternut, camellia, catalpa, cedar, cherry, chestnut, coffeetree, crab trees, crabapple, crapemyrtle, cypress, dogwood, douglasfir, ebony, elder American, elm, fir, forsythia, ginkgo, goldenraintree, hackberry, hawthorn, hazelnut, hemlock, hickory, holly, honeylocust, horsechestnut, hydrangea, juniper, lilac, linden, magnolia, maple, mockorange, mountainash, oak, olive, peach, pear, pecan, pine, pistache, planetree, plum, poplar, pivet, raspberry, redbud, redcedar, redwood, rhododendron, rose-of-sharon, sassafras, sequoia, serviceberry, smoketree, soapberry, sourwood, spruce, strawberry tree, sweetshrub, sycamore, tuliptree, viburnum, walnut, weigela, willow, winterberry, witchhazel, zelkova; (E) Turf which includes but is not limited to Kentucky bluegrass, tall fescue, Bermuda grass, zoysia grass, perennial ryegrass, fine fescues (e.g.; creeping red, chewings, hard, or sheep fescue).

Treatment of the plants and plant parts with the compositions set forth above may be carried out directly or by allowing the compositions to act on their surroundings, habitat or storage space by, for example, immersion, spraying, evaporation, fogging, scattering, painting on, injecting.

In the case that the composition is applied to a seed, the composition may be applied to the seed as one or more coats prior to planting the seed using one or more coats using methods known in the art.

Uses

The compositions, cultures, supernatants, metabolites and pesticidal compounds set forth above may be used as pesticides and in particular, may be used as insecticides and nematicides, alone or in combination with one or more pesticidal substances set forth above and applied to plants, plant parts, substrate for growing plants or seeds set forth above Specifically, nematodes that may be controlled using the method set forth above include but are not limited to parasitic nematodes such as root-knot, reniform, cyst, and lesion nematodes, including but not limited to *Meloidogyne* sp., *Tylenchorhynchus* sp., *Belonolaimus* sp., *Hoplolaimus* sp., *Helicotylenchus* sp., *Pratylenchus* sp., *Rotylenchulus* sp., *Heterodera* sp., *Globodera* sp., *Trichodorus* sp., *Paratrichodorus* sp., *Xiphinema* sp., and *Criconema* sp In particular, the parasitic nematodes may include but are not limited to seed gall nematodes (*Afrina wevelli*), bentgrass nematodes (*Anguina agrostis*), shoot gall nematodes (*Anguina* spp.), seed gall nematodes (*Anguina* spp., *A. amsinckiae, A. balsamophila; A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf (or fern, or spring crimp, or strawberry foliar, or strawberry nematodes, or summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides composticola*), *Atalodera* spp. (*Atalodera lonicerae, Atalodera ucri*), spine nematodes (*Bakernema variabile*), sting nematodes (*Belonolaimus* spp., *B. gracilis, B. longicaudatus*), pine wood nematodes (*Bursaphalenchus* spp., *B. xylophilus, B. mucronatus*), sessile nematodes (*Cacopaurus* spp., *C. epacris, C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae, C. decalineatum, C. spinalineatum*), ring nematodes (*Criconemella axeste, C. curvata, C. macrodora, C. parva*), ring nematodes (*Criconemoides* spp., *C. citri, C. simile*), spine nematodes (*Crossonema fimbriatum*), eucalypt cystoid nematodes (*Cryphodera eucalypti*), bud, stem and bulb nematodes (*Ditylenchus* spp., *D. angustus, D. dipsaci, D. destructor, D. intermedius*), Mushroom spawn nematodes (*D. myceliophagus*), awl nematodes (*Dolichodorus* spp., *D. heterocephalus, D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenettle cyst nematodes (*G. tabacum virginiae*), pin nematodes (*Gracilacus* spp., *G. idalimus*), spiral nematodes (*Helicotylenchus* spp., *H. africanus, H. digonicus, H. dihystera, H. erythrinae, H. multicinctus, H. paragirus, H. pseudorobustus, H. solani, H. spicaudatus*), sheathoid nematodes (*Hemicriconemoides* spp., *H. biformis, H. cali-*

*fornianus, H. chitwoodi, H. fioridensis, H. wessoni*), sheath nematodes (*Hemicycliophora* spp., *H. arenaria, H. biosphaera, H. megalodiscus, H. parvana, H. poranga, H. sheri, H. similis, H. striatula*), cyst nematodes (*Heterodera* spp.), almond cyst nematodes (*H. amygdali*), oat (or cereal) cyst nematodes (*H. avenae*), Cajanus (or pigeon pea) cyst nematodes (*H. cajani*), Bermuda grass (or heart-shaped, or Valentine) cyst nematodes (*H. cardiolata*), carrot cyst nematodes (*H. carotae*), cabbage cyst nematodes or *brassica* root eelworm (*H. cruciferae*), nutgrass (or sedge) cyst nematodes (*H. cyperi*), Japanese cyst nematodes (*H. elachista*), fig (or ficus, or rubber) cyst nematodes (*H. fici*), galeopsis cyst nematodes (*H. galeopsidis*), soybean cyst nematodes (*H. glycines*), alfalfa root (or pea cyst) nematodes (*H. goettingiana*), buckwheat cyst nematodes (*H. graduni*), barley cyst nematodes (*H. hordecalis*), hop cyst nematodes (*H. humuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), rumex cyst nemtodes (*H. rumicis*), sugar beet cyst nematodes (*H. schachtii*), willow cyst nematodes (*H. salixophila*), knawel cyst nematodes (*H. scleranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli, H. caudacrena, H. gracilis, H. oryzae*), lance nematodes (*Hoplolaimus* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Longidorus* spp., *L. africanus, L. sylphus*), ring nematodes (*Macroposthonia* (=*Mesocriconema*) *xenoplax*), cystoid nematodes (*Meloidodera* spp.), pine cystoid nematodes (*M. floridensis*), tadzhik cystoid nematodes (*M. tadshikistanica*), cystoid body nematodes (*Meloidoderita* spp.), stunt nematodes (*Merlinius* spp., *M. brevidens, M. conicus, M. grandis, M. microdorus*), root-knot nematodes (*Meloidogyne* spp., *M. acronea, M. arenaria, M. artiellia, M. brevicauda, M. camelliae, M. carolinensis, M. chitwoodi, M. exigua, M. graminicola, M. hapla, M. hispanica, M. incognita, M. incognita acrita, M. indica, M. inornata, M. javanica, M. kikuyuensis, M. konaensis, M. mali, M. microtyla, M. naasi, M. ovalis, M. platani, M. querciana, M. sasseri, M. tadshikistanica, M. thamesi*), knapweed nematodes (*Mesoanguina picridis*), Douglas fir nematodes (*Nacobbodera chitwoodi*), false root-knot nematodes (*Nacobbus aberrans, N. batatiformis, N. dorsalis*), sour paste nematodes (*Panagrellus redivivus*), beer nematodes (*P. silusiae*), needle nematodes (*Paralongidorus microlaimus*), spiral nematodes (*Pararotylenchus* spp.), stubby-root nematodes (*Paratrichodorus allius, P. minor, P. porosus, P. renifer*), pin nematodes (*Paratylenchus* spp., *P. baldaccii, P. bukowinensis, P. curvitatus, P. dianthus, P. elachistus, P. hamatus, P. holdemani, P. italiensis, P. lepidus, P. nanus, P. neoamplycephalus, P. similis*), lesion (or meadow) nematodes (*Pratylenchus* spp., *P. alleni, P. brachyurus, P. coffeae, P. convallariae, P. crenatus, P. flakkensis, P. goodeyi, P. hexincisus, P. leiocephalus, P. minyus, P. musicola, P. neglectus, P. penetrans, P. pratensis, P. scribneri, P. thornei, P. vulnus, P. zeae*), stem gall nematodes (*Pterotylenchus cecidogenus*), grass cyst nematodes (*Punctodera punctate*), stunt nematodes (*Quinisulcius acutus, Q. capitatus*), burrowing nematodes (*Radopholus* spp.), banana-root nematodes (*R. similis*), rice-root nematodes (*R. oryzae*), red ring (or coconut, or cocopalm) nematodes (*Rhadinaphelenchus cocophilus*), reniform nematodes (*Rotylenchulus* spp., *R. reniformis, R. parvus*), spiral nematodes (*Rotylenchus* spp., *R. buxophilus, R. christiei, R. robustus*), Thorne's lance nematodes (*R. uniformis*), *Sarisodera hydrophylla*, spiral nematodes (*Scutellonema* spp., *S. blaberum, S. brachyurum, S. bradys, S. clathricaudatum, S. christiei, S. conicephalum*), grass root-gall nematodes (*Subanguina radicicola*), round cystoid nematodes (*Thecavermiculatus andinus*), stubby-root nematodes (*Trichodorus* spp., *T. christiei, T. kurumeensis, T. pachydermis, T. primitivus*), vinegar eels (or nematodes) (*Turbatrix aceti*), stunt (or stylet) nematodes (*Tylenchorhynchus* spp., *T. agri, T. annulatus, T. aspericutis, T. claytoni, T. ebriensis, T. elegans, T. golden, T. graciliformis, T. martini, T. mashhoodi, T. microconus, T. nudus, T. oleraceae, T. penniseti, T. punensis*), citrus nematodes (*Tylenchulus semipenetrans*), dagger nematodes (*Xiphinema* spp., *X. americanum, X. bakeri, X. brasiliense, X. brevicolle, X. chambersi, X. coxi, X. diversicaudatum X. index, X. insigne, X. nigeriense, X. radicicola, X. setariae, X. vulgarae, X. vuittenezi*). In an even more particular embodiment, the nematodes, include but are not limited to *Meloidogyne incognita* (root knot nematodes), as well as *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode) and *Rotylenchulus reniformis* (reniform nematodes) (*Pratylenchus* spp.) (lesion nematodes), *Belonolaimus* sp. (sting nematode), *Hopolaimus* sp. (lance nematode), *Bursaphalenchus* spp., (e.g., pine wood nematodes), *Ditylenchus* spp. (e.g., stem nematodes).

Application of an effective pesticidal controlling amount of a substantially pure culture, or whole cell broth comprising or supernatant, filtrate, cell fraction extract or compound (e.g., metabolite) derived from a *Flavobacterium* sp. or pesticidally active compound (e.g., metabolite) derived from said whole cell broth, supernatant, filtrate or extract or application of combinations of the foregoing is provided. The substantially pure culture, whole cell broth, supernatant, filtrate, extract or compound set forth above is applied, alone or in combination with another pesticidal substance, in an effective pest control or pesticidal amount. An effective amount is defined as that quantity of microorganism cells, supernatant, whole cell broth, filtrate, cell fraction or extract, metabolite and/or compound alone or in combination with another pesticidal substance that is sufficient to modulate pest infestation. The effective rate can be affected by pest species present, stage of pest growth, pest population density, and environmental factors such as temperature, wind velocity, rain, time of day and seasonality. The amount that will be within an effective range in a particular instance can be determined by laboratory or field tests.

The said compositions, substantially pure culture, whole cell broth, supernatant, filtrate extract or compounds set forth above may be used to modulate or more particularly promote growth of plants and even more particularly, promote early root establishment of said plants.

The compositions, cultures, supernatants, a substantially pure culture, whole cell broth, supernatant, filtrate or extract derived from a *Flavobacterium* sp. or pesticidally active metabolite derived from said whole cell broth, supernatant, filtrate or extract or isolated compound produced by the

*Flavobacterium* sp. set forth above may also be used to modulate the germination of a seed(s) in a plant(s). In particular, the growth modulating effect of said compositions, a substantially pure culture, whole cell broth, supernatant, filtrate or extract derived from a *Flavobacterium* sp. or metabolite derived from said whole cell broth, supernatant, filtrate or extract or isolated compound produced by the *Flavobacterium* sp. set forth above may be determined by using methods known in the art, which may include, but is not limited to plant counts per pot, height of shoots (cm), weight of fresh shoots (g), weight of fresh root (g), plant vigor rating, root rating using a scale to evaluate root health.

The compositions, substantially pure culture, whole cell broth, supernatant, filtrate extract or compounds set forth above may modulate pest infestation by a number of mechanisms. These include but are not limited to exterminating said pests at various stages of the life cycle (eggs, larvae or adult) or affecting the motility of said pests.

The said formulated product can be used alone or simultaneously with the other component or components set forth above, such as growth promoting agents in a tank mix or in a program (sequential application called rotation) with predetermined order and application interval during the growing season. When used in a combination with the above-mentioned products, at concentration lower than recommended in the product label, the combined efficacy of the two or more products is in a preferred embodiment, higher than each individual component's effect added together. Hence, the effect is enhanced by synergism between these two (or more) products, and the risk for the development of pesticide resistance among the plant pathogenic strains is reduced.

The compositions, substantially pure culture, whole cell broth, supernatant, filtrate or extract derived from a *Flavobacterium* sp. or metabolite derived from said whole cell broth, supernatant, filtrate or extract or isolated compound produced by the *Flavobacterium* sp. set forth above may be applied by root dip at transplanting, specifically by treating a fruit or vegetable with the composition by dipping roots of the fruit or vegetable in a suspension of said composition (about 0.25 to about 1.5% and more particularly about 0.5% to about 1.0% volume by volume) prior to transplanting the fruit or vegetable into the soil.

Alternatively, the composition (may be applied by drip or other irrigation system. Specifically, the *Flavobacterium* composition t may be injected into a drip irrigation system. In a particular embodiment, the composition may be applied at a rate of about 1l to about 4 quarts per acre.

In yet another embodiment, the composition may be added as an in-furrow application. Specifically, the composition may be added as an in-furrow spray at planting using nozzles calibrated to deliver a total output of 2-6 gallons/acre. Nozzles are placed in the furrow opener on the planter so that the pesticide application and seed drop into the furrow are simultaneous. The mixtures set forth above and, where appropriate, a solid or liquid adjuvant are prepared in known manner. For example, the mixtures may be prepared by homogeneously mixing and/or grinding the active ingredients with extenders such as solvents, solid carriers and, where appropriate, surface-active compounds (surfactants). The compositions may also contain further ingredients such as stabilizers, viscosity regulators, binders, adjuvants as well as fertilizers or other active ingredients in order to obtain special effects.

EXAMPLES

The composition and methods set forth above will be further illustrated in the following, non-limiting Examples.

The examples are illustrative of various embodiments only and do not limit the claimed invention regarding the materials, conditions, weight ratios, process parameters and the like recited herein.

Example 1: Isolation and Identification of the Microbe

Isolation of the Microorganism

*Flavobacterium* sp. strain H492 was isolated from a sample of decaying plant material collected from a beach in Hawaii. The bacterium was recovered from the sample by traditional plate dilution methods as described by Lorch et al. (1995). Briefly, the sample was resuspended in sterile deionized water. Serial dilutions of the resuspended sample were prepared in sterile water. Some of these dilutions were spread onto agar plates (for example Potato Dextrose Agar) and incubated in the dark and at room temperature. After several days of incubation, colonies were recovered from the surface of the agar plate.

The isolate grows as transparent small colonies, which develop reddish to orange translucent pigment over time. The isolated bacterium is a gram-negative rod-shaped bacterium.

Identification of the Microorganism

The isolate was identified as a *Flavobacterium* species through PCR amplification and sequencing of the 16S rRNA gene using Universal Bacterial primers.

Growth from a 24 hour PDA (potato dextrose agar) plate was scrapped with a sterile loop and resuspended in DNA extraction buffer. DNA was extracted suing the MoBio Ultra Clean Microbial DNA extraction kit. DNA extract was checked for quality/quantity by running a 5 µL aliquot on a 1% agarose gel.

PCR reactions for the amplification of the 16S rRNA gene were set up by combining 2 µL of the clean DNA extract with 25 uL of GoTaq Green Mastermix, 1.5 µL forward primer (SEQ ID NO:1) and 1.5 µL reverse primer (SEQ ID NO:2). The reaction volume was made up to 50 µL using sterile nuclease-free water. The PCR reaction was ran on a thermocycler machine under the following conditions: 10 minutes at 95° C. (initial denaturing), 30 cycles of 45 seconds at 94° C., 45 seconds at 55° C. and 2 minutes at 72° C., followed by 5 minutes at 72° C. (final extension) and a final hold temperature of 10° C.

The size, quality and quantity of the PCR product was evaluated by running a 5 µL aliquot on a 1% agarose gel, and comparing the product band to a mass ladder. Excess primers, nucleotides, enzyme and template were removed from the PCR product using the MoBio PCR clean up Kit. The cleaned PCR product was subjected to direct sequencing using the primers described above. The forward (SEQ ID NO:3) and reverse sequences (SEQ ID NO:4) were aligned using the BioEdit software, and a 1416 bp consensus sequence was created.

The 16S rRNA gene consensus sequence of *Flavobacterium* sp. H492 was compared to those available sequences of representatives of the bacterial domain using BLAST. Strain H492 is closely related to members of the *Flavobacterium* genus. The closest match was to an uncultured bacterium clone (accession number FJ716008.1) with 97% similarity. Strain H492 showed <97% similarity to other known members of the *Flavobacterium* group.

Growth Conditions

Growth of *Flavobacterium* sp. H492 was assessed on potato dextrose agar at 16, 25, 30 and 37° C., on tryptic soy agar at pH 4-12 at 0.5 unit increments and on L-agar with NaCl concentrations of 0, 0.1, 0.2, 0.3, 0.4, 0.5, 0.6, 0.7, 0.8, 0.9, 1, 2, 3, 4 and 5%. Growth occurs at 25 and 30° C., but not 16 and 37° C., 0-1% NaCl and at pH 5.5-8.5 (optimum between pH 6 and 8). Positive in the flexirubin-type pigment test. Congo red is not absorbed. Oxidase positive and catalase negative. Casein, starch, CM-cellulose, pectin and DNA are hydrolyzed, but not sodium alginate and chitin. Brown diffusible pigment was not produced on L-tyrosine agar. Growth occurs on PDA, NA, TSA, R2A, Anacker and Ordal's, LB, Mueller-Hinton and Czapek Dox agars but no growth occurs on marine agar 2216, MacConkey agar and MRS agar.

Characterization

The isolate was characterized using several standard procedures including Gram staining, production of catalase and oxidase (commercial tests, Difco), and hydrolysis of casein (Atlas 2010 "Handbook of Microbiological Media", modified 5% w/v), starch (1% w/v), CM-cellulose (1% w/v), chitin (1% w/v), pectin (1% w/v) and DNA (using DNase test agar with methyl green, Difco). Congo red absorption was evaluated and production of flexirubin type pigments was assessed by observing a color shift of colonies when flooded with 20% KOH (Bernardet et al., 2002). Growth was evaluated on marine agar 2216 (Difco), nutrient agar (Difco), tryptic soy agar (Remel), R2A (Difco), Anacker and Ordal's agar (Atlas 2010 "Handbook of Microbiological Media"), MacConkey agar (Difco), MRS agar (Difco) and Czapek Dox agar (Atlas 2010 "Handbook of Microbiological Media").

Biochemical and physiological characteristics were assessed using the API ZYM and API 20NE systems (bio-Mérieux) following the manufacturer's instructions.

Enzymatic activity is detected for alkaline phosphatase, esterase C4, esterase lipase C8 (weak), leucine arylamidase, valine arylamidase, acid phosphatase, naphthol-AS-BI-phosphahydrolase, β-galactosidase (weak), α-glucosidase and β-glucosidase but not lipase C4, cysteine arylamidase, trypsin, α-chymotrypsin, α-galactosidase, β-glucuronidase, N-acetyl-β-glucosaminidase, α-mannosidase and α-fructosidase (API ZYM). Weak positive reaction for β-galactosidase, but negative reactions for nitrate reduction, indole production, glucose fermentation, arginine dihydrolase, urease, aseculin hydrolysis, and gelatin hydrolysis. Assimilates D-glucose, D-mannose, N-acetyl-glucosamine, and D-maltose, but not L-arabinose, D-mannitol, Potassium gluconate, capric acid, adipic acid, malic acid, trisoldium citrate or phenylacetic acid (API 20NE).

Fatty Acid Composition

After incubation for 24 hours at 28° C., a loopful of well-grown cells were harvested and fatty acid methyl esters were prepared, separated and identified using the Sherlock Microbial Identification System (MIDI) as described by Vandamme et al. (1992). The predominant fatty acids present in the *Flavobacterium* sp. H492 are shown in Table 1 below:

TABLE 1

Fatty Acid Composition of *Flavobacterium* sp. H492

| FAME | Percent | FAME2 | Percent |
|---|---|---|---|
| 13:0 iso | 0.27 | 15:0 anteiso | 1.49 |
| 13:1 at 12-13 | 0.16 | 15:1 w6c | 0.74 |
| 14:0 | 0.77 | 16:1 iso H | 0.29 |
| 15:1 iso G | 5.22 | Sum In Feature 2 | 0.45 |
| 15:0 iso | 34.96 | 16:0 iso | 0.64 |
| Sum In Feature 3 | 9.97 | 16:0 iso 3OH | 1.18 |

TABLE 1-continued

Fatty Acid Composition of *Flavobacterium* sp. H492

| FAME | Percent | FAME2 | Percent |
|---|---|---|---|
| 16:1 w5c | 0.41 | 16:0 3OH | 2.11 |
| 16:0 | 3.73 | 18:1 w9c | 0.65 |
| 15:0 iso 3OH | 9.77 | 17:0 iso 3OH | 15.24 |
| 15:0 2OH | 0.19 | 17:0 2OH | 0.34 |
| Sum In Feature 9 | 7.51 | 17:1 w8c | 0.28 |
| Sum In Feature 4 | 1.68 | 17:1 w6c | 0.69 |
| 17:0 iso | 1.28 | | |

A comparison of the fatty acid composition of *Flavobacterium* sp. H492 with those of known microbial strains in the MIDI database suggested that the fatty acids in the novel *Flavobacterium* sp. H492 strain were most similar with those of *Flavobacterium johnsoniae* (0.5 similarity index) and *Flavobacterium hydatis* (0.307 similarity index).

Resistance to Antibiotics

Antibiotic susceptibility of *Flavobacterium* sp. H492 was tested using antibiotic disks on Muller-Hinton medium as described in PML Microbiological's technical data sheet #535. Results obtained after 48-hour incubation at 25° C. are presented in Table 2.

TABLE 2

Susceptibility of *Flavobacterium* sp. H492 to various antibiotics

| | Concentration (ug) | Susceptible |
|---|---|---|
| Tetracycline | 30 | +++ |
| Kanamycin | 30 | − |
| Erythromycin | 15 | +++ |
| Streptomycin | 10 | ++ |
| Penicillin | 10 | +++ |
| Ampicillin | 10 | +++ |
| Oxytetracycline | 30 | +++ |
| Chloramphenicol | 30 | +++ |
| Ciprofloxacin | 5 | +++ |
| Gentamicin | 10 | ++ |
| Piperacillin | 100 | +++ |
| Cefuroxime | 30 | − |
| Imipenem | 10 | +++ |
| Sulphamethoxazole-Trimethoprim | 23.75/25 | ++ |

+++: very susceptible;
++: moderately susceptible;
+: susceptible;
−: not susceptible Production of *Flavobacterium* sp. H492 by Fermentation
DNA-DNA Hybridization

*Flavobacterium* sp. H492 consensus sequence was also identified using the EzTaxon-e server (http://eztaxon-e.e-zbiocloud.net/; Kim et al., 2012) on the basis of 16S rRNA sequence data. Top matches were all at th threshold for species differentiation. *Flavobacterium defluvii* and *Flavobacterium johnsoniae* were selected for DNA-DNA hybridization experiments.

Cells were disrupted by using a Constant Systems TS 0.75 KW (IUL Instruments, Germany) and the DNA in the crude lysate was purified by chromatography on hydroxyapatite as described by Cashion et al. (1977). DNA-DNA hybridization was carried out as described by De Ley et al. (1970) under consideration of the modifications described by Huss et al. (1983) using a model Cary 100 Bio UV/VIS-spectrophotometer equipped with a Peltier-thermostatted 6×6 multicell changer and a temperature controller with in-situ temperature probe (Varian). Results are shown in Table 3 below.

TABLE 3

DNA Sequence Comparison of *Flavobacterim* H492, *johnsoniae* and *defluvii*

| % DNA-DNA similarity (in 2 X SSC at 63° C.) | *Flavobacterium* sp strain H492 |
|---|---|
| *Flavobacterium johnsoniae* DSM 2064[T] | 30.7 (29.4) |
| *Flavobacterium defluvii* DSM 17963[T] | 8.3 (15.2) |

(Values in parentheses are results of measurements in duplicate)
*Flavobacterium* sp strain H492 does neither belong to the species *Flavobacterium johnsoniae* DSM 2064[T] (ID 12-1016) nor to the species *Flavobacterium defluvii* DSM 17963[T] when the recommendations of a threshold value of 70% DNA-DNA similarity for the definition of bacterial species by the ad hoc committee (Wayne et al., 1987) are considered.

Based on the biochemical, fatty acid, 16S rRNA and hybridization data collected, it appears that *Flavobacterium* sp. H492 is a new species within the genus *Flavobacterium*, and that it is unlike any other validly described *Flavobacterium* species described to date.

Production of *Flavobacterium* sp H492 by Fermentation

A supernatant with nematicidal activity was produced through the submerged fermentation of strain H492 under aerobic conditions and in liquid V8 medium.

A seed plate was started by streaking a fresh potato dextrose agar plate with a small amount of strain H492 using a sterile loop. The plate was incubated at 25° C. for 2-3 days or until enough biomass was evident on the surface of the plate.

A 50 mL V8 medium seed flask was inoculated with one loopful of material collected from the agar plate surface. The seed was incubated in a shaker at 200 rpm for 2 days.

A glass 2.8 L, non-baffled fernbach flask containing 500 mL of V8 medium was aseptically inoculated with 2% of seed. The fermentation was allowed to proceed at 25° C. for 5 days with constant agitation at 150-200 rpm.

The supernatant was obtained by separation of the cells from the spent fermentation broth by centrifugation, or other means of separation.

Activity of the supernatant was verified by means of the bioassay described below.

In Vitro Dose-Response Assay Against *Meloidogyne Incognita*

To evaluate the efficacy and stability of *Flavobacterium* sp. H492, whole cell broth (WCB) was tested at different dilution rates with water: 100%=100 µl of WCB; 70%=70 µl of H492: 30 µl of water; 50%=50 µl of H492: 50 µl of water; 20%=20 µl of H492: 80 µl of water. In this bioassay, the juveniles are exposed to the indicated treatments for 24 hours and then transferred to 6-well plates containing 1.2% water agar for an additional 24 hours to finally measure their movement. This experiment is designed to measure motility of the juveniles based on the number of treated juveniles that move out of an initial droplet that is placed on the 6-well plate where each treatment is tested in 6 replicates: An initial exposure of 100 µl of each microbial sample is dispensed into its corresponding well followed by 50 µl of nematode solution is added that contains approximately 300 nematodes. Twenty four hours after the initial treatment the juveniles are transferred onto 6-well plates that contain 1.2% water agar that incubate for another 24 hours at 25° C. Percent immotility is calculated based on the initial number of juveniles transferred. Percent immotility is calculated based on the initial number of juveniles transferred. The results are shown in FIG. 1 and indicate that H492 dilutions of 100%, 70%, 50%, and 20% show a dose response control for *M. incognita* juveniles as compared to the same dilutions of label rate avid.

Example 2: Nematicidal Activity of *Flavobacterium* sp. H492 Supernatant in the Presence of Host Plant Agar Seedling Assay: *Meloidogyne incognita* on Cucumber To assess the effect of the supernatant of H492 on J2s of *M. incognita*,] the following test was conducted on 60 mm-diameter petri dishes.

Seeds of cucumber (*Cucumis sativus*, cv. White Wonder) were germinated on wet tissue paper in petri dishes at room temperature. A week later, germinated seedlings were transferred to water agar in petri dishes at the rate of one seedling per dish. A 300 µl aliquot of *Flavobacterium* sp. H492 fermentation supernatant was added into each dish after which, 300 J2s of *M. incognita* were added in 150 µl of deionized water. Petri dishes were covered and incubated at 25° C. for 7 days. Water, media blank and avid (0.1%) were used as negative and positive controls, respectively. The effect of each substance on nematode pathogenicity was checked after 7 days by counting the number of galls in cucumber roots. The number of galls in each treatment was calculated as a % of the water control. Experiments were ran in duplicate.

*Flavobacterium* sp. H492 supernatant significantly reduced the number of galls in cucumber roots compared with the water control in both trials. More than 80% gall reduction was observed, which indicated that H492 is effective against *M. incognita* in cucumber.

Agar Seedling Assay: *Meloidogyne hapla* on Tomato

To assess the effect of H492 top supernatant on J2s of *M. hapla*, the following test was conducted on 90 mm-diameter petri dishes. Seeds of tomato (cv. UC 82) were germinated on wet paper tissue in petri dishes under room temperature. A week later, germinated seedlings were transferred to water agar in petri dishes at the rate of 4 seedlings per dish. A 300 µl aliquot of H492 supernatant was added into each dish after which, 700 J2s of *M. hapla* were dispensed in 150 µl of deionized water. Liquid solutions were distributed evenly around the four seedlings. Petri dishes were covered and incubated at 25° C. for 96 hours. Water and avid (0.5%) were used as negative and positive controls, respectively. Effect of each compound on nematode motility was checked after 96 hours by recording the number of motile nematodes in each treatment and relative mortality rate compared with the water control. Tomato roots were stained (Thies et al., 2002) and juvenile infection in the roots was observed under a compound microscope at 100× magnification.

Juveniles were only detected in the roots of water control. No nematode infection was observed in other treatments. H492 supernatant significantly reduced the number of motile nematodes compared with the water control (Table 4). H492 can immobilize juveniles of root-knot nematodes and protect plants from their infection.

TABLE 4

Effects of *Flavobacterium* sp. H492 supernatant on *Meloidogyne hapla* in tomato in a water-agar-assay.

| Treatment | No. Motile J2s/dish | Relative mortality rate (%)[z] |
|---|---|---|
| H492 | 140 ± 17 b | 44 ± 7 b |
| Avid (0.5%) | 105 ± 25 b | 60 ± 10 b |
| Water | 248 ± 35 a | 0 ± 10 a |

Means followed by the same letter in the same column are not different, according to Fisher's least significant difference at $P \leq 0.05$;
[z]nematode mortality rate relative to the water control.

Recovery of *Meloidogyne hapla* after Exposure to *Flavobacterium* sp. H492 Supernatant To assess the effect of H492 supernatant on the motility and subsequent recovery of J2s of *M. hapla*, the following test is conducted on 96-well plastic cell-culture plates.

A 50 μl aliquot of each test solution is added into appropriate wells after which, 50 nematodes dispensed in 30 μl of deionized water are added into each well. Plate is closed with a lid, and incubated at 25° C. for 72 hours. Water and Avid (1%) are used as negative and positive controls, respectively. Effect of each compound on nematode motility is checked after 24, 48, and 72 hours by adding a drop of 1N NaOH into each well, and the proportion of motile nematodes in each treatment is recorded using a scale of 0 to 100 percent. To assess the recovery of motility in each treatment, a volume of 70 μl is removed from each well, and the remaining solution in each well is diluted by adding 100 μl of deionized water. Plates are again incubated for 24 hours as described above, after which the second motility evaluation is performed. There are three replications for each treatment and the study is conducted twice.

Results are shown in Table 5 for all exposure times after washing. Percent of motile nematodes (also referred to as "mobile") exposed to H492 supernatant was decreased with the increased time of incubation, and the lowest rate of 17.5% was observed 72 hours after incubation. H492 supernatant reduce motility of J2s of root-knot nematodes and its effect can last at least for 72 hours.

TABLE 5

Percent recovery rate of *Meloidogyne hapla* after 24, 48, and 72 hours of incubation with *Flavobacterium* sp. H492 supernatant.

| | Candidate | | | |
|---|---|---|---|---|
| | 24 | 24-24 | 48-24 | 72-24 |
| Water | 95 ± 3.2 a | 97.5 ± 2.7 a | 95 ± 4.5 a | 90 ± 4.5 a |
| Avid (1%) | 10 ± 4.5 d | 13.3 ± 2.6 d | 11.7 ± 2.6 d | 10 ± 4.5 d |
| H492 (3303-52) | 45 ± 5.5 c | 45 ± 5.5 c | 22.5 ± 2.7 c | 17.5 ± 2.7 c |

Data are means for two studies. Means followed by the same letter in the same column are not significantly different, according to Fisher's least significant difference at P ≤ 0.05.
24: Observation made directly 24 h after incubation in H492 supernatant
24-24: Incubation for 24 h in the in the solution of each treatment and then 24 h in water
48-24: Incubation for 48 h in the solution of each treatment and then 24 h in water
72-24: Incubation for 72 h in the solution of each treatment and then 24 h in water Motility of *Meloidogyne hapla* after Exposure to *Flavobacterium* sp. H492 Supernatant at pH Levels To assess the effect of changing pH of H492 supernatant on the motility of J2s of *M. hapla*, the following test is conducted on 96-well plastic cell-culture plates.

A 50 μl aliquot of each test solution is added into appropriate wells after which, proper amount of 1N HCl or NaOH was added to adjust the pH of test solutions in the range of 3 to 12 as listed in Table 5. Fifty nematodes juveniles (J2) were dispensed in 30 μl of deionized water and added into each well, plate is closed with a lid, and incubated at 25° C. for 24 hours. Effect of each treatment on nematode motility is checked after 24 hours by adding a drop of 1N NaOH into each well, and the proportion of motile nematodes in each treatment is recorded using a scale of 0 to 100 percent. There are three replications for each treatment and this study was conducted twice.

Both increasing and decreasing the pH values of H492 supernatant reduced the percentage of motile nematodes (Table 6). However, increasing the pH level immobilized the nematodes more than decreasing, with the lowest motility at pH=12. Lower motility was observed at pH=10 than at pH=5. In conclusion, alkaline conditions had stronger effect than acid in suppressing or immobilizing nematodes.

TABLE 6

Effects of pH changes on *Flavobacterium* sp. H492 supernatant on the motility of *Meloidogyne hapla*

| Candidate | pH | | | | |
|---|---|---|---|---|---|
| | 3 | 5 | 8.4 | 10 | 12 |
| H492 (3303-52) | 46.7 ± 6.1 a | 39.2 ± 5.8 b | 50.8 ± 7.4 a | 9.2 ± 3.8 c | 6.7 ± 2.6 c |
| | 3 | 5 | 6.8 | 10 | 12 |
| Media | 95 ± 3.2 a | 85 ± 7.7 b | 85 ± 4.5 b | 75 ± 8.9 c | 18 ± 2.2 d |

Data are means for two studies. Means followed by the same letter in the same column are not different, according to Fisher's least significant difference at P ≤ 0.05.

Greenhouse Pot Assay: Cucumber with *Meloidogyne incognita*

To demonstrate the nematicidal activity of H492 supernatant, a greenhouse study on cucumber (cv. White Wonder) was performed using a supernatant as the test product to control *M. incognita*. One cucumber plant per pot was planted in autoclaved sand and grown in a greenhouse under natural daylight. Each pot with a two-week-old plant was treated with a 20 μL aliquot of the test product, after which 2000 fresh hatched *M. incognita* J2s were inoculated into each pot. A week later, a second 20 ml treatment of the test product was applied. Water, and avid (0.1%) were used as negative and positive controls, respectively. There were five replicates and the experiment was arranged in a randomized complete block design. Plants were allowed to grow in a greenhouse for four more weeks, after which each plant was harvested and evaluated for fresh shoot and root weights. Number of nematodes in each pot and root galls in each plant were recorded. Statistical analysis (ANOVA) was performed, and the statistical differences among treatment means were calculated at P≤0.05.

Data presented in Table 7 below show that although cucumber shoot and root fresh weights were not statistically different from the untreated water control, the pots treated with H492 supernatant contained significantly less nematodes than the untreated water control pots. Root gall number in H492 supernatant treatment was significantly lower than that of water or media blank control. It was indicated that H492 supernatant was effective in restraining gall formation by *M. incognita* in cucumber.

TABLE 7

Effects of *Flavobacterium* sp. H492 supernatant on *Meloidogyne incognita* in cucumber in a greenhouse pot assay.

| Treatment | Shoot Weight (g) | Root Weight (g) | Gall Number | Nematode Number |
|---|---|---|---|---|
| Avid | 15.2 ± 4.4 | 5.2 ± 2.1 | 0 ± 0 d | 316 ± 193 b |
| Water | 21.1 ± 2.6 | 6.3 ± 1.2 | 29.0 ± 8.2 a | 510 ± 256 a |
| H492 (7501-50) | 16.9 ± 6.2 | 4.9 ± 1.0 | 7.8 ± 2.9 c | 276 ± 195 b |

Means followed by the same letter in the same column are not different, according to Fisher's least significant difference at $P < 0.05$.

Greenhouse Pot Assay: Cucumber and Tomato with *Meloidogyne hapla*

Greenhouse studies on cucumber (cv. White Wonder) and tomato (*Solanum lycopersicum*, cv. Roma) are performed to demonstrate the nematicidal activity of *Flavobacterium* sp. H492 supernatant for control of *M. hapla*. One cucumber or tomato seed per pot is planted in autoclaved sand and grown in a greenhouse under natural day light. Each pot with a two-week-old cucumber or three-week-old tomato seedling is treated with an 40-µL aliquot of the test product, after which 2000 J2s of *M. hapla* are inoculated into each pot. A week later a second treatment of the test product is applied to the pots at the same rate as the first time. Water, media, and Avid (0.1%) are used as negative and positive controls, respectively. There are five replicates and the experiment is arranged in a randomized complete block design. Plants are grown in a greenhouse for four or six more weeks, respectively for cucumber and tomato, after which each plant was harvested and evaluated for shoot height, fresh shoot and root weights. Plant vigor and root galling index were rated on a scale of 0 to 10, respectively as 0=dead, 10=the best healthy; and 0=no gall, 10=100% root galled. Number of nematodes in each pot was recorded. Statistical analysis (ANOVA) is performed, and the statistical differences among treatment means were calculated at $P \le 0.05$.

Results on cucumber and tomato in trial one are presented in Tables 8 and 9, respectively. *Flavobacterium* sp. H492 supernatant significantly reduces the root gall index in cucumber and the number of nematodes in tomato compared with the water control. In trial two, root gall index caused by *M. hapla* is reduced in cucumber but not in tomato (Tables 10 and 11). Both trials suggested that *Flavobacterium* sp. H492 supernatant can reduce number of galls in plants from *M. hapla*.

TABLE 8

Effects of *Flavobacterium* sp. H492 supernatant on *Meloidogyne hapla* in cucumber in a greenhouse pot assay

| Treatment | Plant Vigor[y] | Root Gall Index[z] | Number of J2s |
|---|---|---|---|
| H492 | 4 ± 1 a | 6 ± 3 b | 5033 ± 1662 a |
| Avid (1%) | 0 ± 0 b | 0 ± 0 c | 0 ± 0 b |
| Water | 1 ± 1 ab | 8 ± 1 a | 5467 ± 611 a |

Means followed by the same letter in the same column are not different, according to Fisher's least significant difference at $P \le 0.05$.

[y]Plant vigor in a 0-10 scale: 0: dead, 10: the best healthy.

[z]Root gall index in a 0-10 scale: 0: no gall, 10: 100% root galled.

TABLE 9

Effects of *Flavobacterium* sp. H492 supernatant on *Meloidogyne hapla* in tomato in a greenhouse pot assay

| Treatment | Shoot Height (cm) | Shoot Weight (g) | Root Weight (g) | Root Gall Index | Nematode Number |
|---|---|---|---|---|---|
| H492 (3303-52) | 20 ± 6 b[z] | 10 ± 1 b | 2.5 ± 1 | 2 ± 1 | 175 b |
| Avid (1%) | 8 ± 8 c | 1 ± 1 c | 0.4 ± 1 | 0 ± 0 | 0 c |
| Water | 28 ± 6 ab | 14 ± 4 b | 4.2 ± 1 | 2 ± 1 | 325 a |

Means followed by the same letter in the same column are not different, according to Fisher's least significant difference at $P \le 0.05$.

TABLE 10

Effects of *Flavobacterium* sp. H492 supernatant on *Meloidogyne hapla* in cucumber in a greenhouse pot assay (Trial I)

| Treatment | Top Weight | Root Weight | Root Gall Index | Nematode Number |
|---|---|---|---|---|
| Avid (1%) | 16.1 ± 4.5 a | 4.9 ± 2.5 a | 0.2 ± 0.4 d | 1180 ± 920 c |
| Water | 5.9 ± 1.2 b | 0.5 ± 0.3 b | 7.2 ± 1.3 a | 2580 ± 934 ab |
| H492 (3303-52) | 9.0 ± 2.5 b | 2.0 ± 0.9 b | 3.2 ± 0.8 c | 1840 ± 856 bc |

Means followed by the same letter in the same column are not different, according to Fisher's least significant difference at $P \le 0.05$.

TABLE 11

Effects of *Flavobacterium* sp. H492 supernatant on *Meloidogyne hapla* in tomato in a greenhouse pot assay (Trial II)

| Treatment | Top Weight | Root Weight | Root Gall Index | Nematode Number |
|---|---|---|---|---|
| Avid (1%) | 16.9 ± 4.8 ab | 6.2 ± 2.1 ab | 0 ± 0 b | 332 ± 385 |
| Water | 14.1 ± 1.1 b | 5.7 ± 1.7 b | 4.1 ± 3.2 a | 334 ± 241 |
| H492 (3303-52) | 16.4 ± 1.9 ab | 7.3 ± 1.4 ab | 4.6 ± 1.5 a | 594 ± 374 |

Means followed by the same letter in the same column are not different, according to Fisher's least significant difference at $P \le 0.05$.

Figure 2:
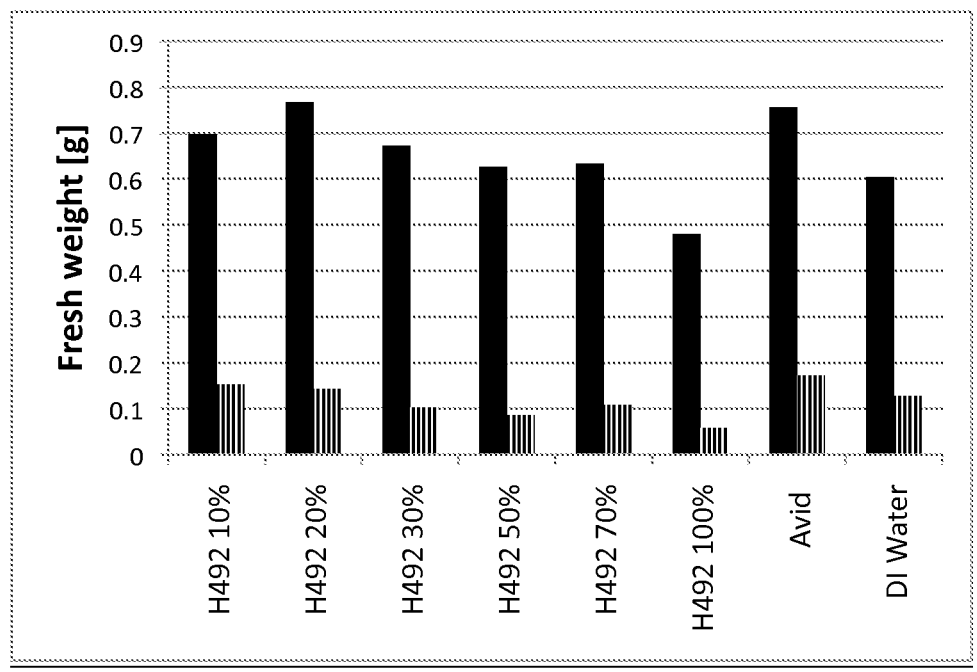
FIG. 2 shows the fresh shoot weight (black bars) and fresh root weight (bars with vertical lines) of cucumber plants used in the 50 mL tube assay and treated with different concentrations of H492 whole cell broth.
Figure 3:
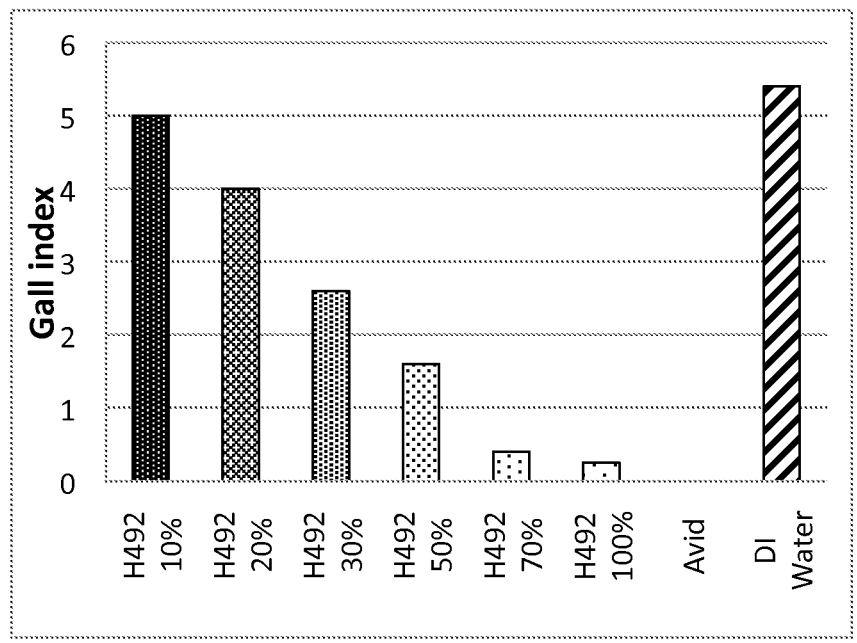
FIG. 3 shows the gall index of cucumber roots treated with different doses of whole cell broth of H492 two weeks after inoculation with *Meloidogyne. incognita.*
Figure 4:
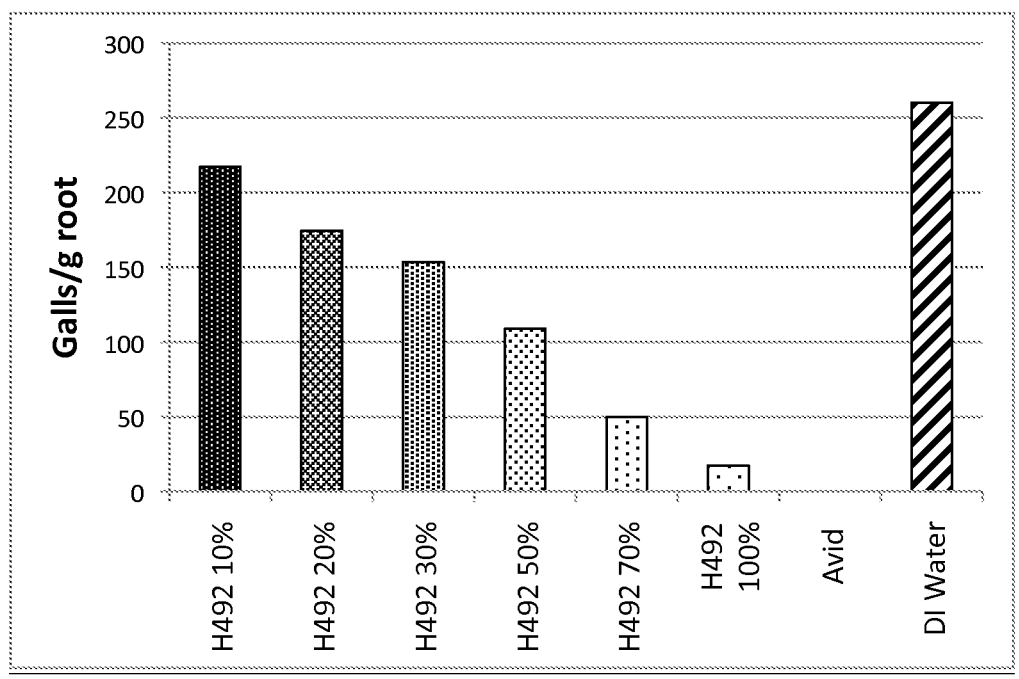
FIG. 4 shows the galls/gram of root of cucumber roots treated with different doses of whole cell broth of H492 two weeks after inoculation with *M. incognita.*

In Planta Dose-Response of *Flavobacterium* sp. H492 on *M. incognita* Using Cucumber as Plant Host Modified 50 mL falcon tubes with holes in the bottom to allow drenching were filled with mixture of sand and soil (1:2) and drenched with 2 mL of dilutions of H492 whole cell broth (10, 20, 30, 50, 70 and 100%), avid (70% of label rate) as positive control and water as negative control, respectively. After drenching, cucumber seeds (cv. SMR58) were planted in the tubes and tubes were inoculated with 800 eggs of *M. incognita*. Tubes were covered with parafilm and placed in a box with wet paper towels to high humidity. After 4 days, most of seed germinated and parafilm cover was removed. After one week, the second dose (1 mL of the sample) was applied into tubes. The test was terminated after two weeks and following parameters were scored: fresh shoot weight (FSW), fresh root weight (FRW), gall index (scale 1-10) and gall number per g of the root. In general FSW and FRW did not differ significantly between treatments. However, reduction of both FSW and FRW was noticeable in case of *Flavobacterium* sp. H492 whole cell broth applied at 100%. Gall index was reduced in case of all tested concentrations of *Flavobacterium* sp. H492 whole cell broth, except of the lowest dilution at 10%, when compared with water control treatment. All tested concentrations of *Flavobacterium* sp. H492 whole cell broth reduced the number of galls per gram of the root when compared with water control. The nematicidal activity of whole cell broth was dose dependent and was increasing with increasing concentrations of material (see FIG. 2-4)

Immobilization of Sting and Lance Nematodes in Infested Soil

These trials are conducted with field soils with predominately sting and lance nematodes. Each trial had 4 treatments: *Flavobacterium* sp. H492, growth media blank, positive control (i.e. avid 0.1%) and negative control (i.e. water). The trials are in randomized complete block design with 8 replications. Twelve liters of soil containing the desired nematode are collected, cleaned from turf/roots, and homogenized. After mixing the soil, five (100 cm$^3$) soil samples are extracted using centrifugation-sugar floatation method and counted to ensure the major nematodes of interest for these trials were evenly distributed throughout the soil. Next 200 cm$^3$ aliquots of soil were measured out and placed into a 2×2×2-inch plastic pot. The treatments are applied as a drench treatment (40 ml/pot). The pots are then placed on a lab bench and left for 72 hours so that the nematodes are exposed to the treatments. Next the soil from each pot is washed onto a modified Baermann apparatus for nematode extraction. This allows live nematodes to move out of the soil, through a filter, into water so that they can be counted. Dead or immobile nematodes stay in the soil. After incubating the Baermanns for 96 hours, the live nematodes were collected and counted. Nematode counts from each treatment were compared with SAS 9.2 using Fisher's LSD mean separation at P≤0.05 for all nematodes observed.

Four plant-parasitic nematode genera are observed in the field soil used to conduct the trial; *Belonolaimus* sp. (sting nematode), *Hopolaimus* sp. (lance nematode), *Peltamigratus* sp. and *Scutellonema* sp (spiral nematodes). Sting nematode counts are increased by 5% in the growth media treatment compared to the negative control (water), and decreased by 10% and 14% for H492 and Avid, respectively when compared to the negative control water. *Peltamigratus* sp. counts were decreased by 32%, 26% and 88% for media, H492 and avid, respectively when compared to the negative control (water). *Scutellonema* sp. counts are unchanged in the growth media treatment compared to the negative control (water), and decreased by 18% and 75% for H492 and avid, respectively. Treatment differences are observed for lance nematodes during the trial. Lance nematode counts are decreased by 35%, 28% and 69% for media, H492 and avid, respectively when compared to the water control.

Example 3: Nematode Spectrum Tests-Effect of *Flavobacterium* Sp. H492 WCB Whole Cell Broth Against Root-Knot Nematodes (RKN, *Meloidogyne incognita*), Reniform Nematodes (*Rotylenchulus reniformis*), Root Lesion Nematodes (*Pratylenchus* Spp.) and Soybean Cyst Nematodes (SCN, *Heterodera glycines*) and on Plant Growth and Vigor by Soil Drench The following three soil drench treatments are included in the efficacy test against each nematode tested with 7 replicates: (1) Treatment 1: negative control (100 ml of water); (2) Treatment 2: positive control (Vapam label rate in 100 ml of final volume) and (3) Treatment 3: *Flavobacterium* sp. H492 whole cell broth (WCB, 100 ml per application with 2 applications of one week apart).

1000 grams of field soil infested with *Meloidogyne incognita* (RKN), *Rotylenchulus reniformis, Pratylenchus* spp., and 1000 grams of sterile soil but inoculated with 1100-1200 eggs of *Heterodera glycines* in 1 ml of water are each put into PVC cylindrical pots. The soil is drenched with all three treatments by pouring the material slowly and evenly over the soil surface in the pot. The soil is lightly pressed to make a smooth level surface prior to application. After drenching, pots are covered with 2 mil, bags that are 0.002 inches thick, after treatment and sealed with a rubber band. The soil is drenched again with *Flavobacterium* sp. H492 WCB one week after the first drench. All of the pots with the application remain in the greenhouse bench until one week after the final application. Before planting, 100 ml of soil sample is removed to extract the nematodes, including plant parasitic, omnivorous (i.e. *Dorylaimus* spp.) and other nematodes that are non-parasitic to plants, using the Baermann funnel method.

Each pot is planted with the corresponding test crop. For RKN and reniform nematodes, cucumber seeds are planted; for root lesion nematodes, corn; for SCN, soybean. Five seeds of each crop are planted into each pot. The pots are replaced in the greenhouse in a randomized complete block design with seven replicates to grow the crop and until final take-down and sampling. Plant numbers are counted 10 days after planting. The whole experiment is incubated in the greenhouse for 5 weeks (for RKN, reniform and root lesion nematodes) and 7 weeks (for SCN).

During the incubation period, plant growth and vigor is also monitored to see if there is any indication that *Flavobacterium* H492 improves plant health compared to the negative and positive controls. The following parameters are thus measured: (a) plant counts per pot; (b) nematode counts in 100 ml of soil at final sampling, including plant parasitic, *Dorylaimus* spp. and non-parasitic nematodes, with Baermann funnel method (Dinaburg, 1942); (c) nematode counts from total roots at final sampling; (d) height of shoots (cm); (e) weight of fresh shoots (g); weight of fresh root (g); (h) plant vigor rating using a subjective scale of 1 to 5, with 1 as poor plant vigor, characterized by poor plant growth and thin light green leaves and 5 as best plant vigor, characterized by healthy growth and dark green leaves; (i) root rating using a subjective scale of 1 to 5 to evaluate the root health with 1 as worst root health with small, dark and unhealthy-looking root system and poor branching while 5 as a nice white and healthy fibrous root system without dark or browning necrosis; (j) gall index (Bridge and Page, 1980; 0 to 10 scale) and total gall numbers for RKN and (k) Cyst counts for SCN.

Data is analyzed with the Agricultural Research Management (ARM) program to evaluate the results with a separation at P=0.05 level when there is activity present. Overall, *Flavobacterium* H492 reduces the damage of reniform nematode and root-knot nematodes on cucumber and root lesion nematode on corn in nematode infested field soil in the test compared to water control and increases plant biomass and plant vigor, including plant heights, top weight, root weight, root health and plant vigor compared to water control. The plant enhancement effects of *Flavobacterium* sp. H492 on plant parts above the ground are superior to soil-fumigant Vapam, while the effects on root health are the same as Vapam. *Flavobacterium* sp. H492 significantly reduces the SCN nematodes in total roots compared to water control. Results with specific nematodes are discussed below.

Figure 5:
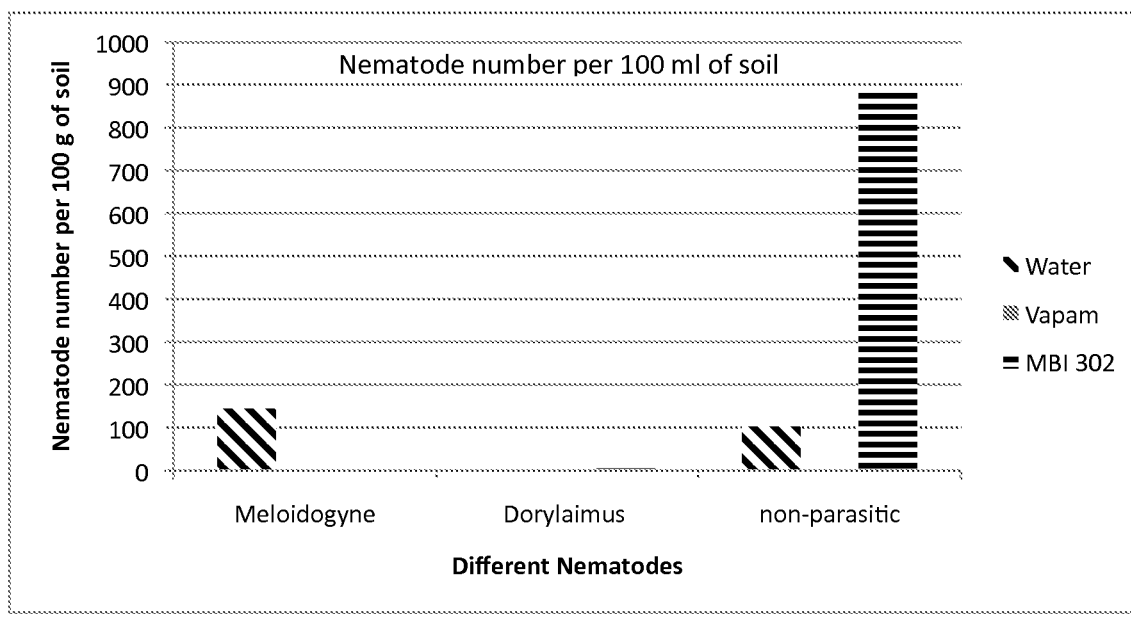
FIG. 5 shows the effect of *Flavobacterium* sp. H492 (MBI-302) whole cell broth on root-knot nematodes (*Meloidogyne incognita*), *Dorylaimus* spp. and other non-parasitic nematodes in 100 ml of soil at harvest in the cucumber test.
Figure 6:
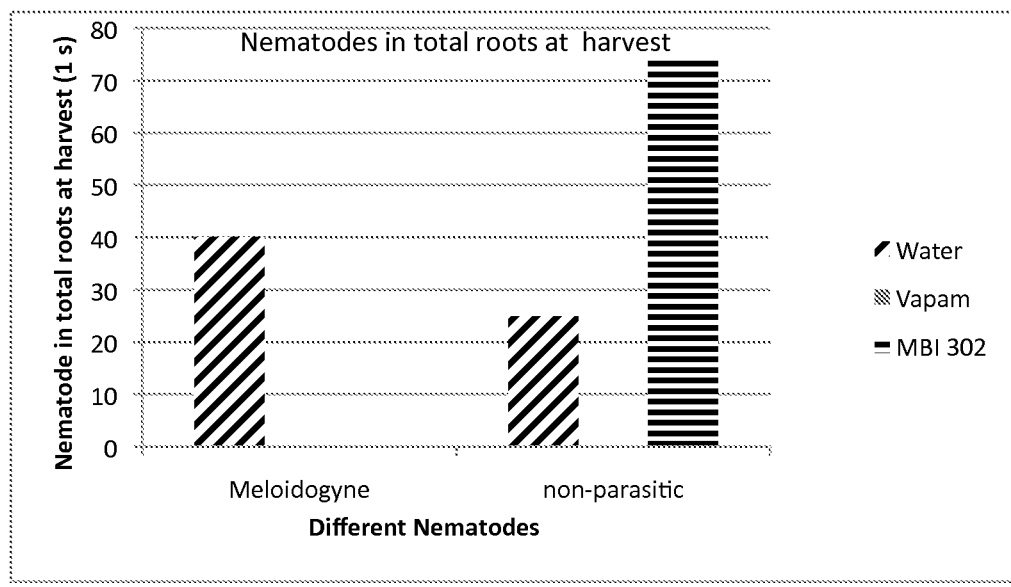
FIG. 6 shows the effect of *Flavobacterium* sp. H492 (MBI-302) whole cell broth on root-knot nematodes (*Meloidogyne incognita*) and non-parasitic nematodes in cucumber roots (total roots) at harvest.
Figure 7:
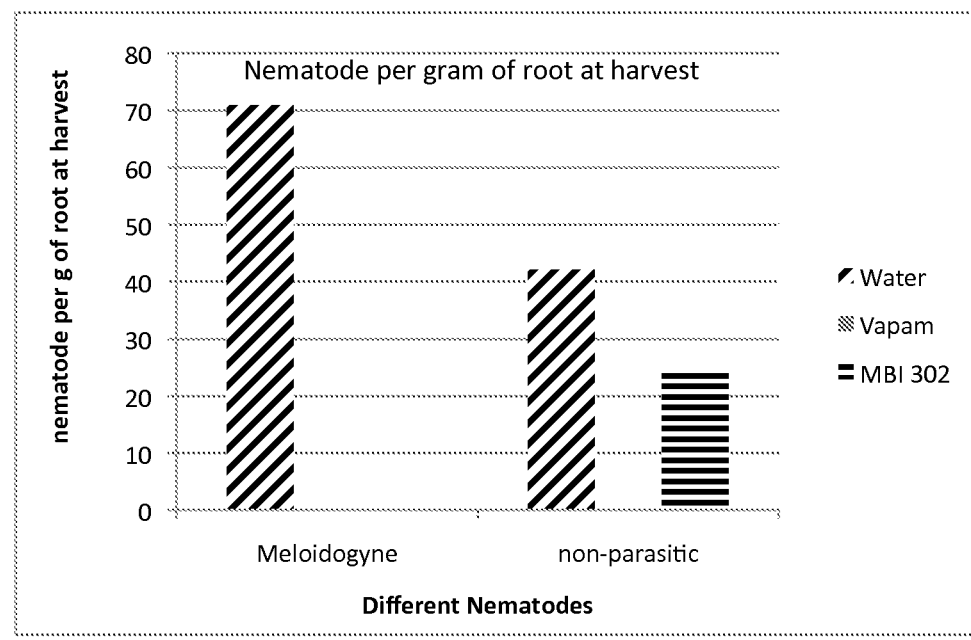
FIG. 7 shows the effect of *Flavobacterium* sp. H492 (MBI-302) whole cell broth on root-knot nematodes (*Meloidogyne incognita*) and non-parasitic nematodes in cucumber roots (per g) at harvest.
Figure 8:
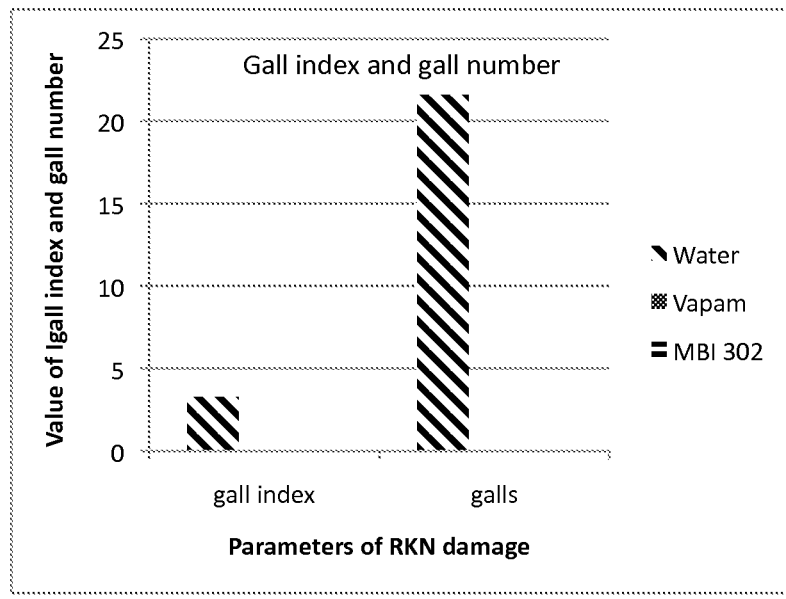
FIG. 8 shows the effect of *Flavobacterium* sp. H492 (MBI-302) whole cell broth on root-knot nematodes (*Meloidogyne incognita*) gall index and gall number on cucumber roots at harvest.
Figure 9:
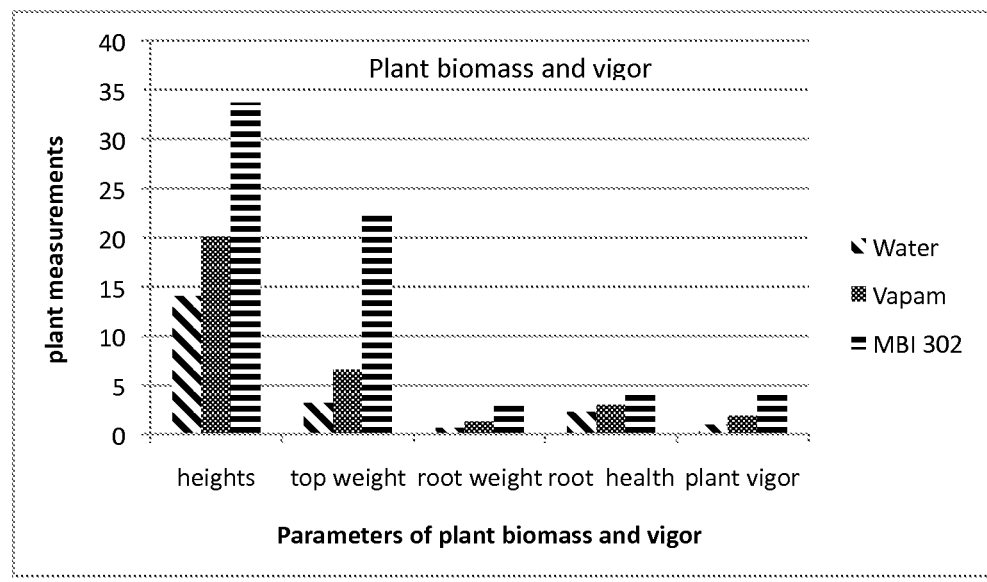
FIG. 9 shows the effect of *Flavobacterium* sp. H492 (MBI-302) whole cell broth on cucumber plant biomass and vigor at harvest in the root-knot nematodes (*Meloidogyne incognita*) test with cucumber.

In the RKN test (see FIGS. 5-9), *Flavobacterium* sp. H492 significantly reduces numbers of root-knot nematodes in 100 ml of soil, total roots, one gram of roots, gall index and total gall numbers compared to water control, and had the same effects on reduction as Vapam (see FIG. 8). Numbers of *Dorylaimus* spp. in 100 ml of soil, and non-parasitic nematodes in 100 ml of soil and total roots, are significantly increased by MBI-302 (*Flavobacterium* sp. H492) compared to water control and Vapam (see FIGS. 5 and 6). Plant height, top weight, root weights, root health are significantly increased by MBI-302 (*Flavobacterium* sp. H49)2 compared to water and Vapam (see FIG. 9).

Figure 10:
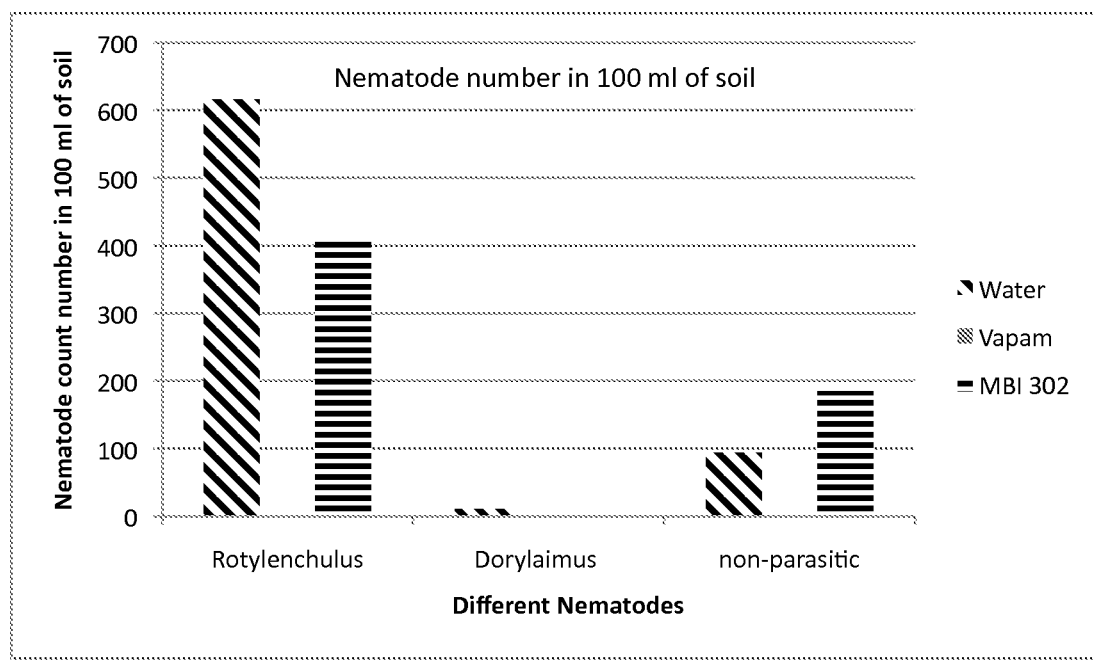
FIG. 10 shows the effect of *Flavobacterium* sp. H492 (MBI-302) whole cell broth on reniform nematodes (*Rotylenchulus reniformis*), *Dorylaimus* spp. and other non-parasitic nematodes in soil in the cucumber test.
Figure 11:
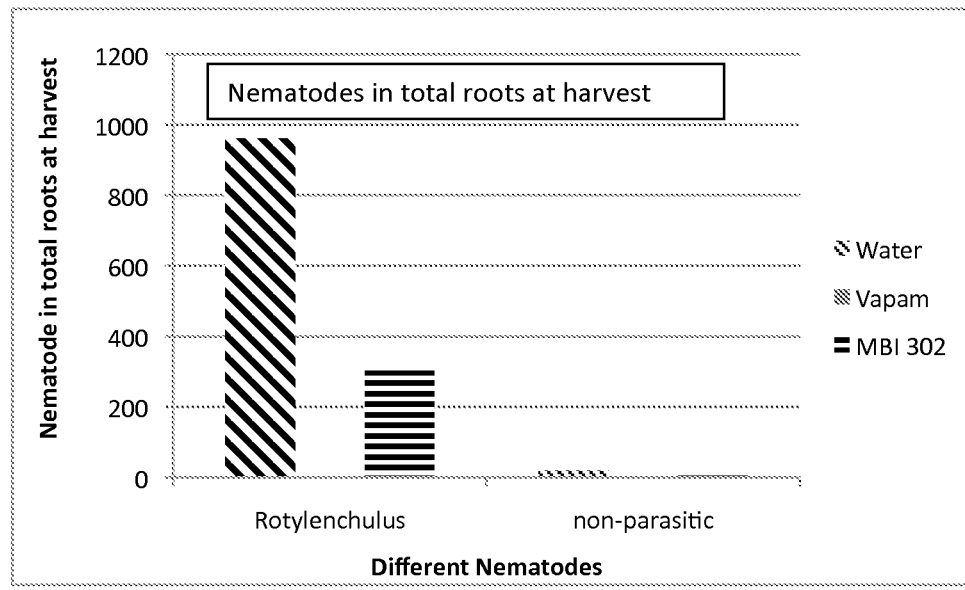
FIG. 11 shows the effect of *Flavobacterium* sp. H492 (MBI-302) whole cell broth on reniform nematodes (*Rotylenchulus reniformis*) and non-parasitic nematodes in cucumber roots (total roots) at harvest.
Figure 12:
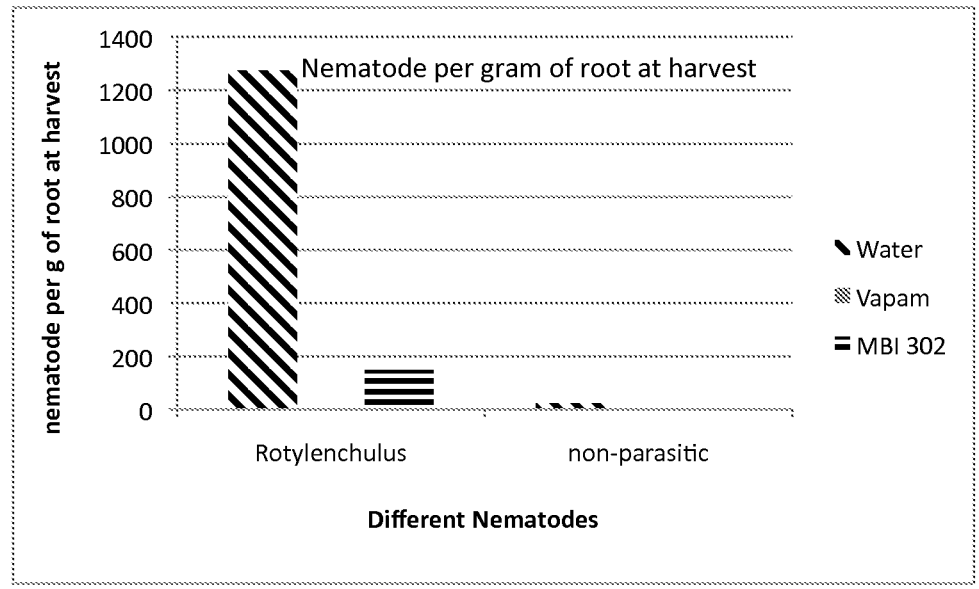
FIG. 12 shows the effect of *Flavobacterium* sp. H492 (MBI-302) whole cell broth on reniform nematodes (*Rotylenchulus reniformis*) and non-parasitic nematodes in cucumber roots (per g of root) at harvest.
Figure 13:
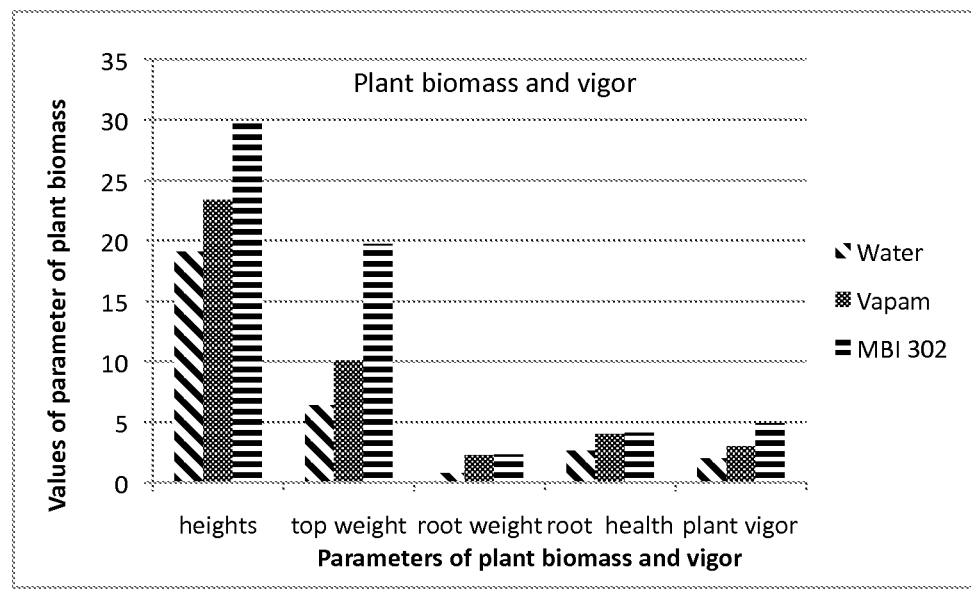
FIG. 13 shows the effect of *Flavobacterium* sp. H492 (MBI-302) whole cell broth on cucumber plant biomass and vigor at harvest in the reniform nematodes (*Rotylenchulus reniformis*) test with cucumber.

In the reniform nematode test, MBI-302 (*Flavobacterium* H492) significantly reduces numbers of reniform nematodes in 100 ml of soil, total roots and one gram of roots compared to water control (see FIG. 10). Numbers of *Dorylaimus* spp. in 100 ml of soil are not affected by *Flavobacterium* sp. H492 (see FIG. 10) compared to water control. Numbers of non-parasitic nematodes in 100 ml of soil and total roots are significantly increased by *Flavobacterium* sp. H492 (see FIG. 10), but are significantly reduced in one gram of roots compared to water control (see FIGS. 11 and 12). Plant height, top weight and plant vigor are significantly increased by *Flavobacterium* sp. H492 compared to water and Vapam (FIG. 13). Plant root weight and root health were significantly increased compared to water control, and the same as Vapam (FIG. 13).

Figure 14:
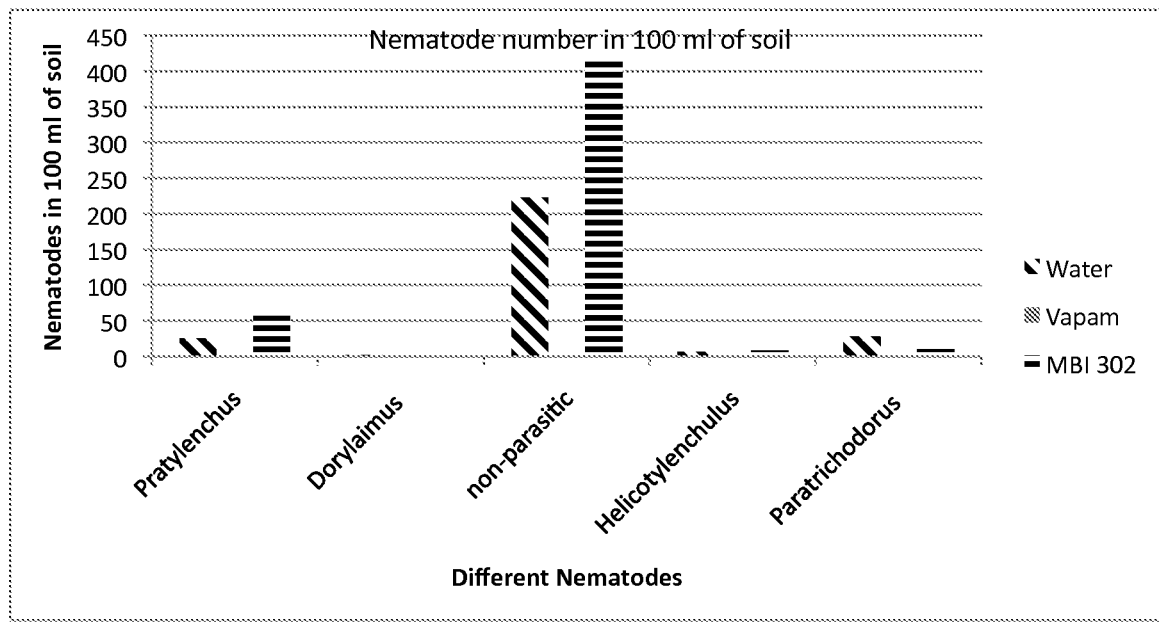
FIG. 14 shows the effect of *Flavobacterium* sp. H492 (MBI-302) whole cell broth on root lesion nematodes (*Pratylenchus* spp.), spiral nematodes (*Helicotylenchulus* spp), stubby root nematodes (*Paratrichodorus* spp.), *Dorylaimus* spp. and other non-parasitic nematodes in the corn test.
Figure 15:
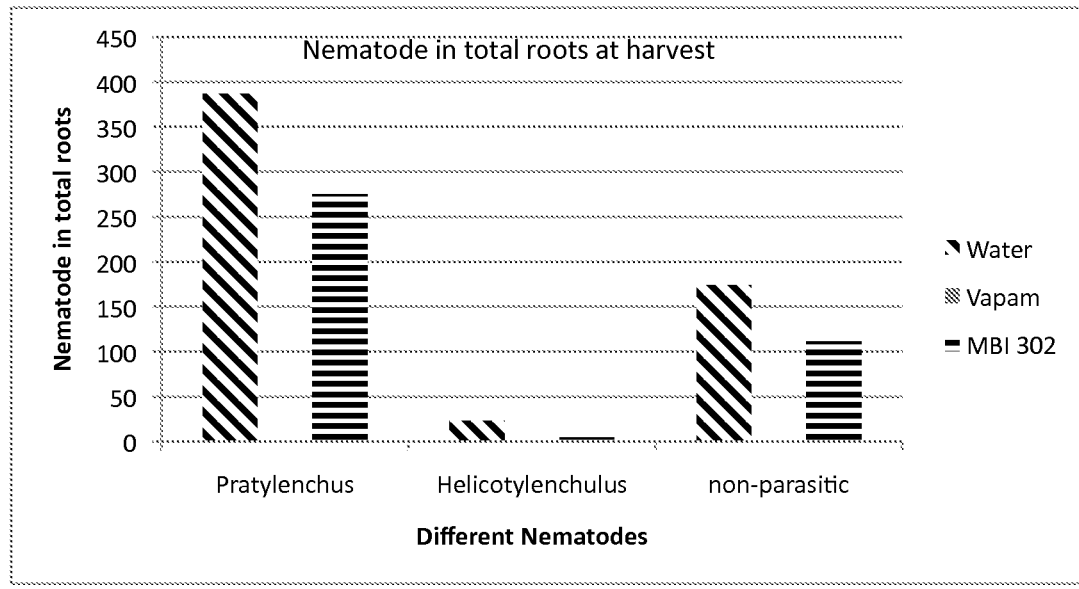
FIG. 15 shows the effect of *Flavobacterium* sp. H492 (MBI-302) whole cell broth on root lesion nematodes (*Pratylenchus* spp.), spiral nematodes (*Helicotylenchulus* spp.) and non-parasitic nematodes in corn roots (total roots) at harvest with corn.
Figure 16:
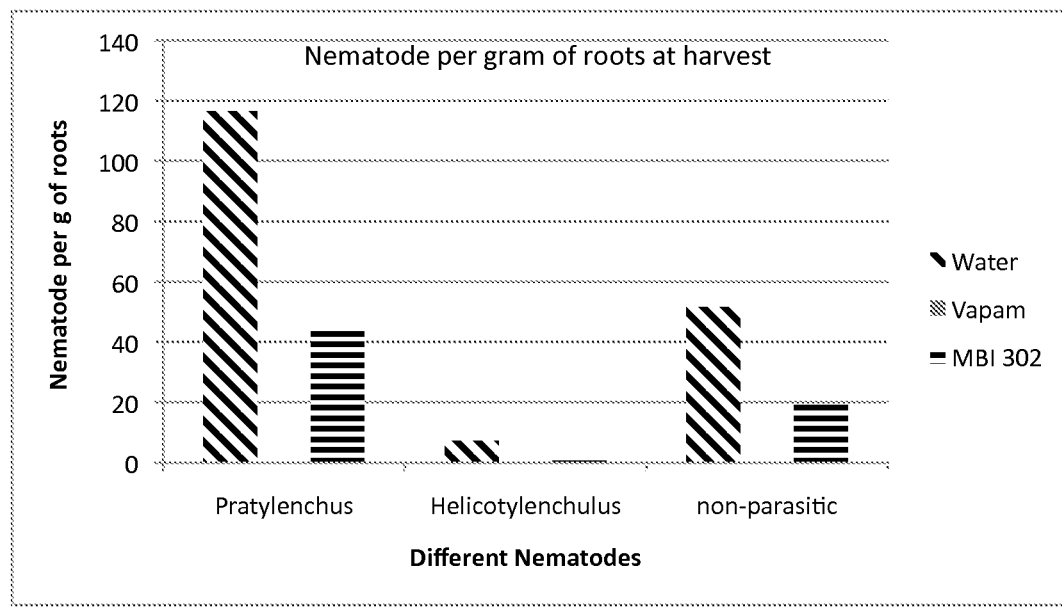
FIG. 16 shows the effect of *Flavobacterium* sp. H492 (MBI-302) whole cell broth on root lesion nematodes (*Pratylenchus* spp.), spiral nematodes (*Helicotylenchulus* spp.) and non-parasitic nematodes in corn roots (per g of root) at harvest in the corn test.
Figure 17:
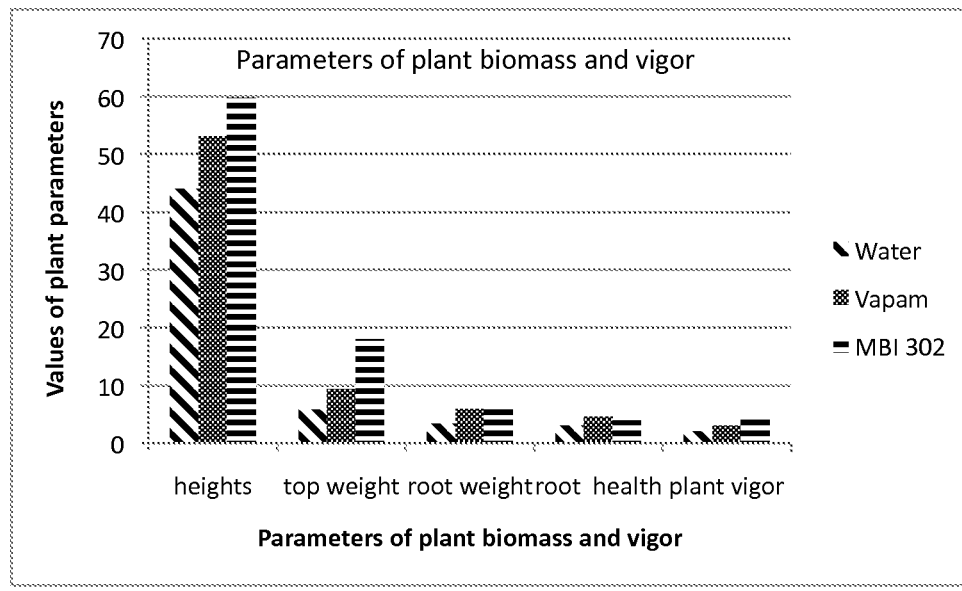
FIG. 17 shows the effect of *Flavobacterium* sp. H492 (MBI-302) whole cell broth on corn plant biomass and vigor at harvest in the root lesion nematode (*Pratylenchus* spp.) test with corn.

In the test with lesion nematodes, *Flavobacterium* sp. H492 significantly increases the numbers of one of the plant parasitic nematodes, *Pratylenchus* spp (lesion nematodes) but does not reduce the numbers of the other two parasitic nematodes *Helicotylenchulus* spp. (spiral nematodes) and *Paratrichodorus* spp. (stubby root nematodes) in 100 ml of soil compared to water control (see FIG. 14). Numbers of lesion, spiral and stubby root nematodes in total corn roots and one gram of corn roots, are significantly reduced compared to water control (see FIGS. 15 and 16). Numbers of non-parasitic nematodes in 100 ml of soil were significantly increased by *Flavobacterium* sp. H492 compared to water control. Plant height, top weight, and plant vigor are significantly increased by *Flavobacterium* sp. H492 compared to water and Vapam (see FIG. 17). Plant root weights and root health are significantly increased by *Flavobacterium* sp. H492 compared to water control (see FIG. 17).

Figure 18:
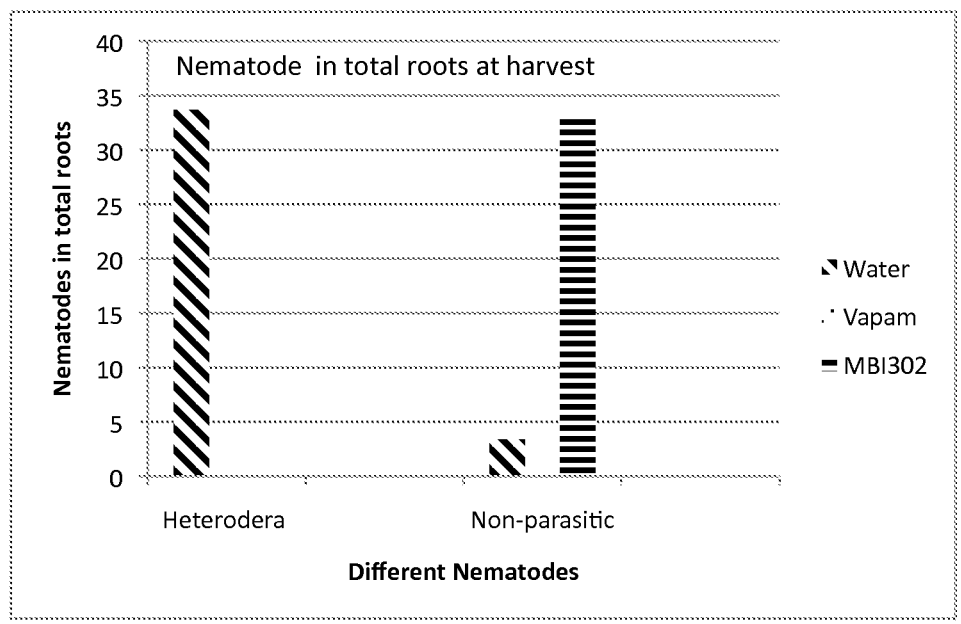
FIG. 18 shows the effect of *Flavobacterium* sp. H492 (MBI-302) whole cell broth on soybean cyst nematodes (*Heterodera glycines*) in the soybean test.
Figure 19:
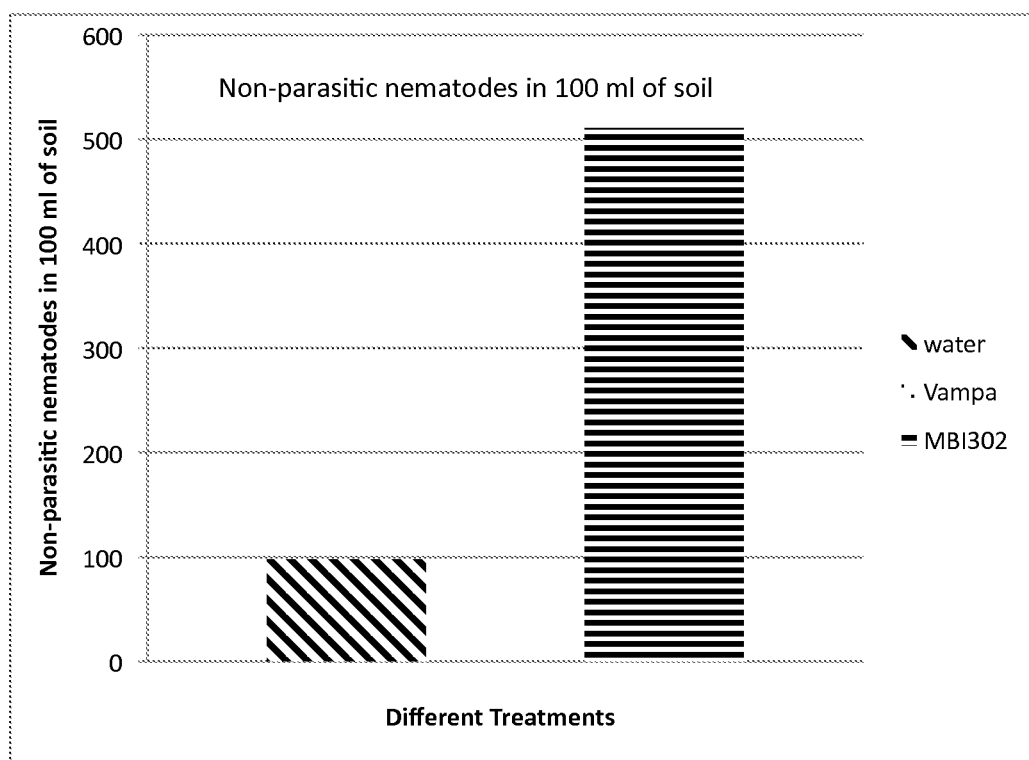
FIG. 19 shows the effect of *Flavobacterium* sp. H492 (MBI-302) whole cell broth and water on non-parasitic nematodes in the soybean test.

*Flavobacterium* sp. H492 significantly reduces the SCN numbers in total roots compared to water control but with the same effect as Vapam (see FIG. 18). The bacteria significantly increased numbers of non-parasitic nematodes in 100 ml of soil and in total roots compared to water and Vapam (see FIG. 19).

Example 5: Extraction of Compounds from *Flavobacterium* sp. H492

Figure 20:
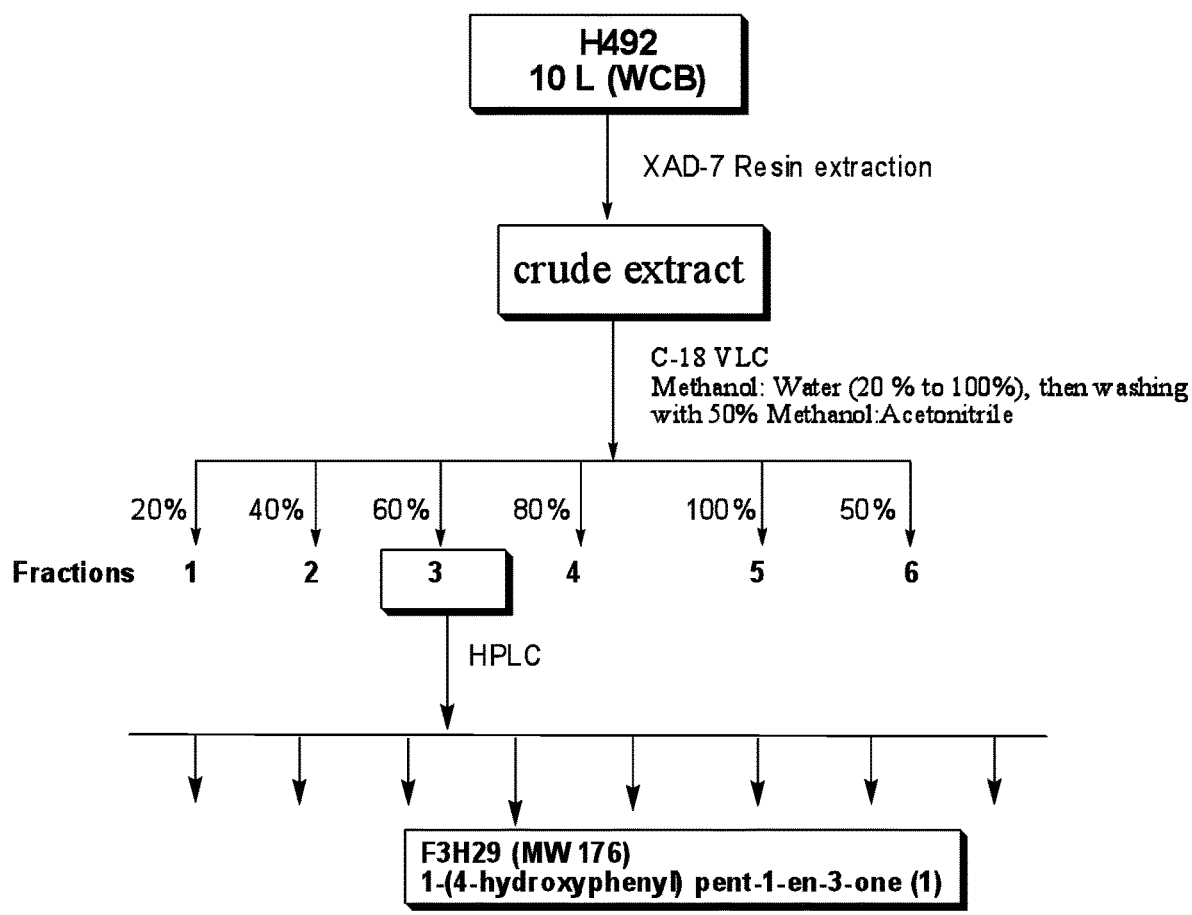
FIG. 20 is a schematic representation of purification scheme for obtaining the compounds of the invention from culture broth.

The following procedure is used for the purification of compounds extracted from the culture of *Flavobacterium* sp. H492 (see FIG. 20):

The culture broth derived from the 10-L fermentation of *Flavobacterium* sp. in V-8-broth is extracted with Amberlite XAD-7 resin (Asolkar et al., 2006) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone/methanol (50/50) after which the acetone/methanol is filtered and dried under vacuum using rotary evaporator to give the crude extract. The crude extract is then fractionated by using reversed-phase C18 vacuum liquid chromatography ($H_2O/CH_3OH$; gradient 90:20 to 0:100%) to give 6 fractions (FIG. 20). These fractions are then concentrated to dryness using rotary evaporator and the resulting dry residues are screened for biological activity using *Meloidogyne incognita* and *M. hapla*. The active fractions are then subjected to reversed phase HPLC (Spectra System P4000 (Thermo Scientific) to give pure compounds, which are then screened in above mentioned bioassays to locate/identify the active compounds. To confirm the identity of the compound, additional spectroscopic data such as LC/MS and NMR is recorded.

Figure 22:
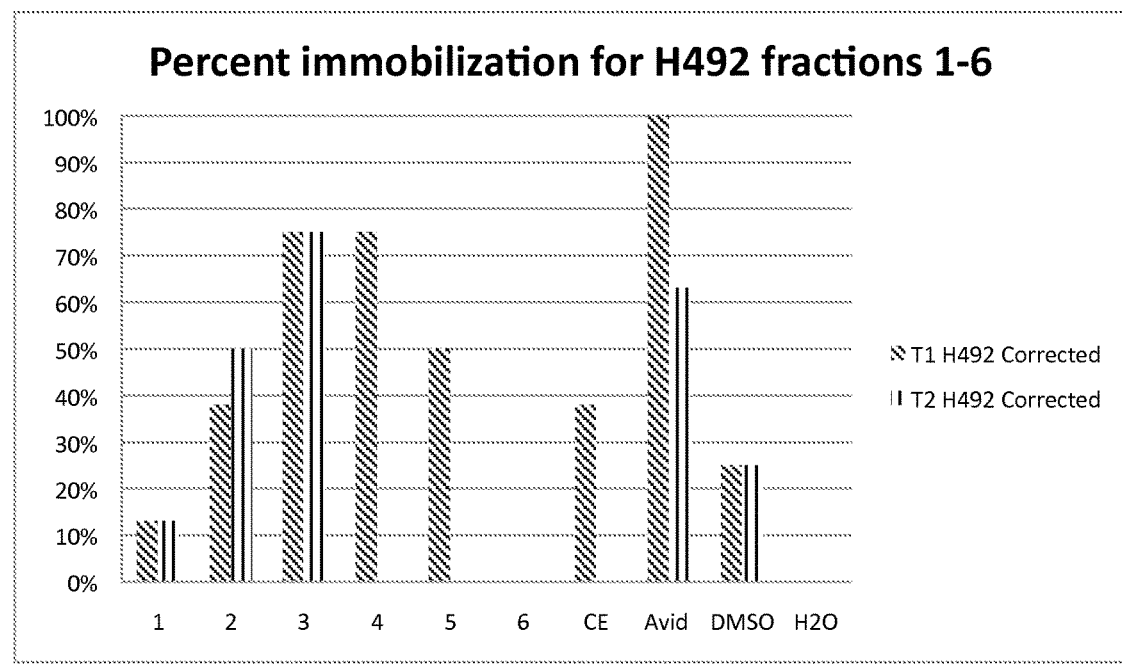

The nematicidal active compound 1-(4-hydroxyphenyl) pent-1-en-3-one (1) was obtained from fraction 3 (see FIG. 22).

Purification of Compounds

Purification of 1-(4-hydroxyphenyl) pent-1-en-3-one (1) was performed by using HPLC C-18 column (Phenomenex, Luna 10u C18(2) 100 A, 250×10), water:acetonitrile gradient solvent system (0-10 min, 80-75% aqueous $CH_3CN$; 10-45 min, 75-60% aqueous $CH_3CN$; 45-55 min, 60-50% aqueous $CH_3CN$; 55-65 min, 50-100% aqueous $CH_3CN$; 65-70 min, 100% $CH_3CN$; 55-70 min, 0-80% aqueous $CH_3CN$) at 2.5 mL/min flow rate and UV detection of 210 nm. The active compound 1-(4-hydroxyphenyl) pent-1-en-3-one (1), has retention time 60.81 min.

Mass Spectroscopy Analysis of Compounds

Mass spectroscopy analysis of active peak is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5μ 100 A column (Phenomenex). The solvent system consisted of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 μL and the samples are kept at room temperature in an auto sampler. Compound 1 has a retention time of 11.31 min under this condition. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The 1-(4-hydroxyphenyl) pent-1-en-3-one (1) has a molecular mass of 175.35 in negative ionization mode.

NMR Spectroscopy Analysis of Compounds

NMR-NMR spectra were measured on a Bruker 600 MHz gradient field spectrometer. The reference is set on the internal standard tetramethylsilane (TMS, 0.00 ppm).

Figure 21:
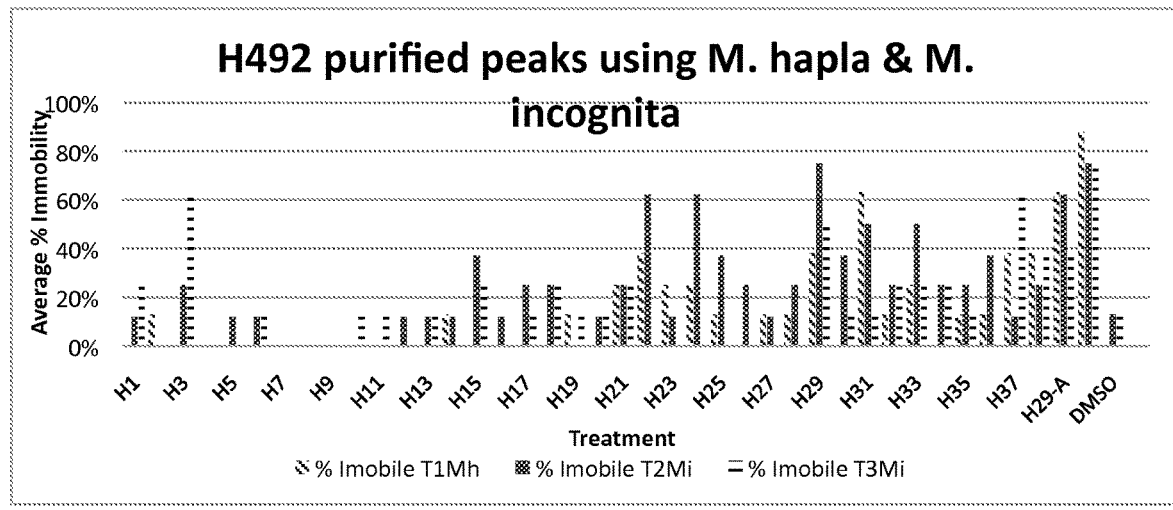
FIGS. 21 and 22 depicts the results of bioassays of various H492 (MBI-302) fractions.

For structure elucidation, the purified 1-(4-hydroxyphenyl) pent-1-en-3-one (1) with molecular weight 176 (see FIG. 21 indicated as treatment H29) is further analyzed using a 600 MHz NMR instrument, and has $^1$H NMR δ values at 7.60, 7.52, 6.83, 6.68, 2.74, 1.14 and has $^{13}$C NMR values of 203.96, 161.90, 131.78, 131.78, 145.11, 127.28, 123.83, 117.24, 117.24, 34.52, 8.89. The active compound was isolated as a light yellow solid, with UV absorption at 232 & 318 nm and analyzed for the molecular formula $C_{11}H_{12}O_2$ (6 degrees of unsaturation), by ESI mass spectrometry. The $^1H$ NMR spectrum exhibited signals for a pair of trans-coupled α,β-unsaturated olefinic protons (δ 7.60 & 6.68, each 1H, d, J=16.7 Hz) together with an $A_2B_2$-type aromatic signals at δ 7.52, 2H d, J=8.5 Hz, and 6.83, 2H d, J=8.5 Hz. Furthermore, the $^1H$ NMR spectrum revealed the presence of —$CH_2$—$CH_3$ group, at δ 2.74, 2H, q, J=7.3 Hz, and 1.14, 3H, t, J=7.3 Hz. From an analysis of the foregoing spectral data, the structure of the aromatic polyketide was established as 1-(4-hydroxyphenyl) pent-1-en-3-one, which was confirmed by detail analysis of the COSY, HMQC and HMBC experiments. A literature search revealed that this compound has been reported as an unnatural $C_5$-$C_6$ aromatic polyketide formed from the enzymatic reaction by plant type III polyketide synthases (Abe et al., 2002). Potency of the compound of interest in fraction 3 (F3) was confirmed in an in vitro assay using *M. incognita* and *M. hapla*.

In Vitro Testing in Search of Active Fraction of *Flavobacterium* spp. Extracts

Once the crude extract has been fractionated through liquid chromatography as described above, the fractions are dissolved in dimethylsulfoxide (DMSO). After the fractions are in liquid form, they are tested in an in vitro 96-well plastic cell-culture plate in order to identify the fractions that contain the desired active metabolite/s. Here, 15-20 nematodes in a 50 μl water solution are exposed to 100 μl of a 4 mg/ml fraction concentrate for a 24 hour period at 25° C. Once the incubation period is completed, results are recorded based on a visual grading of motility of J2s in each well treated with H492 fractions of 1 to 6, each treatment is tested in four replicates. FIG. 22, shows the results of two different 96-well plate bioassays of H492 of fractions 1 to 6 and crude extract (CE). Three controls are included in each trial; one positive (1% avid) and two negative controls (DMSO and water). Trial 1 (T1) was carried out using free living nematodes and the fractions were dissolved in 100% DMSO and trial 2 (T2) was carried out using *M. hapla* nematodes and the fractions were dissolved in 50% DMSO (50% DMSO: 50% water).

In Vitro Testing in Search of Active Compound in Fraction 3 of *Flavobacterium* sp. Extract Once the purification of fraction 3 is complete and all of the desired peaks/compounds are collected as described above, each peak is tested in an in vitro 96-well plastic cell-culture plate extract bioassay in order to identify the peak/s that contain the desired active metabolite/s.

15-20 nematodes in a 50 ml water solution are exposed to 3 ml of a 20 mg/ml peak concentrate (1.13 mg/ml total exposure) for a 24 hour period at 25° C. Once the incubation period is completed, results are recorded based on a visual grading of immotility of the J2s in each well treated with H492 purified peaks of H1 to H39, plus H29-A derived from fraction 3, each treatment is tested in four replicates. Three controls are included in each trial; one positive control (1% avid). and two negative controls (DMSO and water). Trial 1 (T1) was carried out using the method described above with *M. hapla*, trial 2 and 3 (T2 and T3) were carried out using the latter method with *M. incognita* (FIG. 22).

Example 6: Confirmation of the Structure of Natural Product by Synthesis

The structure of the active nematicidal compound 1 was assigned mainly based on analysis of the spectral data ($^1H$, $^{13}C$ & 2D NMR and MS). This assigned structure was now confirmed by a short and simple one step synthesis (Kad et. al., 1998). The $^1H$, $^{13}C$ NMR, MS spectra and RT on the HPLC matches exactly with that of the natural product isolated from *Flavobacterium* sp.

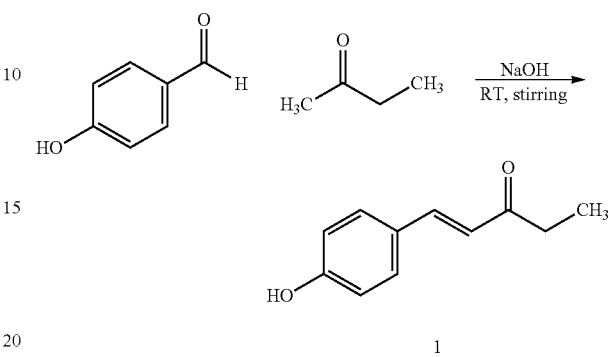

Synthesis of 1-(4-hydroxyphenyl)pent-1-en-3-one (1)

To a solution of 4-hydroxybenzaldehyde (250 mg, 2.04 mmol) in 10% NaOH (5 mL) was added 2-butanone (1.12 mL, 12 mmol) at 25° C. followed by remaining 10% NaOH solution (7 mL) in round bottle flask and stirred for about 90 min at RT. The reaction mixture was acidified with 10% HCl solution and extracted with ethyl acetate (2×200 mL). The combined organic extracts were dried and evaporated to obtain crude product which was then purified using silica gel column chromatography to give compound 1, 150 mg. The spectral data matches exactly as reported above for natural product.

Testing of Polyketide 1 (MW 176) to Control Nematodes

Dose Response % Immotility for Synthesized Polyketide MW176

Figure 23:
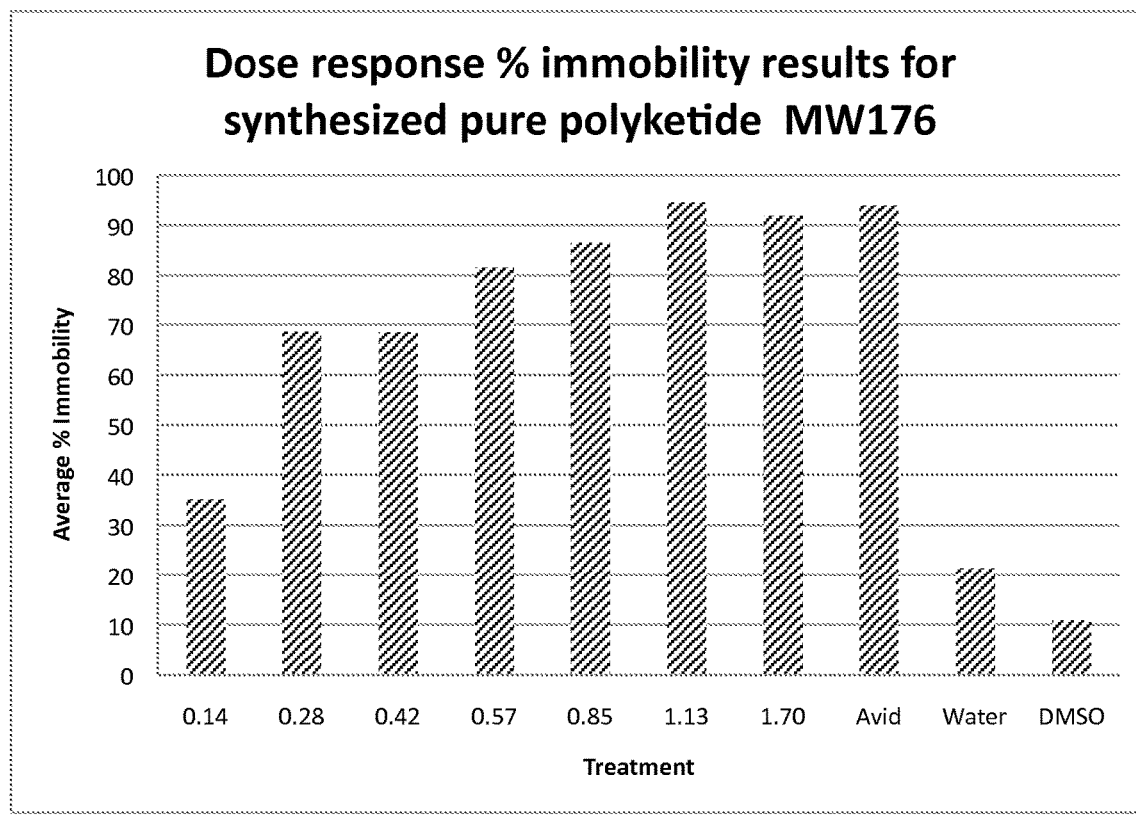
FIG. 23 shows the effect of dose response of H492 (MBI-302) on % immobilization (immotility).

The synthetic polyketide (MW 176) was tested at several doses (concentrations tested were 0.14, 0.28, 0.42, 0.56, 0.84, 1.13, 1.69 mg/mL of polyketide in DMSO) in the 6-well plate immobility bioassay to find the optimal dose of this compound needed in order to detect nematicidal activity. In this particular assay the nematode juveniles (J2) of *M. incognita* (Monsanto strain) were first exposed to the tested samples in 96-well plate: 50 μl of water containing approximately 300 J2 were mixed with 3 μl of polyketide sample or controls (avid (2%) as positive control or DMSO and water as negative controls, respectively. After 24 h incubation, 20 μl of J2 suspension from each well was transferred into the wells of 6-well plates filled with water agar (3 mL of 1% agar per each well). The plates were left open for 10-15 min to allow the solutions to dry out. Afterwards, circles were drawn around the J2 suspension and initial numbers of J2 inside the circles were counted under the stereomicroscope. The plates were incubated for another 24 h and the numbers of J2 that remained immotile (i.e. were still present inside the circles) were counted using stereomicroscope. The % of nematode immotility was expressed as: [(number of immotile nematodes after 24 h incubation/initial number of J2)*100%]. The data in FIG. 23 suggest that for good nematicidal activity the optimal range required was ≥0.5 mg/mL.

Testing of Polyketide 1 (MW 176 Compound) in Pot Testing for Nematicidal Control The nematicidal activity of polyketide 1 (MW 176 compound) against root-knot nematodes was further assessed in greenhouse in cone tests using *M. incognita* and tomato (cv. UC82) as a host. The tomato seeds were germinated in vermiculate and 3-week-old seedlings were transferred to the cones containing mixture of sand and top soil (1:1). Two weeks after transplanting, tomato plants were treated with the samples. The yield of polyketide (MW 176) in the V-8 media was found to be around 1 mg/mL, so the testing of the polyketide was calculated based on the isolated yield of the active compound. Four different concentrations (100, 10, 1, & 0.1 µg/mL) of the polyketide prepared in 4% methanol (MeOH) were dosed as 10 mL of soil drench into each pot. Each treatment was tested in 5 replicates. Following the drench each pot was inoculated with 1000 nematode eggs suspended in 1 mL of water. The dosing of the product was repeated after two weeks. Three weeks later, the inoculation test was terminated and the following parameters were scored: number of galls/root, gall index and fresh top weight.

Figure 24:
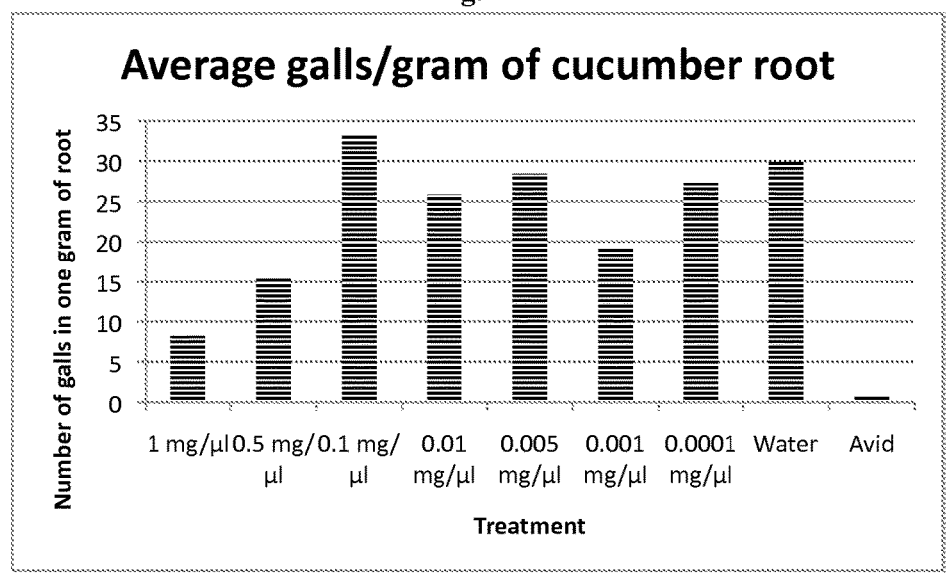
FIG. 24 shows the effect of polyketide 1 on the number of galls/root.
Figure 25:
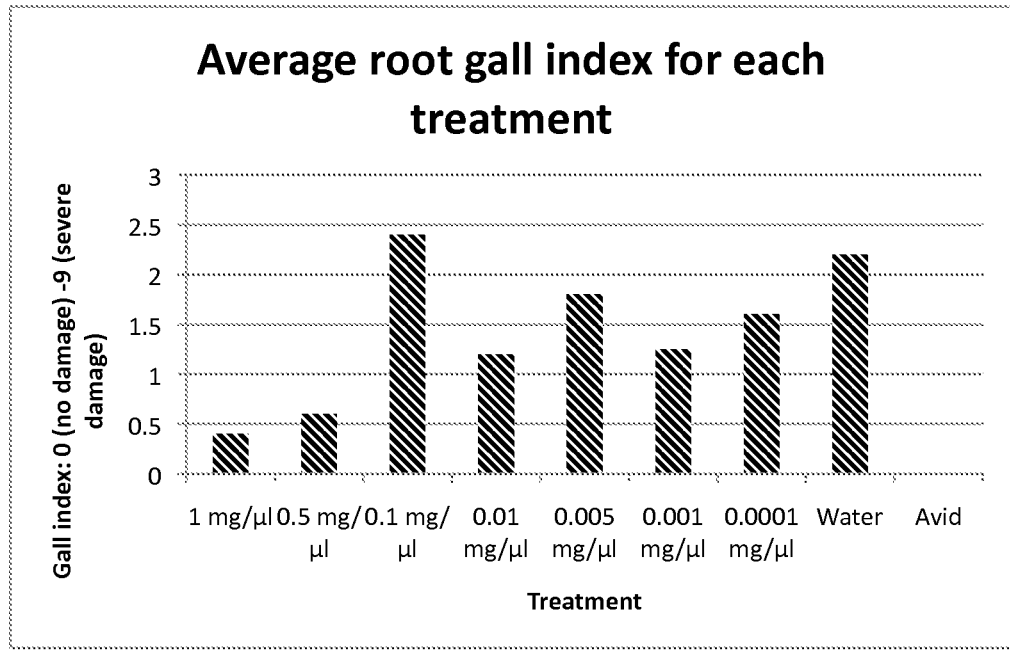
FIG. 25 shows the effect of polyketide 1 on gall index.
Figure 26:
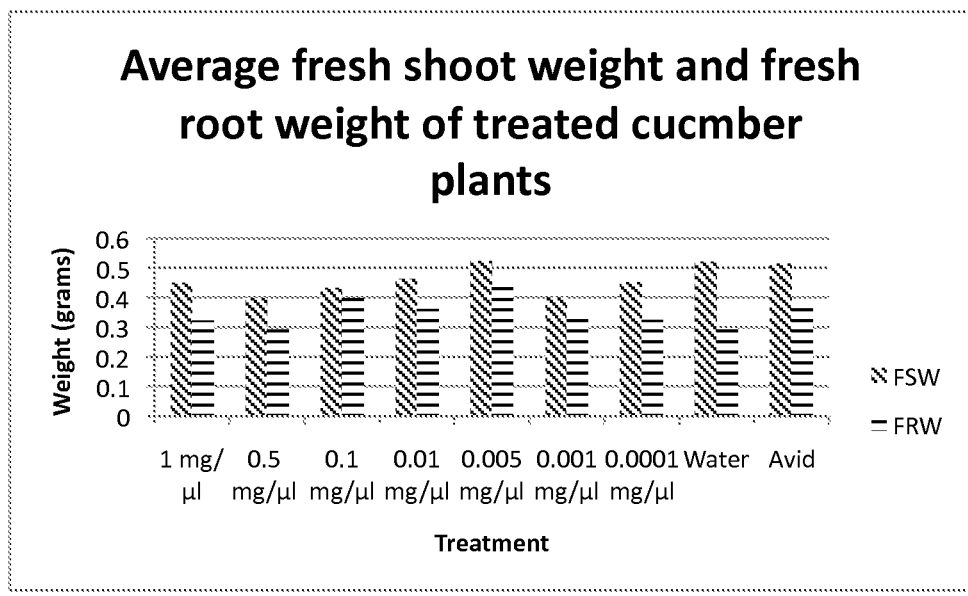
FIG. 26 shows the effect of polyketide 1 on fresh top weight.

The results on effect of polyketide 1 on the number of galls/root, gall index and fresh top weight are shown in FIGS. 24-26.

The results from these experiments indicate:

- 0.001 & 0.01 mg/ml of polyketide significantly reduced the gall index and galls per root in the $1^{st}$ test compared to water control.
- 0.1 mg/ml of polyketide only significantly reduced the gall index in the $1^{st}$ test, and all tested dilutions in the $2^{nd}$ test compared to water control.
- 4% methanol as the solvent of polyketide neither caused phytotoxicity to tomato (cv. UC82) nor reduced the damage of the nematodes in the $1^{st}$ test; and 3% methanol reduced the gall index in the $2^{nd}$ test without phytotoxicity effect in the $2^{nd}$ test.

Structure-Activity Relationship (SAR)

To quickly understand which part of the 1-(4-hydroxyphenyl) pent-1-en-3-one (1) molecule (polyketide) plays a crucial role on the nematicidal activity, a series of structural analogues were synthesized and evaluated using motility test. This bioassay serves to distinguish the differences in efficacy by measuring the recovery and the mobility of the nematodes after being exposed to any given compound with 6 repetitions per treatment. This bioassay involves the following procedure: 3 µL (at 20 mg/ml) of the sample are dispensed into 50 µl of approximately 300 J2's in a 96-well plastic cell-culture plate. After 24 hours, 100-150 of the treated J2's were transferred into 6-well plates that contain 1.5% water agar. After drying of the test sample on the agar, the initial drop was marked and initial counts of the J2's were carried out. After another 24 hour recovery period, the immobilization of the juveniles were measured by counting the number of J2's that moved from the initial circle and an average of the 6 repetitions were calculated to get the percent immobilization of each sample. The results are summarized in Table 12.

TABLE 12

Nematicidal Activity of Various Synthetic Analogues of Polyketide 1 Using Motility Bioassay.

| Samples | Compound ID | Average % immobility |
|---|---|---|
| SAR-1 | 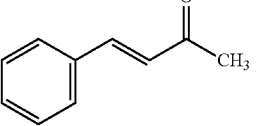<br>(E)-4-phenylbut-3-en-2-one | 99 |
| SAR-2 | 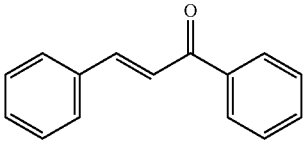 [SMILES: O=C(/C=C/c1ccccc1)c1ccccc1]<br>Benzalacetophenone | 4 |
| SAR-3 | 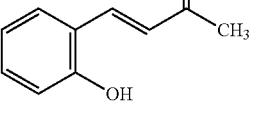<br>(E)-4-(2-hydroxyphenyl)but-3-en-2-one | 95 |
| SAR-4 | 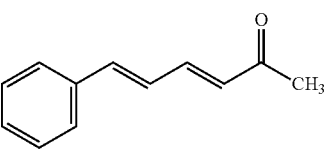<br>(3E,5E)-6-phenylhexa-3,5-dien-2-one | 97 |
| SAR-5 | 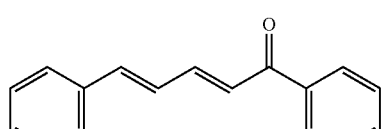<br>(2E,4E)-1,5-diphenylpenta-2,4-dien-1-one | 98 |
| SAR-6 | 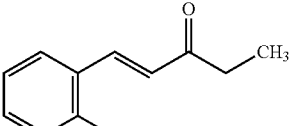<br>(E)-1-(2-hydroxyphenyl)pent-1-en-3-one | 98 |
| SAR-7 | 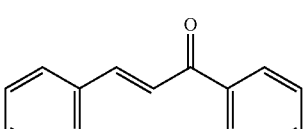<br>(E)-3-(2-hydroxyphenyl)-1-phenylprop-2-en-1-one | 99 |

TABLE 12-continued

Nematicidal Activity of Various Synthetic Analogues of Polyketide 1 Using Motility Bioassay.

| Samples | Compound ID | Average % immobility |
|---|---|---|
| SAR-8 | (E)-1-(2-hydroxyphenyl)-5-methylhex-1-en-3-one | 100 |
| SAR-9 | (E)-3-(4-hydroxyphenyl)-1-phenylprop-2-en-1-one | 100 |
| SAR-10 | (E)-1-(4-hydroxyphenyl)-5-methylhex-1-en-3-one | 96 |
| SAR-11 | (E)-4-(3-hydroxyphenyl)but-3-en-2-one | 99 |
| SAR-12 | (E)-4-(2-hydroxyphenyl)but-3-en-2-one | 99 |
| SAR-13 | 2-(2'-phenyl-2-oxoethoxy) benzaldehyde | 74 |
| SAR-14 | (E)-4-(2-hydroxyphenyl)-3-methylbut-3-en-2-one | 97 |
| SAR-15 | (E)-1-phenylpent-2-en-1-one | 20 |
| SAR-16 | (3E,7Z)-deca-3,7-dien-2-one | 94 |
| SAR-17 | (E)-4-(3-hydroxyphenyl)but-3-en-2-one | 98 |
| SAR-18 | (1E,4E)-1,5-bis(3-hydroxyphenyl)penta-1,4-dien-3-one | 23 |
| SAR-19 | (E)-1,4-diphenylbut-2-en-1-one | 64 |
| SAR-20 | (E)-1-(4-hydroxyphenyl)-4-phenylbut-2-en-1-one | 28 |
| SAR-21 | (1E,4E)-1,5-bis(3-hydroxyphenyl)-2-methylpenta-1,4-dien-3-one | 12 |

TABLE 12-continued

Nematicidal Activity of Various Synthetic Analogues of Polyketide 1 Using Motility Bioassay.

| Samples | Compound ID | Average % immobility |
|---|---|---|
| SAR-22 | 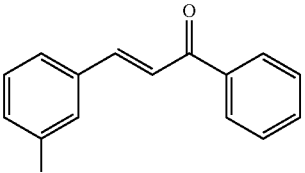<br>(E)-3-(3-hydroxyphenyl)-1-phenylprop-2-en-1-one | 70 |
| SAR-23 | 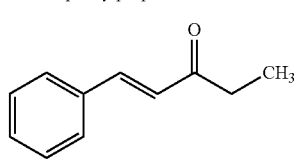<br>(E)-1-phenylpent-1-en-3-one | 80 |
| SAR-24 | 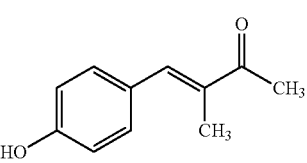<br>(E)-4-(4-hydroxyphenyl)-3-methylbut-3-en-2-one | 80 |
| SAR-25 | 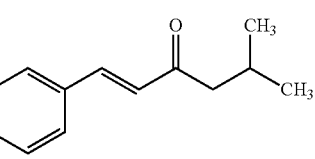<br>(E)-5-methyl-1-phenylhex-1-en-3-one | 79 |
| SAR-26 | 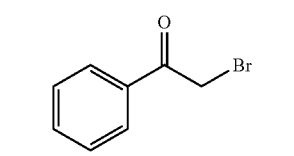<br>2-bromo-1-phenylethanone | 50 |
| SAR-27 | 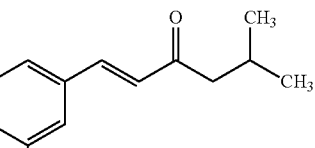<br>(E)-1-(3-hydroxyphenyl)-5-methylhex-1-en-3-one | 78 |
| SAR-28 | 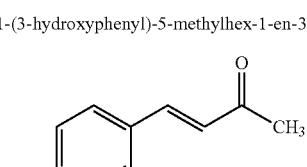<br>(E)-4-(4-hydroxyphenyl)but-3-en-2-one | 78 |

TABLE 12-continued

Nematicidal Activity of Various Synthetic Analogues of Polyketide 1 Using Motility Bioassay.

| Samples | Compound ID | Average % immobility |
|---|---|---|
| SAR-29 | 3-hydroxybenzaldehyde | 70 |
| SAR-30 | 4-hydroxybenzaldehyde | 58 |
| SAR-31 | 2-hydroxybenzaldehyde | 58 |
| SAR-32 | Benzaldehyde | 65 |
| SAR-33 | γ-dodecalactone | 63 |
| SAR-34 | γ-octalactone | 21 |
| SAR-35 | 2-octanone | 33 |
| SAR-36 | 2-heptanone | 21 |
| SAR-37 | 2-undecanone | 67 |
| SAR-38 | cis-4-heptenal | 21 |
| SAR-39 | 4-methyl-2-pentanone | 54 |
| SAR-40 | iso-butyraldehyde | 79 |
| SAR-41 | 4-hydroxy-4-methylpentanone | 21 |
| SAR-42 | o-anisaldehyde | 8 |
| SAR-43 | 2-butanone | 21 |
| DMSO | | 9 |
| Water | | 8 |
| Avid | | 99 |

Antimicrobial Activity

The pure 1-(4-hydroxyphenyl) pent-1-en-3-one (1) "polyketide MW 176" was tested against various microbial pathogens using agar disc assay. The compound 1 showed potent activity against *Erwinia amylovora* and moderate activity against *Bacillus cereus, Xanthomonas campestris*, and *Avidovorax avenae* subsp. *citrulli*.

Deposit of Biological Material

The following biological material has been deposited under the terms of the Budapest Treaty with the Agricultural Research Culture Collection (NRRL), 1815N. University Street, Peoria, Ill. 61604, USA, and given the following number:

| Deposit | Accession Number | Date of Deposit |
|---|---|---|
| *Flavobacterium* sp.H492 | NRRL B-50584 | Oct. 14, 2011 |

The strain has been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

This invention may be embodied in other forms or carried out in other ways without departing from the spirit or essential characteristics thereof. The present disclosure is therefore to be considered as in all aspects illustrate and not restrictive, and all changes which come within the meaning and range of equivalency are intended to be embraced therein.

Various references are cited throughout this specification, each of which is incorporated herein by reference in its entirety.

REFERENCES

Abe, I., Takahashi, Y., Noguchi, H. (2002), "Enzymatic formation of an unnatural C6-O5 aromatic polyketide by plant type III polyketide synthases", *Org. Lett.* 4, 3623-3626.

Asolkar, R. N., Jensen, P. R., Kauffman, C. A., Fenical, W. (2006), Daryamides A-C, "Weakly Cytotoxic Polyketides from a Marine-Derived Actinomycete of the Genus *Streptomyces* strain CNQ-085", *J. Nat. Prod.* 69:1756-1759.

Arena, J. P., Liu, K. K. et al. (1995), "The mechanism of action of avermectins in *Caenorhabditis elegans*-correlation between activation of glutamate-sensitive chloride current, membrane binding and biological activity", *Journal of Parasitology* 81: 286-294.

Aspelin, A. L., Grube, A. H. (1999). Pesticides Industry Sales and Usage, 1996 and 1997. U. S. E. P. Agency. Publication 733-R-99-001.

Bakhetia, M., Charlton, W. et al. (2005). "RNA interference of dual oxidase in the plant nematode *Meloidogyne incognita*", *Molecular Plant-Microbe Interactions* 18: 1099-1106.

Barnsley, E. A. (1988), "Metabolism of 2,6-dimethylnaphthalene by *Flavobacteria*", *Appl. Environ. Microbiol.* 54: 428-433.

Bernardet, J.-F. and Nakagawa, Y. (2006a), "An introduction to the Family Flavobacteriaceae", Prokaryotes 7:455-480.

Bernardet, J.-F. and Bowman, J. (2006b), "The Genus *Flavobacterium*", Prokaryotes 7:481-531.

Bodour, A. A. Guerrero-Barajas, C Beth V. Jiorle, B. V., Malcomson, M. E., Paull, A. K., Somogyi, A., Trinh, L. N, Bates, R. B. and Maier, R. M. (2004) "Structure and Characterization of Flavolipids, a Novel Class of Biosurfactants Produced by *Flavobacterium* sp. Strain MTN11", *Appl. Environ. Microbiol.* 70:114.

Bridge, J. & Page, S. L. J. 1980. Estimation of root-knot nematode infestation levels on roots using a rating chart. Tropical Pest Management. 26(3): 296-298.

Cashion P, Holderfranklin M A, McCully J, Franklin M. 1977. RAPID METHOD FOR BASE RATIO DETERMINATION OF BACTERIAL DNA. Analytical Biochemistry 81:461-466.

Chalvet-Monfray, K., P. Sabatier, et al. (1996), "Synergy between deltamethrin and prochloraz in bees: Modeling approach", *Environmental Toxicology and Chemistry*, 15(4): 525-534.

Chitwood, D. J. (2003). Nematicides. Encyclopedia of Agrochemicals, vol 3. J. R. Plimmer. New York, John Wiley & Sons. 3: 1104-1115.

Chitwood, D. J. (2002). "Phytochemical based strategies for nematode control", *Annual Review of Phytopathology* 40: 221-249.

Colby, S. R. (1967), "Calculating Synergistic and Antagonistic Responses of Herbicide Combinations", *Weeds* 15(1): 20-22.

Deley J, Cattoir H, Reynaert. A. 1970. Quantitative measurement of dna hybridization from renaturation rates. European Journal of Biochemistry 12:133.

Dinaburg, A. G. 1942. "The efficiency of the Baermann apparatus in the recovery of *Haemonchus contortus*", *J. Parasitol.* 28:433-440.

Dickschat J. S., Helmke, E., Schulz, S. (2005), "Volatile organic compounds from arctic bacteria of the *Cytophaga-Flavobacterium-bacteroides* group: A Retrobiosynthetic approach in chemotaxonomic investigations", *Chemistry & Biodiversity* 2: 318-353.

Dong, L. Q. and Zhang, K. Q. (2006) "Microbial control of plant-parasitic nematodes: a five-party interaction". *Plant Soil* 288: 31-45.

Farenhorst, M., B. and Knols, G. J. et al. (2010), "Synergy in Efficacy of Fungal Entomopathogens and Permethrin against West African Insecticide-Resistant *Anopheles gambiae* Mosquitoes." *PLoS ONE* 5(8): e12081.

Ferezou, J-P., and Julia, M. (1985), "Biomimetic synthesis of bacterial C50 carotenoids decaprenoxanthin and C.P. 450", *Tetrahedron* 41: 1277-1287.

Francis, G. W., Hertzberg, S., Andexsen, K., Liaaen-Jensen, S. (1970), "New carotenoid glycosides from *Oscillatorza limosa*", *Phytochemistry* 9:629-635.

Hallman, J. and Sikora, R. A. (1996). "Toxicity of fungal endophyte secondary metabolites to plant-parasitic nematodes and soil-borne pathogens", *Journal of Plant Pathology* 102: 155-162.

Hasky-Gunther, K., Hoffman-Hergarter, S. et al. (1998). "Resistance against potato cyst nematode *Globodera pallida* systemically induced by the rhizobacteria *Agrobacterium radiobacter*(G12) and *Bacillus spaericus* (B43)" *Fundamentals of Applied Nematology* 21: 511-517.

Hummelbrunner, L. A. and Isman, M. B. (2001). "Acute, Sublethal, Antifeedant, and Synergistic Effects of Monoterpenoid Essential Oil Compounds on the Tobacco Cutworm, *Spodoptera litura* (Lep., Noctuidae)," *Journal of Agricultural and Food Chemistry* 49(2): 715-720.

Huss et al. 1983. Studies on the spectrophotometric determination of dna hybridization from renaturation rates. Systematic and Applied Microbiology 4:184-192.

Jaffee, B. A. and Muldoon, A. E. (1995). "Susceptibility of root-knot and cyst nematodes to the nematode-trapping fungi *Monocrosporium ellipsosporum* and *M. cionopagum*." *Soil Biology and Biochemistry* 27: 1983-1090.

Kad, G. L.; Singh, V.; Khurana, A.; Singh, J. (1998). The Synthesis of Phycopsisenone, a New Phenolic Secondary Metabolite from the Sponge *Phycopsis* sp. *J. Nat. Prod.* 1998, 61, 297-298.

Kamiyama, T., Umino, T., Satoh, T., Sawairi, S., Shirane, M., Ohshima, S., Yokose, K., (1995). "Sulfobacins A & B, novel von Willebrand factor receptor antagonists I. production, isolation, characterization and biological activities", *J. Antibiot.*, 48: 924-928.

Kaplan, C. W. and Kitts, C. L. 2004. Bacterial Succession in a petroleum land treatment unit. Appl. Environ. Microbiol. 70:1777-1786

Kato, H., Haishima, Y., Iida, T., Tanaka, A., Tanamoto, K., (1998), "Chemical structure of lipid A isolated from *Flavobacterium meningosepticum lipopolysaccharide*", *J. Bact.* 180:3891-3899.

Kerry, B. R. (2001). Exploitation of the nematophagous fungal *Verticillium chlamydosporium* Goddard for the biological control of root-knot nematodes (*Meloidogyne* spp.) *Fungi as biocontrol agents: Progress, problems and potential*. T. M. Butt, C. Jackson and N. Magan. New York, CAB International: 155-168.

Kim, O. S., Cho, Y. J., Lee, K., Yoon, S. H., Kim, M., Na, H., Park, S. C., Jeon, Y. S., Lee, J. H., Yi, H., Won, S., Chun, J. (2012). Introducing EzTaxon-e: a prokaryotic 16S rRNA Gene sequence database with phylotypes that represent uncultured species. Int J Syst Evol Microbiol 62, 716-721.

Kirkegaard, J. A. and Sarwar, M. (1998). "Biofumigation potential of brassicas", *Plant and Soil* 201: 71-89.

Kobayashi, J., Mikami, S., Shigemori, I., Iakaoa, I., Shimonishia, Y., Izutah, S., Yoshidab, S., (1995), "Flavocristamides A and B, new DNA polymerase α inhibitors from a marine bacterium", *Flavobacterium* sp., *Tetrahedron*, 51: 10487-10490.

Koenning, S. R., Overstreet, C. et al. (1999). "Survey of crop losses in response to phytoparasitic nematodes in the United States for 1994." *Journal of Nematology* 31: 587-618.

Kokalis-Burelle, N. and Rodriquez-Kabana, R. (2006). Allelochemicals as biopesticides for management of plant-parasitic nematodes. *Alleolochemicals: Biological Control of Plant Pathogens and Diseases*. I. Mukerji and K. G. Mukerji. Netherlands, Springer: 15-29.

Krieg, A., A. and Huger, M. et al. (1983), "*Bacillus thuringiensis* var. tenebrionis: Ein newer, gegenuber Larven von Coleopteren wirksamer Pathotyp", Z. Angew. Entomol. 96: 500-508.

Liaaen-Jensen, S., Hertzberg, S., Weeks, O. B., Schwieter, U. (1968), "Bacterial carotenoids XXXVIII. $C_{50}$-Caeotenoids. 3. Structure determination of dehydrogenans-P439", *Acta Chem. Stand.*, 22: 1171-1186.

Lorch, H et al. "Basic methods for counting microoganisms in soil and water. In *Methods in applied soil microbiology and biochemistry*. K. Alef and P. Nannipieri. Eds. San Diego, Calif., Academic Press: pp. 146-161. 1995.

Marrone, P. G., Manker, D. C. et al. (1998). Nematicidal *Bacillus* strain and metabolite and methods thereof. U.S. Pat. No. 5,733,544. USA.

Meunier, L., Carubel, P. et al. (1999), "Insecticidal combinations including an insecticide from the family chloronicotinyl family and an insecticide having pyrazole, pyrrole, or phenylimidazole group. U. States"., United States, Rhone-Poulene Agrochimie: 6.

Meyer, S. L. F. and Roberts, D. P. (2002). "Combinations of biocontrol agents for management of plant-parasitic nematode and soilborne plant-pathogenic fungi" *Journal of Nematology* 34: 1-8.

Oka, Y., Nacar, S. et al. (2000). "Nematicidal activity of essential oils and their components against root-knot nematode", *Phytopathology* 90:710-715.

Oostendorp, M. and Sikora, R. A. (1990). "In-vitro interrelationships between rhizosphere bacteria and *Heterodera schachtii*" *Reviews in Nematology* 13: 269-274.

Pederson, M. and Woldum, H. S. Synergistic Combination of Glutamate-and-Gaba-Gated Chloride Against Pesticide and at Least One Vitamin E, Niacin, or Derivatives Thereof, US Patent Appln. Pub. No. 2009/0111579, published Apr. 30 2009.

Puritch, G. and Salloum, G. Environmentally Safe Insecticide, U.S. Pat. No. 5,047,424, issued Sep. 10, 1991.

Quarles, W. (2005). "2005 Directory of least toxic pest control products", The *IPM Practitioner* 26: 17.

Roubtsova, T., J.-A. Lopez-Perez, et al. (2007). "Effect of broccoli (*Brassica oleracea*) tissue, incorporated at different depths in a soil column, on *Meloidogyne incognita*", *Journal of Nematology* 39: 111-117.

Sasser, J. N. and Freckman, D. W. (1987). "A world perspective on nematology: the role of the society". In J. A. Veech and D. W. Dickson (Eds.), *Vistas on Nematology* (pp. 7-14). Society of Nematologists, Hyattesville.

Saxena, A. K., Pal, K. K. et al. (2000). Bacterial biocontrol agents and their role in plant disease management. *Biocontrol potential and its exploitation in sustainable agriculture: crop diseases, weeds and nematodes*. R. R. Upadhaya, K. G. Mekerji and B. P. Chamola. New York, Kluwer Academy Plenum.

Shapiro-Ilan, D. I., and Cottrell, T. E. et al. (2011), "Effects of combining microbial and chemical insecticides on mortality of the Pecan Weevil (Coleoptera: Curculionidae)," *J Econ Entomol*. 104(1): 14-20

Shoji, J., Kato, T., Sakazaki, R., Nagata, W., Terul, Y., Nakagawa, Y., Shiro, M., Matsumoto, K., Hattori., T., Yoshida, T., Kondo, E., (1984), "Chitinovorins A, B and C, novel lactam antibiotics of bacterial origin", *J. Antibiot.*, 37; 1486-1490.

Shoji, J., Sakazaki, R., Kato, T, Terui, Y., Matsumoto, K., Tanimoto, T., Hattori, T., Hirooka, K., Kondo, E., (1985), "Isolation of chitinovorins D", *J. Antibiot.*, 38: 538-540.

Siddiqui, M. A. and Alam, M. M. (2001). Nematicides. *The IPM practitioner* 9-11.

Siddiqui, Z. A. and Mahmood, I. (1999). "Role of bacteria in the management of plant parasitic nematodes: a review." *Bioresource Technology* 69: 167-179.

Siddiqui, M. A. and Mahmood, I. (1996). "Biological control of plant parasitic nematodes by fungi: a review." *Bioresource Technology* 58: 229-239.

Sikora, R. A. and Hoffman-Hergarter, S. (1993). Biological control of plant-parasirtic nematodes with plant health promiting rhizobacteria. *Biologically based technology*. P. D. Lumsden and J. L. Vaugh. USA, ACS Symposium Series: 166-172.

Singh P. D., Young, M. G., Johnson, J. H., Cimarusti, C. M. Sykes, R. B., (1984), "Bacterial production of 7-formamidocephalosporins", Isolation and structure determination", *J. Antibiot*. 37: 773-780.

Terefe, M. and Tefera, T. et al. (2009). "Effect of a formulation of *Bacillus firmus* on root-knot nematode *Meloidogyne incognita* infestation and the growth of tomato plants in the greenhouse and nursery." *Journal of Invertebrate Pathology* 100: 94-99.

Thompson, G. D. and Dutton, R. et al. (2000). "Spinosad—a case study: an example from a natural products discovery programme," Pest Management Science 56: 696-702.

Wayne L G, Brenner D J, Colwell R R, Grimont P A D, Kandler O, Krichevsky M I, Moore L H, Moore W E C, Murray R G E, Stackebrandt E, Starr M P, Truper H G. 1987. Report of the ad-hoc-committee on reconciliation of approaches to bacterial systematics. International *Journal of Systematic Bacteriology* 37:463-464.

Whitehead, A. G. (1998). *Plant nematode control*. Wallingford, UK, CAB International.

Wirth, M. C., J. A. Jiannino, et al. (2004), "Synergy between Toxins of *Bacillus thuringiensis* subsp. israelensis and *Bacillus sphaericus*." *Journal of Medical Entomology* 41: 935-941.

Yagi, H. and Maruyama, A., (1999), "A novel monoacyl-diglycosyl-monoacylglycerol from *Flavobacterium marinotypicum*", *J. Nat. Prod*. 62" 631-632.

Yokoyama, A., Izumida, H., Shizuri, Y., (1996). New carotenoids sulfates isolated from a marine bacterium, *Biosci. Biotech. Biochem.*, 60: 1877-1978.

Yokoyama A. and Miki, W., (1995), Isolation of myxol from a marine bacterium *Flavobacterium* sp. associated with a marine sponge. *Fisheries Sci*. 61:684-686.

Zeck W. M. (1971), Ein Bonitierungsschema zur Feldauswertung von Wurzelgallenbefall. Pflanzenschutznachrichten Bayer 24, 1: 144-147.

What is claimed is:

1. A composition comprising
   (a) a whole cell broth collected from *Flavobacterium* sp. H492 (NRRL Accession No. B-50584) agitated fermentation, and
   (b) a carrier, diluent, surfactant or adjuvant;
   wherein said composition has pesticidal or plant growth modulating activity.

2. The composition according to claim 1, further comprising at least one or more second substances, wherein said second substance is a chemical or biological pesticide or growth promoting agent.

3. The composition according to claim 2, wherein said second substance is a pesticide selected from the group consisting of nematicide, fungicide and insecticide.

4. A method for modulating pest infestation in a plant and/or modulating growth of a plant comprising applying to the plant and/or seeds thereof and/or substrate used for growing said plant an amount of:
   (A) the composition of claim 1; and/or
   (B) the composition of claim 2.

5. The method according to claim 4, wherein said pest is a nematode pest.

6. The method according to claim 4, wherein said plant is selected from the group consisting of strawberry, squash, cucumber, tomato, rose, pepper, cucumber, eggplant, grapevine, cotton, onion, garlic, wheat, soy, corn and rice.

7. The method according to claim 4, further comprising applying 1-(4-hydroxyphenyl) pent-1-en-3-one to said plant.

8. A method for obtaining 1-(4-hydroxyphenyl) pent-1-en-3-one from a strain of *Flavobacterium* sp. H492 (NRRL Accession No. B-50584) comprising
   (i) culturing the strain for a time sufficient to obtain a supernatant and said compound; and
   (ii) isolating the compound produced in step (i) from the supernatant.

9. A seed comprising the composition of claim 2.

10. A seed comprising the composition of claim 1.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Unknown
<220> FEATURE:
<223> OTHER INFORMATION: Forward Primer (FD1)

<400> SEQUENCE: 1
agagtttgat cctggctcag                                              20

<210> SEQ ID NO 2
<211> LENGTH: 17
<212> TYPE: DNA
<213> ORGANISM: Unknown
<220> FEATURE:
<223> OTHER INFORMATION: reverse primer RD1

<400> SEQUENCE: 2
aaggaggtga tccagcc                                                 17

<210> SEQ ID NO 3
<211> LENGTH: 1215
<212> TYPE: DNA
<213> ORGANISM: Unknown
<220> FEATURE:
<223> OTHER INFORMATION: FD1 Sequence

<400> SEQUENCE: 3
gcttaccatg cagtcgaggg gtagaattct tcggaatttg agaccggcgc acgggtgcgt     60
aacgcgtatg caatctgcct ttcacagagg gatagcccag agaaatttgg attaatacct    120
catagtatta tggagtggca tcactttata attaaagtca caacggtgaa agatgagcat    180
gcgtcccatt agctagttgg taaggtaacg gcttaccaag gcgacgatgg gtaggggtcc    240
tgagagggag atcccccaca ctggtactga gacacggacc agacttatac gggaggcagc    300
agtgaggaat attggtcaat ggacgcaagt ctgaaccagc catgccgcgt gcaggatgac    360
ggtcctatgg attgtaaact gcttttgtac gagaagaaac acctctacgt gtagagactt    420
gacggtatcg taagaataag gatcggctaa ctccgtgcca gcagccgcgg taatacggag    480
gatccaagcg ttatccggaa tcattgggtt taaagggtct gtaggcggtc tagtaagtca    540
gtggtgaaag cccatcgctc aacggtggaa cggccattga tactgctgga cttgaattat    600
taggaagtaa ctagaatatg tagtgtagcg gtgaaatgct tagagattac atggaatacc    660
aattgcgaag gcaggttact actaatggat tgacgctgat ggacgaaagc gtgggtagcg    720
aacaggatta gataccctgg tagtccacgc cgtaaacgat ggatactagc tgttgggcgc    780
aagttcagtg gctaagcgaa agtgataagt atcccacctg gggagtacgg gcgcaagcct    840
gaaactcaaa ggaattgacg ggggcccgca caagcggtgg agcatgtggt ttaattcgat    900
gatacgcgag gaaccttacc aaggcttaaa tgtagtttga ccgatttgga aacagatctt    960
tcgcaagaca aattacaagt gctgcatggt tgtcgtcagc tcgtgccgtg aggtgtcagt   1020
taagtcctat acgagcgcaa cccctgtgta gtgcagcgat tcggtcggac tctagcagac   1080
tgcagtgcaa ctgtgagaag gtgggatgac gtcgatcatc acgccttacg ctggctacca   1140
cgtgctacat gacgtacgag gacgctacct cgctagggcg aggatcttta agccggtcca   1200
cgttcgaatc gggaa                                                   1215

-continued

```
<210> SEQ ID NO 4
<211> LENGTH: 1233
<212> TYPE: DNA
<213> ORGANISM: Unknown
<220> FEATURE:
<223> OTHER INFORMATION: RD1 Sequence
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (8)..(11)
<223> OTHER INFORMATION: n is a, c, g, or t
<220> FEATURE:
<221> NAME/KEY: misc_feature
<222> LOCATION: (941)..(941)
<223> OTHER INFORMATION: n is a, c, g, or t
<220> FEATURE:
<221> NAME/KEY: misc_feature
<222> LOCATION: (986)..(986)
<223> OTHER INFORMATION: n is a, c, g, or t
<220> FEATURE:
<221> NAME/KEY: misc_feature
<222> LOCATION: (1001)..(1002)
<223> OTHER INFORMATION: n is a, c, g, or t
<220> FEATURE:
<221> NAME/KEY: misc_feature
<222> LOCATION: (1034)..(1034)
<223> OTHER INFORMATION: n is a, c, g, or t
<220> FEATURE:
<221> NAME/KEY: misc_feature
<222> LOCATION: (1038)..(1039)
<223> OTHER INFORMATION: n is a, c, g, or t
<220> FEATURE:
<221> NAME/KEY: misc_feature
<222> LOCATION: (1078)..(1078)
<223> OTHER INFORMATION: n is a, c, g, or t
<220> FEATURE:
<221> NAME/KEY: misc_feature
<222> LOCATION: (1081)..(1082)
<223> OTHER INFORMATION: n is a, c, g, or t
<220> FEATURE:
<221> NAME/KEY: misc_feature
<222> LOCATION: (1085)..(1086)
<223> OTHER INFORMATION: n is a, c, g, or t
<220> FEATURE:
<221> NAME/KEY: misc_feature
<222> LOCATION: (1094)..(1099)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1105)..(1106)
<223> OTHER INFORMATION: n is a, c, g, or t
<220> FEATURE:
<221> NAME/KEY: misc_feature
<222> LOCATION: (1113)..(1115)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1123)..(1124)
<223> OTHER INFORMATION: n is a, c, g, or t
<220> FEATURE:
<221> NAME/KEY: misc_feature
<222> LOCATION: (1130)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
```

```
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1139)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1145)..(1146)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1152)..(1154)
<223> OTHER INFORMATION: n is a, c, g, or t
<220> FEATURE:
<221> NAME/KEY: misc_feature
<222> LOCATION: (1159)..(1160)
<223> OTHER INFORMATION: n is a, c, g, or t
<220> FEATURE:
<221> NAME/KEY: misc_feature
<222> LOCATION: (1162)..(1162)
<223> OTHER INFORMATION: n is a, c, g, or t
<220> FEATURE:
<221> NAME/KEY: misc_feature
<222> LOCATION: (1164)..(1166)
<223> OTHER INFORMATION: n is a, c, g, or t
<220> FEATURE:
<221> NAME/KEY: misc_feature
<222> LOCATION: (1172)..(1175)
<223> OTHER INFORMATION: n is a, c, g, or t
<220> FEATURE:
<221> NAME/KEY: misc_feature
<222> LOCATION: (1178)..(1178)
<223> OTHER INFORMATION: n is a, c, g, or t
<220> FEATURE:
<221> NAME/KEY: misc_feature
<222> LOCATION: (1181)..(1183)
<223> OTHER INFORMATION: n is a, c, g, or t
<220> FEATURE:
<221> NAME/KEY: misc_feature
<222> LOCATION: (1185)..(1187)
<223> OTHER INFORMATION: n is a, c, g, or t
<220> FEATURE:
<221> NAME/KEY: misc_feature
<222> LOCATION: (1190)..(1190)
<223> OTHER INFORMATION: n is a, c, g, or t
<220> FEATURE:
<221> NAME/KEY: misc_feature
<222> LOCATION: (1192)..(1198)
<223> OTHER INFORMATION: n is a, c, g, or t
<220> FEATURE:
<221> NAME/KEY: misc_feature
<222> LOCATION: (1200)..(1205)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1213)..(1213)
<223> OTHER INFORMATION: n is a, c, g, or t
<220> FEATURE:
<221> NAME/KEY: misc_feature
<222> LOCATION: (1217)..(1217)
<223> OTHER INFORMATION: n is a, c, g, or t
<220> FEATURE:
<221> NAME/KEY: misc_feature
<222> LOCATION: (1219)..(1221)
<223> OTHER INFORMATION: n is a, c, g, or t
```

<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1228)..(1228)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t

<400> SEQUENCE: 4

| | | | | | |
|---|---|---|---|---|---|
| nnnnnngnnn | ntgttacgac | ttagccctag | ttaccagttt | taccctaggc | agctccttgc | 60 |
| ggtcaccgac | ttcaggcacc | cccagcttcc | atggcttgac | gggcggtgtg | tacaaggccc | 120 |
| gggaacgtat | tcaccggatc | atggctgata | tccgattact | agcgattcca | gcttcacgga | 180 |
| gtcgagttgc | agactccgat | ccgaactgtg | accggcttta | tagattcgct | cccctcgcg | 240 |
| aggtggctgc | tctctgtacc | ggccattgta | gcacgtgtgt | agcccaaggc | gtaagggccg | 300 |
| tgatgatttg | acgtcatccc | caccttcctc | acagtttgca | ctggcagtct | tgttagagtt | 360 |
| cccgaccgaa | tcgctggcaa | ctaacaacag | gggttgcgct | cgttatagga | cttaacctga | 420 |
| cacctcacgg | cacgagctga | cgacaaccat | gcagcacctt | gtaatttgtc | ttgcgaaaga | 480 |
| tctgtttcca | aatcggtcaa | actacattta | agccttggta | aggttcctcg | cgtatcatcg | 540 |
| aattaaacca | catgctccac | cgcttgtgcg | ggcccccgtc | aattcctttg | agtttcaggc | 600 |
| ttgcgcccgt | actccccagg | tgggatactt | atcactttcg | cttagccact | gaacttgcgc | 660 |
| ccaacagcta | gtatccatcg | tttacggcgt | ggactaccag | ggtatctaat | cctgttcgct | 720 |
| acccacgctt | tcgtccatca | gcgtcaatcc | attagtagta | acctgccttc | gcaattggta | 780 |
| ttccatgtaa | tctctaagca | tttcaccgct | acactacata | ttctagttac | ttcctaataa | 840 |
| ttcaagtcca | gcagtatcaa | tggccgttcc | accgttgagc | gatgggcttt | caccactgac | 900 |
| ttactagacc | gcctacagac | cctttaaacc | caatgattcc | ngataacgct | tggatcctcc | 960 |
| gtattaccgc | ggctgctggc | acgganttag | ccgatcctta | nncttacgat | accgtcagtc | 1020 |
| tctacacgta | gagngttnnt | ctcgtacaaa | agcagcttac | atccatagga | cgtcatcngc | 1080 |
| nngcnncatg | gctnnnnnna | ntgcnncatg | acnnnttcnt | canngctgcn | ncgnangann | 1140 |
| tgncnngnct | cnnncagtnn | gngnnnctcc | cnnnnagnac | nnncnngtn | gnnnnnnnan | 1200 |
| nnnnncccta | acnaacnann | nttnaagngg | nan | | | 1233 |

<210> SEQ ID NO 5
<211> LENGTH: 1416
<212> TYPE: DNA
<213> ORGANISM: Unknown
<220> FEATURE:
<223> OTHER INFORMATION: Consensus Sequence

<400> SEQUENCE: 5

| | | | | | |
|---|---|---|---|---|---|
| gcttaccatg | cagtcgaggg | gtagaattct | tcggaatttg | agaccggcgc | acgggtgcgt | 60 |
| aacgcgtatg | caatctgcct | ttcacagagg | gatagcccag | agaaatttgg | attaatacct | 120 |
| catagtatta | tggagtggca | tcactttata | attaaagtca | caacggtgaa | agatgagcat | 180 |
| gcgtcccatt | agctagttgg | taaggtaacg | gcttaccaag | gcgacgatgg | gtaggggtcc | 240 |

-continued

```
tgagagggag atccccaca ctggtactga gacacggacc agacttatac gggaggcagc    300
agtgaggaat attggtcaat ggacgcaagt ctgaaccagc catgccgcgt gcaggatgac    360
ggtcctatgg attgtaaact gcttttgtac gagaagaaac acctctacgt gtagagactt    420
gacggtatcg taagaataag gatcggctaa ctccgtgcca gcagccgcgg taatacggag    480
gatccaagcg ttatccggaa tcattgggtt taaagggtct gtaggcggtc tagtaagtca    540
gtggtgaaag cccatcgctc aacggtggaa cggccattga tactgctgga cttgaattat    600
taggaagtaa ctagaatatg tagtgtagcg gtgaaatgct tagagattac atggaatacc    660
aattgcgaag gcaggttact actaatggat tgacgctgat ggacgaaagc gtgggtagcg    720
aacaggatta gataccctgg tagtccacgc cgtaaacgat ggatactagc tgttgggcgc    780
aagttcagtg gctaagcgaa agtgataagt atcccacctg gggagtacgg gcgcaagcct    840
gaaactcaaa ggaattgacg ggggcccgca caagcggtgg agcatgtggt ttaattcgat    900
gatacgcgag gaaccttacc aaggcttaaa tgtagtttga ccgatttgga aacagatctt    960
tcgcaagaca aattacaagg tgctgcatgg ttgtcgtcag ctcgtgccgt gaggtgtcag   1020
gttaagtcct ataacgagcg caaccnctgt tgttagttgc cagcgattcg gtcgggaact   1080
ctaacaagac tgccagtgca aactgtgagg aaggtgggga tgacgtcaaa tcatcacggc   1140
ccttacgcct gggctacac acgtgctaca atggccggta cagagagcag ccacctcgcg   1200 aggggggagcg aatctataaa gccggtcaca gttcggatcg gagtctgcaa ctcgactccg   1260
tgaagctgga atcgctagta atcggatatc agccatgatc cggtgaatac gttcccgggc   1320
cttgtacaca ccgcccgtca agccatgaa gctgggggtg cctgaagtcg gtgaccgcaa   1380
ggagctgcct agggtaaaac tggtaactag ggctaa                              1416
```